US010653342B2

(12) United States Patent
Rogers et al.

(10) Patent No.: US 10,653,342 B2
(45) Date of Patent: May 19, 2020

(54) SOFT, WEARABLE MICROFLUIDIC SYSTEMS CAPABLE OF CAPTURE, STORAGE, AND SENSING OF BIOFLUIDS

(71) Applicants: The Board of Trustees of the University of Illinois, Urbana, IL (US); Northwestern University, Evanston, IL (US)

(72) Inventors: John A. Rogers, Wilmette, IL (US); Jungil Choi, Chicago, IL (US); Sungbong Kim, Champaign, IL (US)

(73) Assignees: The Board of Trustees of the University of Illinois, Urbana, IL (US); Northwestern University, Evanston, IL (US)

( * ) Notice: Subject to any disclaimer, the term of this patent is extended or adjusted under 35 U.S.C. 154(b) by 161 days.

(21) Appl. No.: 15/625,087

(22) Filed: Jun. 16, 2017

(65) Prior Publication Data
US 2018/0064377 A1 Mar. 8, 2018

Related U.S. Application Data

(60) Provisional application No. 62/351,734, filed on Jun. 17, 2016, provisional application No. 62/422,536, filed on Nov. 15, 2016.

(51) Int. Cl.
*A61B 5/00* (2006.01)
*A61B 5/145* (2006.01)
(Continued)

(52) U.S. Cl.
CPC ........ *A61B 5/14517* (2013.01); *A61B 5/0059* (2013.01); *A61B 5/6833* (2013.01);
(Continued)

(58) Field of Classification Search
CPC .... A61B 2560/0214; A61B 2560/0462; A61B 5/0059; A61B 5/14517; G01N 33/50
See application file for complete search history.

(56) References Cited

U.S. PATENT DOCUMENTS 7,195,733 B2 3/2007 Rogers et al.
7,521,292 B2 4/2009 Rogers et al.
(Continued)

FOREIGN PATENT DOCUMENTS

WO WO2014/124044 8/2014
WO WO2014/124049 8/2014
(Continued)

OTHER PUBLICATIONS

Alvear-Ordenes, I. et al., "Sweat lactate, ammonia, and urea in rugby players," Int J Sports Med, 26 (2005), pp. 632-637.
(Continued)

*Primary Examiner* — Jennifer Wecker
(74) *Attorney, Agent, or Firm* — Leydig, Voit & Mayer, Ltd.

(57) ABSTRACT

The invention provides systems for handling biofluids including the transport, capture, collection, storage, sensing, and/or evaluation of biofluids released by tissue. Systems of some aspects provide a versatile platform for characterization of a broad range of physical and/or chemical biofluid attributes in real time and over clinically relevant timeframes. Systems of some aspects provide for collection and/or analysis of biofluids from conformal, watertight tissue interfaces over time intervals allowing for quantitative temporal and/or volumetric characterization of biofluid release, such as release rates and release volumes.

68 Claims, 41 Drawing Sheets

(51) Int. Cl.
*G01N 33/50* (2006.01)
*C12M 3/00* (2006.01)
*B01L 3/00* (2006.01)

(52) U.S. Cl.
CPC ............ *B01L 3/5027* (2013.01); *G01N 33/50* (2013.01); *A61B 2560/0214* (2013.01); *A61B 2560/0462* (2013.01); *B01L 2300/0627* (2013.01); *B01L 2300/0803* (2013.01); *B01L 2300/0864* (2013.01); *B01L 2300/0883* (2013.01); *B01L 2300/123* (2013.01); *B01L 2400/0406* (2013.01)

(56) References Cited

U.S. PATENT DOCUMENTS

| | | | |
|---|---|---|---|
| 7,557,367 | B2 | 7/2009 | Rogers et al. |
| 7,622,367 | B1 | 11/2009 | Nuzzo et al. |
| 7,704,684 | B2 | 4/2010 | Rogers et al. |
| 7,705,280 | B2 | 4/2010 | Nuzzo et al. |
| 7,799,699 | B2 | 9/2010 | Nuzzo et al. |
| 7,932,123 | B2 | 4/2011 | Rogers et al. |
| 7,943,491 | B2 | 5/2011 | Nuzzo et al. |
| 7,972,875 | B2 | 7/2011 | Rogers et al. |
| 7,982,296 | B2 | 7/2011 | Nuzzo et al. |
| 8,039,847 | B2 | 10/2011 | Nuzzo et al. |
| 8,198,621 | B2 | 6/2012 | Rogers et al. |
| 8,217,381 | B2 | 7/2012 | Rogers et al. |
| 8,367,035 | B2 | 2/2013 | Rogers et al. |
| 8,394,706 | B2 | 3/2013 | Nuzzo et al. |
| 8,440,546 | B2 | 5/2013 | Nuzzo et al. |
| 8,470,701 | B2 | 6/2013 | Rogers et al. |
| 8,552,299 | B2 | 10/2013 | Rogers et al. |
| 8,562,095 | B2 | 10/2013 | Alleyne et al. |
| 8,664,699 | B2 | 3/2014 | Nuzzo et al. |
| 8,666,471 | B2 | 3/2014 | Rogers et al. |
| 8,679,888 | B2 | 3/2014 | Rogers et al. |
| 8,722,458 | B2 | 5/2014 | Rogers et al. |
| 8,729,524 | B2 | 5/2014 | Rogers et al. |
| 8,754,396 | B2 | 6/2014 | Rogers et al. |
| 8,865,489 | B2 | 10/2014 | Rogers et al. |
| 8,895,406 | B2 | 11/2014 | Rogers et al. |
| 8,905,772 | B2 | 12/2014 | Rogers et al. |
| 8,934,965 | B2 | 1/2015 | Rogers et al. |
| 8,946,683 | B2 | 2/2015 | Rogers et al. |
| 9,057,994 | B2 | 6/2015 | Rogers et al. |
| 9,061,494 | B2 | 6/2015 | Rogers et al. |
| 9,105,555 | B2 | 8/2015 | Rogers et al. |
| 9,105,782 | B2 | 8/2015 | Rogers et al. |
| 9,117,940 | B2 | 8/2015 | Rogers et al. |
| 9,278,522 | B2 | 3/2016 | Alleyne et al. |
| 9,324,733 | B2 | 4/2016 | Rogers et al. |
| 9,349,900 | B2 | 5/2016 | Rogers et al. |
| 9,442,285 | B2 | 9/2016 | Rogers |
| 9,450,043 | B2 | 9/2016 | Nuzzo et al. |
| 9,487,002 | B2 | 11/2016 | Rogers et al. |
| 9,496,229 | B2 | 11/2016 | Rogers et al. |
| 9,554,484 | B2 | 1/2017 | Rogers et al. |
| 9,555,644 | B2 | 1/2017 | Rogers et al. |
| 9,647,171 | B2 | 5/2017 | Rogers et al. |
| 9,691,873 | B2 | 6/2017 | Rogers et al. |
| 9,765,934 | B2 | 9/2017 | Rogers et al. |
| 9,936,574 | B2 | 4/2018 | Rogers et al. |
| 9,986,924 | B2 | 6/2018 | Rogers et al. |
| 10,064,269 | B2 | 8/2018 | Rogers et al. |
| 10,154,592 | B2 | 12/2018 | Rogers et al. |
| 2007/0179371 | A1 | 8/2007 | Peyser et al. |
| 2008/0055581 | A1 | 3/2008 | Rogers et al. |
| 2011/0073475 | A1* | 3/2011 | Kastanos ............ A61B 5/14532 204/403.01 |
| 2012/0157804 | A1 | 6/2012 | Rogers et al. |
| 2013/0041235 | A1 | 2/2013 | Rogers et al. |
| 2014/0025000 | A1* | 1/2014 | Currie .................. A61B 5/0059 604/66 |
| 2014/0220422 | A1 | 8/2014 | Rogers et al. |
| 2015/0080695 | A1 | 3/2015 | Rogers et al. |
| 2015/0141767 | A1 | 5/2015 | Rogers et al. |
| 2015/0237711 | A1 | 8/2015 | Rogers et al. |
| 2016/0361715 | A1* | 12/2016 | Shi ................... A61B 5/150022 |
| 2016/0374758 | A1* | 12/2016 | Jones .................. A61N 5/0616 606/9 |
| 2017/0130187 | A1* | 5/2017 | Lee ........................ C12M 41/40 |
| 2017/0200707 | A1 | 7/2017 | Rogers et al. |
| 2017/0231571 | A1* | 8/2017 | Rogers ................. A61B 5/6833 600/301 |
| 2018/0020966 | A1* | 1/2018 | Begtrup .................. A61B 5/01 600/301 |

FOREIGN PATENT DOCUMENTS

| | | | |
|---|---|---|---|
| WO | WO2014/126927 | 8/2014 | |
| WO | WO2014/138465 | 9/2014 | |
| WO | WO2014/165686 | 10/2014 | |
| WO | WO2016/025468 | 2/2016 | |
| WO | WO-2016025468 A2 * | 2/2016 | ........... A61B 5/6833 |
| WO | WO2016/080911 | 5/2016 | |
| WO | WO-2016080911 A1 * | 5/2016 | ........... A61B 5/7267 |
| WO | WO2018/209100 | 11/2018 | |
| WO | WO2018/223033 | 12/2018 | |
| WO | WO2018/223044 | 12/2018 | |
| WO | WO2018/223058 | 12/2018 | |

OTHER PUBLICATIONS

Bandodkar, A.J. et al., "Epidermal tattoo potentiometric sodium sensors with wireless signal transduction for continuous non-invasive sweat monitoring," Biosens. Bioelectron., 54 (2014), pp. 603-609.

Bandodkar, A.J. et al., "Tattoo-based potentiometric ion-selective sensors for epidermal pH monitoring," Analyst, 138 (1) (2013), pp. 123-128, DOI 10.1039/c2an36422k.

Bhagat, A.A.S. et al., "A passive planar micromixer with obstructions for mixing at low Reynolds numbers," J Micromech Microeng, 17 (5), (2007), pp. 1017-1024, DOI 10.1088/0960-1317/17/5/023.

Biagi, S. et al., "Simultaneous determination of lactate and pyruvate in human sweat using reversed-phase high-performance liquid chromatography: a noninvasive approach," Biomed. Chromatogr., 26 (2012), pp. 1408-1415.

Bietsch, A. et al., "Conformal contact and pattern stability of stamps used for soft lithography," J Appl Phys, 88 (7), (2000), pp. 4310-4318, DOI 10.1063/1.1289816.

Boysen, T.C. et al., "A modified anaerobic method of sweat collection," Journal of Applied Physiology, 56 (1984), pp. 1302-1307.

Brassard, D. et al., "3D thermoplastic elastomer microfluidic devices for biological probe immobilization," Lab Chip, 11 (23), (2011), pp. 4099-4107, DOI 10.1039/c1lc20714h.

Chen, C.H. et al., "A planar electroosmotic micropump," J Microelectromech S, 11 (6), (2002), pp. 672-683, DOI 10.1109/Jmems.2002.805055.

Chen, J.M. et al., "Analysis and experiment of capillary valves for microfluidics on a rotating disk," Microfluid Nanofluid, 4 (5), (2008), pp. 427-437, DOI 10.1007/s10404-007-0196-x.

Cho, H. et al., How the capillary burst microvalve works, J Colloid Interface Sci, 306 (2), (2007), pp. 379-385, DOI 10.1016/j.jcis.2006.10.077.

Choi, J. et al., "Rapid antibiotic susceptibility testing by tracking single cell growth in a microfluidic agarose channel system," Lab Chip, 13 (2), (2013), pp. 280-287, DOI 10.1039/c2lc41055a.

Corrie, S. et al., "Blood sweat, and tears: developing clinically relevant protein biosensors for integrated body fluid analysis," Analyst, 140 (2015), pp. 4350-4364.

Costa, F. et al., "Regional and Total Body Sweat Composition of Men Fed Controlled Diets," Am J Clin Nutr, 22 (1), (1969), pp. 52-58.

Coyle, S. et al., "BIOTEX—biosensing textiles for personalized healthcare management," IEEE Trans. Inf. Technol. Biomed., 14 (2010) pp. 364-370.

(56) References Cited

OTHER PUBLICATIONS

Crocker, H. et al., "Evaluation of an enzymatic method for determining creatinine in plasma," Journal of clinical pathology, 41 (1988), pp. 576-581.
Curto, V.F. et al., "Real-time sweat pH monitoring based on a wearable chemical barcode micro-fluidic platform incorporating ionic liquids," Sensor. Atuat. B-Chem., 171-172 (2012), pp. 1327-1334.
Dagdeviren, C. et al., "Conformal piezoelectric systems for clinical and experimental characterization of soft tissue biomechanics," Nature Mater., 14 (2015), pp. 728-736.
Dill, D.B. et al., "Calculation of percentage changes in volumes of blood, plasma, and red cells in dehydration," J Appl Physiol, 37(2) (1974), pp. 247-248.
Di Sant'Agnese, P.A. et al., "Sweat electrolyte disturbances associated with childhood pancreatic disease," the American Journal of Medicine, 15 (6) (1953), pp. 777-784, DOI 10.1016/0002-9343(53)90169-7.
Eddington, D.T. et al., "Thermal aging and reduced hydrophobic recovery of polydimethylsiloxane," Sensor Actuat B-Chem, 114 (1), (2006), pp. 170-172, DOI 10.1016/j.snb.2005.04.037.
Fukumoto, T. et al., "Differences in composition of sweat induced by thermal exposure and by running exercise," Clin Cardiol, 11 (10), (1988), pp. 707-709.
Gao, L. et al., "Epidermal photonic devices for quantitative imaging of temperature and thermal transport characteristics of the skin," Nat Commun, 5 (2014), pp. 1-10.
Gao, W. et al., "Fully integrated wearable sensor arrays for multiplexed in situ perspiration analysis," Nature, 529 (2016), pp. 509-514.
Gibson, L.E. et al., "A Test for Concentration of Electrolytes in Sweat in Cystic Fibrosis of the Pancreas Utilizing Pilocarpine by Iontophoresis," Pediatrics, 23 (3) (1959), pp. 545-549.
Glass, N.R. et al., "Miniaturized Lab-on-a-Disc (miniLOAD)," Small, 8 (12), (2012), pp. 1881-1888, DOI 10.1002/smll.201102282.
Guinovart, T. et al., "A potentiometric tattoo sensor for monitoring ammonium in sweat," Analyst, 138 (2013), pp. 7031-7038.
Halldorsson, S. et al., "Advantages and challenges of microfluidic cell culture in polydimethylsiloxane devices," Biosens Bioelectron, 63, (2015), pp. 218-231, DOI 10.1016/j.bios.2014.07.029.
Hammond, K.B. et al., "Clinical evaluation of the macroduct sweat collection system and conductivity analyzer in the diagnosis of cystic fibrosis," J Pediatr, 124 (2), (1994), pp. 255-260, DOI Doi 10.1016/S0022-3476(94)70314-0.
Harvey, C.J. et al., "Formulation and stability of a novel artificial human sweat under conditions of storage and use," Toxicology in Vitro, 24, (2010), pp. 1790-1796.
Heikenfeld, J., "Non-invasive Analyte Access and Sensing through Eccrine Sweat: Challenges and Outlook circa 2016," Electroanalysis, 28 (2016), pp. 1242-1249.
Hou, L. et al., "Artificial microfluidic skin for in vitro perspiration simulation and testing," Lab on a Chip, 13 (2013), pp. 1868-1875.
Huang, C.P. et al., "Engineering microscale cellular niches for three-dimensional multicellular co-cultures," Lab Chip, 9 (12), (2009), pp. 1740-1748, DOI 10.1039/b818401a.
Huang, X. et al., "Stretchable, wireless sensors and functional substrates for epidermal characterization of sweat," Small, 10 (2014), pp. 3083-3090.
Huang, Y.Y. et al., "Stamp collapse in soft lithography," Langmuir, 21 (2005), pp. 8058-8068.
Imani, S. et al., "A wearable chemical-electrophysiological hybrid biosensing system for real-time health and fitness monitoring," Nat Commun, 7, (2016), pp. 11650, DOI 10.1038/ncomms11650.
International Search Report and Written Opinion corresponding to PCT Application No. PCT/US17/37852, dated Sep. 26, 2017.
Jadoon, S. et al., "Recent developments in sweat analysis and its applications," vol. 2015 (2015), pp. 7.
Jeong, J.W. et al., "Wireless optofluidic systems for programmable in vivo pharmacology and optogenetics," Cell, 162 (2015), pp. 662-674.
Jeong, J.W. et al., "Materials and optimized designs for human-machine interfaces via epidermal electronics," Advanced Materials, 25 (2013), pp. 6839-6846.
Jia, W. et al., "Electrochemical tattoo biosensors for real-time noninvasive lactate monitoring in human perspiration," Analytical Chemistry, 85 (2013), pp. 6553-6560.
Kaltenbrunner, M. et al, "An ultra-lightweight design for imperceptible plastic electronics," Nature, 499 (2013), pp. 458-463.
Kang, D. et al., "Ultrasensitive mechanical crack-based sensor inspired by the spider sensory system," Nature, 516 (2014), pp. 222-226.
Khang, D.Y. et al., "A Stretchable Form of Single-Crystal Silicon for High-Performance Electronics on Rubber Substrates," Science, 311 (5758), (2006), pp. 208-212, DOI 10.1126/science.1121401.
Kidwell, D.A. et al., "Susceptibility of PharmChek™ drugs of abuse patch to environmental contamination," Forensic Sci Int, 116 (2-3), (2001), pp. 89-106, DOI 10.1016/S0379-0738(00)00353-4.
Kim, D.H. et al., "Flexible and Stretchable Electronics for Biointegrated Devices," Annual Review of Biomedical Engineering, 14 (2012), pp. 113-128.
Kim, D.H. et al., "Epidermal electronics," Science, 333 (2011), pp. 838-843.
Kim, J. et al., "Wearable temporary tattoo sensor for real-time trace metal monitoring in human sweat," Electrochemistry Communications, 51 ©, (2015), pp. 41-45, DOI 10.1016/j.elecom.2014.11.024.
Kim, J. et al., "Epidermal electronics with advanced capabilities in near-field communication," Small, 11 (2015), pp. 906-912.
Kim, T.-i. et al., "Injectable, cellular-scale optoelectronics with applications for wireless optogenetics," Science, 340 (2013), pp. 211-216.
Klode, J. et al., "Investigation of adhesion of modern wound dressings: a comparative analysis of 56 different wound dressings," Journal of the European Academy of Dermatology and Venereology, 25 (2011), pp. 933-939.
Kong, L.X. et al., "Lab-on-a-CD: A Fully Integrated Molecular Diagnostic System," J Lab Autom, 21 (3), (2016), pp. 323-355, DOI 10.1177/2211068215588456.
Lamont, L.S., "Sweat lactate secretion during exercise in relation to women's aerobic capacity," Journal of Applied Physiology, 62 (1987), pp. 194-198.
Lee, C.H. et al., "Soft core/dhell packages for stretchable electronics," Adv. Funct. Mater., 25 (2015), pp. 3698-3704.
Lee, J.N. et al., "Solvent compatibility of poly (dimethylsiloxane)-based microfluidic devices," Anal. Chem., 75 (2003), pp. 6544-6554.
LeGrys, V.A. et al., "Sweat testing: Sample collection and quantitative analysis," approved guideline (Document C34-A3), National Committee for Clinical Laboratory Standards, (2000), Wayne, PA.
Liang, X. et al., "Biomechanical properties of in vivo human skin from dynamic optical coherence elastography," IEEE Trans. Biomed. Eng., 57 (2010), pp. 953-959.
Licht, P.B. et al., "Severity of compensatory sweating after thoracoscopic sympathectomy," Ann. Thorac. Surg., 78 (2004), pp. 427-431.
Lipomi, D.J. et al., "Skin-like pressure and strain sensors based on transparent elastic films of carbon nanotubes," Nature Nanotech, 6 (2011), pp. 788-792.
Lotters, J.C. et al., "The mechanical properties of the rubber elastic polymer polydimethylsiloxane for sensor applications," J Micromech Microeng, 7 (3), (1997), pp. 145-147, DOI 10.1088/0960-1317/7/3/017.
Madou, M. et al., "Lab on a CD," Annu Rev Biomed Eng, 8, (2006), pp. 601-628, DOI 10.1146/annurev.bioeng.8.061505.095758.
Martinez, A.W. et al., "Simple telemedicine for developing regions: camera phones and paper-based microfluidic devices for real-time, off-site diagnosis," Anal. Chem., 80 (2008), pp. 3699-3707.
Martinez, A.W. et al., "Patterned paper as a platform for inexpensive, low-volume, portable bioassays," Angew. Chem. Int. Edit., 46 (2007), pp. 1318-1320.

(56) References Cited

OTHER PUBLICATIONS

Matzeu, G. et al., "Advances in wearable chemical sensor design for monitoring biological fluids," Sens. Actuators B Chem., 211 (2015), pp. 403-418.

Mena-Bravo, A. et al., "Sweat: A sample with imited present applications and promising future in metabolomics," J Pharm Biomed Anal, 90 (2014), pp. 139-147, DOI 10.1016/j.jpba.2013.10.048.

Mickelsen, O. et al., "The Composition of Sweat, With Special Reference to the Vitamins," J Biol Chem, 149 (2), (1943), pp. 479-490.

Mukerjee, E.V., "Microneedle array for transdermal biological fluid extraction and in situ analysis," Sensors and Actuators A, 114 (2004), pp. 267-275.

Nyein, H.Y. et al., "A Wearable Electrochemical Platform for Noninvasive Simultaneous Monitoring of $Ca^{2+}$ and pH," Acs Nano, 10 (7), (2016), pp. 7216-7224, DOI 10.1021/acsnano.6b04005.

Ohtani, O. et al., "Collagen fibrillary networks as skeletal frameworks: a demonstration by cell-maceration/scanning electron microscope method," Arch. Histol. Cytol., 51, (1988), pp. 249-261.

Oncescu, V. et al., "Smartphone based health accessory for colorimetric detection of biomarkers in sweat and saliva," Lab. Chip., 13 (2013), pp. 3232-3238.

Pang, C. et al., "A flexible and highly sensitive strain-gauge sensor using reversible interlocking of nanofibers," Nature Mater., 11 (2012), pp. 795-801.

Polliack, A. et al., "Sweat analysis following pressure ischaemia in a group of debilitated subjects," JRRD, 34 (1997), pp. 303-308.

Rogers, J.A., "Electronics for the human body," JAMA, 313 (2015), pp. 561-562.

Rose, D. et al., "Adhesive RFID sensor patch for monitoring of sweat electrolytes," IEEE Trans. Biomed. Eng., 62 (2014), pp. 1457-1465.

Salvo, P. et al., "A wearable sensor for measuring sweat rate," IEEE Sensors J., 10 (2010), pp. 1557-1558.

Sato, K. et al., "Individual variations in structure and function of human eccrine sweat gland," Am. J. Physiol. Regul. Integr. Comp. Physiol., 245 (1983), pp. R203-R208.

Schulz, I.J., "Micropuncture studies of the sweat formation in cystic fibrosis patients," Invest, 48 (8), (1969), pp. 1470-1477, DOI 10.1172/JCI106113.

Shamsuddin, A.K. et al., "Changes in the index of sweat ion concentration with increasing sweat during passive heat stress in humans," Eur J Appl Physiol, 94 (3), (2005), pp. 292-297, DOI 10.1007/s00421-005-1314-7.

Shen, L. et al., "Point-of-care colorimetric detection with a smartphone," Lab on a Chip, 12 (2012), pp. 4240-4243.

Shirreffs, S.M. et al., "Whole body sweat collection in humans: an improved method with preliminary data on electrolyte content," J. Appl. Physiol., 82 (1997), pp. 336-341.

Smith, C.J. et al., "Body mapping of sweating patterns in male athletes in mild exercise-induced hyperthermia," Eur. J. Appl. Physiol., 111 (2011), pp. 1391-1404.

Song, Y. et al., "Graphene oxide: intrinsic peroxidase catalytic activity and its application to glucose detection," Advanced Materials, 22 (2010), pp. 2206-2210.

Sonner, Z. et al., "The microfluidics of the eccrine sweat gland, including biomarker partitioning, transport, and biosensing implications," Biomicrofluidics, 9 (2015), 031301.

Takei, K. et al., "Nanowire active-matrix circuitry for low-voltage macroscale artificial skin," Nature Mater., 9 (2010), pp. 821-826.

Taylor, N.A. et al., "Regional variations in transepidermal water loss, eccrine sweat gland density, sweat secretion rates and electrolyte composition in resting and exercising humans," Extrem. Physiol. Med., 2 (2013), pp. 1-30.

Ullmann, A et al., "The piezoelectric valve-less pump—improved dynamic model," Microelectromech S, 11 (6), (2002), pp. 655-664, DOI 10.1109/Jmems.2002.805048.

Ventsel, E. et al., "Thin plates and shells: theory: analysis, and applications Ch. 3," CRC press, Boca Raton, FL, 2001.

Viventi, J. et al., "Flexible, foldable, actively multiplexed, high-density electrode array for mapping brain activity in vivo," Nat. Neurosci., 14 (2011), pp. 1599-1605.

Webb, R.C. et al., "Ultrathin conformal devices for precise and continuous thermal characterization of human skin," Nature Mater., 12 (2013), pp. 938-944.

Wei, H. et al., "$Fe_3O_4$ Magnetic Nanoparticles as Peroxidase Mimetics and Their Applications in $H_2O_2$ and Glucose Detection," Analytical Chemistry, 80 (2008), pp. 2250-2254.

Wilke, K. et al., "A short history of sweat gland biology," Int. J. Cosmet. Sci., 29 (2007), pp. 169-179.

Xia, H.M. et al., "Chaotic micromixers using two-layer crossing channels to exhibit fast mixing at low Reynolds numbers," Lab Chip, 5 (7), (2005), pp. 748-755, DOI 10.1039/b502031j.

Zhao, B. et al., "Principles of Surface-Directed Liquid Flow in Microfluidic Channels," Anal Chem, 74 (16), (2002), pp. 4259-4268, DOI 10.1021/ac020269w.

Bandodkar et al. "Soft, skin-interfaced microfluidic systems with passive galvanic stopwatches for precise chronometric sampling of sweat," *Adv. Mater.* 1902109, 2019, 9 pages.

Bandodkar et al. "Battery-free, skin-interfaced microfluidic/electronic systems for simultaneous electrochemical, colorimetric, and volumetric analysis of sweat," Sci. Adv. 5: eaav3294, Jan. 18, 2019, 15 pages.

Choi et al. "Soft, skin-integrated multifunctional microfluidic systems for accurate colorimetric analysis of sweat biomarkers and temperature." *ACS Sens.* 4, 2, 379-388, Feb. 1, 2019.

Zhang et al. "Passive sweat collection and colorimetric analysis of biomarkers relevant to kidney disorders using a soft microfluidic system," *Lab Chip.* 19:1545-55, 2019.

* cited by examiner

SOFT, WEARABLE MICROFLUIDIC SYSTEMS CAPABLE OF CAPTURE, STORAGE, AND SENSING OF BIOFLUIDS

CROSS-REFERENCE TO RELATED APPLICATIONS

This application claims the benefit of and priority to U.S. Provisional Application No. 62/351,734, filed Jun. 17, 2016, and U.S. Provisional Application No. 62/422,536, filed Nov. 15, 2016, each of which is hereby incorporated in its entirety.

STATEMENT REGARDING FEDERALLY SPONSORED RESEARCH OR DEVELOPMENT

This invention was made with government support under UES S-977-02A-001 UIUC subaward awarded by the U.S. Air Force. The government has certain rights in the invention.

BACKGROUND OF INVENTION

Emerging wearable sensor technologies offer attractive solutions for continuous, personal health/wellness assessment, forensic examination, patient monitoring and motion recognition. Recent advances in epidermal electronics provide classes of skin-mounted sensors and associated electronics in physical formats that enable intimate contact with the skin for long-term, reliable health monitoring.

An important measurement mode in such devices may involve the analysis of body fluids (e.g., blood, interstitial fluid, sweat, saliva, and tear), to gain insights into various aspects of physiological health. Such function in wearable sensors, generally, and epidermal electronics in particular, is relatively unexplored. Existing devices either use complex fluidic systems for sample handling or involve purely concentration-based measurement without sample collection and storage, or access to parameters related to quantity and rate. In addition, mechanical fixtures, straps and/or tapes that are typically required to maintain contact of these devices with the skin do not lend themselves well to continuous, long term monitoring without discomfort.

SUMMARY OF THE INVENTION

The invention provides systems for handling biofluids including the transport, capture, collection, storage, sensing, and/or evaluation of biofluids released from by tissue. Systems of some aspects provide a versatile platform for characterization of a broad range of physical and/or chemical biofluid attributes in real time and over clinically relevant timeframes. Systems of some aspects provide for collection and/or analysis of biofluids from conformal, watertight tissue interfaces over time intervals allowing for quantitative temporal and/or volumetric characterization of biofluid release, such as release rates and release volumes. Systems of some aspects provide for multi-parametric and/or temporal profiling including tandem sensing and/or quantification of multiple analytes in biofluids as a function of time. Systems of some aspects integrate functional substrates implementing fluidic handling systems using biocompatible materials providing for time dependent fluidic capture and quantification while maintaining a robust tissue interface and minimizing artificial changes to the release of biofluids. Systems of some aspects, for example, integrate wireless information transfer in connection with capture, sensing and/or collection, including via near field communication and systems capable of wireless electronic interfaces to external devices, e.g. for image capture and/or analysis. Systems of some aspects are useful for temporal evaluation of the physical state and/or composition of tissue, for example, for identification and/or monitoring of health and/or the onset or progression of disease.

In some embodiments, aspects of the invention provides skin mounted devices for temporal characterization of sweat including determination of sweat rate, sweat volume and sweat composition as a function of time. Epidermally mounted systems of some embodiments include microfluidic network geometries implemented in thin, elastic form factors and structures providing temporally controlled fluid handling, capture and/or biochemical analytics. Epidermally mounted systems of some aspects include open architecture geometries including passages for transporting a portion of the released sweat away from the devices so as to minimize problems with inducing irritation of the tissue and/or maintaining a watertight interface, for example, during periods of profuse sweating. Epidermally mounted systems of some aspects include systems for capture and collection of sweat for later analysis and systems providing temporal characterization of sweat composition including the concentration of electrolytes and metabolites, for example via colorimetric analysis, optionally for discrete analyte concentration windows.

In an aspect, the invention provides a device for handling a biofluid comprising: (i) a functional substrate for mounting on a surface of the skin; and (ii) one or more sensors supported by the functional substrate; wherein the functional substrate provides for microfluidic transport of at least a portion of the biofluid to the one or more sensors; and wherein the one or more sensors provide for characterization of at least one temporal property of the biofluid.

In an aspect, the invention provides a device for handling a biofluid comprising: (i) a functional substrate for mounting on a surface of the skin; and (ii) a plurality of biofluid collection structures supported by the functional substrate; wherein the functional substrate provides for microfluidic transport of at least a portion of the biofluid to the biofluid collection structures; and wherein each biofluid collection structure receives biofluid corresponding to a different time interval.

In an aspect, the invention provides a device for handling a biofluid comprising: (i) a functional substrate for mounting on a surface of the skin; and (ii) a plurality of sensors supported by the functional substrate; wherein the functional substrate provides for microfluidic transport of at least a portion of the biofluid to the plurality of sensors; wherein the plurality of sensors include at least a first sensor for determining a first concentration of an analyte over a first concentration range and a second sensor for determining a second concentration of the analyte over a second concentration range different from the first concentration range. In an embodiment, for example, first and second sensors each are colorimetric sensors having different color sensitive reagents or concentrations of color sensitive regents to provide sensitive and accurate determination of analyte concentrations over different concentration ranges.

In an aspect, the invention provides a device for handling a biofluid comprising: (i) a functional substrate for mounting on a surface of the skin; and (ii) one or more sensors or biofluid collection structures supported by the functional substrate; wherein the functional substrate provides for microfluidic transport of the biofluid including transport of a first portion of the biofluid to the one or more sensors or biofluid collection structures and transport of a second portion of the biofluid away from the device.

In an embodiment, a device of the invention is provided in physical contact with the skin of a subject. In an embodiment, a device of the invention is provided in conformal contact with the skin of a subject.

Devices of aspects of the invention provide a versatile platform supporting a broad range biofluid handling and manipulation applications including sample collection and in vivo diagnostics and monitoring. In an embodiment, for example, the device is for sensing, monitoring or characterizing a biofluid, such as temporal characterization of one or more physical and/or chemical properties. In an embodiment, the device is for capture, collecting or storing a biofluid, for example, over a well-defined sampling time interval.

Devices of aspects of the invention are useful for temporal characterization of biofluid release, uptake and/or composition. In an embodiment, the device is for determining a temporal property of the biofluid, for example, characterization of physical property and/or chemical property of the biofluid as a function of time or over a known or preselected time domain. In an embodiment, for example, the temporal property of the biofluid is characterized over a time domain selected from the range of 10 μs to 24 hrs, optional for some applications, a time domain selected from the range of 1 ms to 24 hrs. In an embodiment, for example, the temporal property of the biofluid is a biofluid release rate as a function of time or a biofluid release volume as a function of time. In an embodiment, for example, the temporal property of the biofluid is a sweat rate as a function of time or a total sweat volume loss as a function of time. In an embodiment, for example, the temporal property of the biofluid is a time dependent concentration or amount of one or more analytes in the biofluid. In an embodiment, for example, the temporal property of the biofluid is a time dependent concentration of one or more biomarkers in the biofluid.

In an embodiment, for example, the temporal property is a multi-parametric property including the concentrations or amounts of at least two biomarkers as a function of time. In an embodiment, for example, the one or more biomarkers is one or more electrolytes or metabolites.

In an embodiment, for example, the sensors or biofluid collection structures are supported by a functional substrate. "Supported by a functional substrate" may refer to a configuration wherein the sensors or biofluid collection structures are provided directly (e.g., in physical contact) on a surface of the functional substrate, such as an external surface, or provided on an intermediate structure provided on a surface of the functional substrate. "Supported by a functional substrate" may also refer to a configuration wherein the sensors or biofluid collection structures are at least partially, and optionally wholly, integrated with the functional substrate, for example, wherein at least a portion of, and optionally all, of the sensors or biofluid collection structures comprise elements of the functional substrate. In an embodiment, for example, the sensors or biofluid collection structures are integrated with the functional substrate, for example, in a configuration wherein the functional substrate provides one or more walls or other structural elements of reservoirs, microfluidic channels and/or chambers comprising the sensors or biofluid collection structures.

The disclosed devices may mobilize and access biofluids by mechanical, electrical and/or thermal mechanisms including but not limited to surface wicking, microneedle extraction, reverse iontophoresis, capillary action and/or thermal microablasion.

In an embodiment, a device comprises at least one microneedle or an array of microneedles for accessing interstitial fluid or blood. Microneedles may, for example, be fabricated from polymeric materials, silicon or glass using known micromachining techniques. Some methods for making and using microneedles and microneedle arrays are described, for example, in E. V. Mukerjee, "Microneedle array for transdermal biological fluid extraction and in situ analysis," Sensors and Actuators A, 114 (2004) 267-275. In an embodiment, a microneedle or microneedle array may be disposed at a surface of an epidermal device, for example, at a microchannel opening.

The physical properties of the functional substrate are important in establishing a robust interface with the tissue, such as a conformal and/or watertight interface, for example, over clinically relevant timeframes. In an embodiment, for example, the functional substrate is mechanically matched to the skin. In an embodiment, for example, the functional substrate is thermally matched to the skin.

In an embodiment, a functional substrate is an elastomeric substrate. In an embodiment, the functional substrate is substantially colorless and substantially transparent. In an embodiment, the functional substrate has a Young's modulus less than or equal to 100 MPa and optionally in some embodiments less than or equal to 10 MPa. In an embodiment, the functional substrate has a Young's modulus selected from a range of 10 kPa to 10 MPa and in some embodiments selected from a range of 100 kPa to 1 MPa. In an embodiment, the functional substrate has a thickness selected from a range of 500 μm to 2 mm and in some embodiments selected from a range of 500 μm to 1 mm. In some embodiments, the functional substrate is selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA) and polycarbonate. In some embodiments, the functional substrate has a dielectric constant greater than or equal to 2.0. In some embodiments, the functional substrate has a dielectric constant selected from a range of 2.20 to 2.75. In some embodiments, the functional substrate has lateral dimensions or a diameter less than or equal to 700 $mm^2$. In some embodiments, the functional substrate has a permeability for the biofluid greater than or equal to 0.2 g/h $m^2$. In some embodiments, the functional substrate has a coefficient of thermal expansion selected from a range of 1/° C. ($\times 10^{-6}$) to 3/° C. ($\times 10^{-4}$). In some embodiments, the functional substrate has a porosity greater than or equal to 0.5. In an embodiment, for example, the functional substrate has a lateral foot print less than or equal to 1000 $mm^2$. In an embodiment, for example, the functional substrate has a porosity greater than or equal to 0.01, optionally for some embodiments 0.1 and optionally for some embodiments 0.5. In some embodiments, devices of the invention have a porosity selected over the range of 0.1 to 0.6.

Devices of aspects of the invention include self-adhering devices and devices that are adhered to the surface of the skin via an adhesion material, such as an adhesive layer. In an embodiment, for example, the functional substrate is capable of adhering to the surface of the skin. In an embodiment, for example, the functional substrate adheres to the surface of the skin with an adhesion force selected from the range of 1 N to 20 N.

In an embodiment, for example, the functional substrate has one or more inlets in fluid communication with the surface of the skin, optionally wherein the inlets are individually addressed to one or more sweat glands of the skin. In an embodiment, for example, the functional substrate forms a watertight seal with the skin around the one or more inlets.

In an embodiment, for example, the functional substrate comprises a porous material, a micro-machined material, a woven material, a mesh material or a fibrous material. In an embodiment, for example, the functional substrate comprises an adhesive layer having a plurality of micromachined openings. In an embodiment, for example, the functional substrate comprises a microfluidic network for spatially routing at least a portion of the biofluid. In an embodiment, for example, the microfluidic network comprises an elastomeric material. In an embodiment, for example, the microfluidic network comprises one or more microchannels providing for transport of at least a portion of the biofluid. In an embodiment, for example, the microfluidic network comprises a first layer embossed with a relief geometry corresponding to the microchannels and a second top capping layer.

In an embodiment, for example, the transport of biofluid is generated via capillary action, natural pressure of the biofluid or a combination of these.

In an embodiment, for example, the microfluidic network comprises a plurality of microchannels and a plurality of reservoirs, wherein different microchannels of the network are in fluid communication with different reservoirs. In an embodiment, for example, the microchannels and the reservoirs are connected via one or more passive valves or one or more active valves allowing for time dependent collection, analysis or storage of the biofluid. In an embodiment, for example, the microfluidic network further comprises one or more outlets in fluid communication with the microchannels for reducing backpressure in the microfluidic network. In an embodiment, for example, the one or more outlets comprise openings, membranes or a combination thereof.

In an embodiment, for example, the functional substrate further comprise one or more openings providing for passage of an unsampled portion of the biofluid away from the device. In an embodiment, for example, the unsampled portion of the biofluid is transported away vertically or laterally relative to the interface of the device and the skin.

In an embodiment, for example, the functional substrate comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate or any combination.

The devices of aspects of the invention are compatible with a variety of sensors. In an embodiment, for example, the one or more sensors comprise colorimetric sensors. In an embodiment, for example, the one or more colorimetric sensors comprise one or more color-responsive reagents for quantification of a volume, flow rate, composition or any combination of these of the biofluid. In an embodiment, for example, the one or more color-responsive reagents are indicator reagents that react with one or more biomarkers in the biofluid. In an embodiment, for example, the one or more color-responsive reagents are selected from the group consisting of $CoCl_2$, glucose oxidase, peroxidase, potassium iodide, lactate dehydrogenase, diaphorase, formazan dyes, 2,4,6-tris(2-pyridyl)-s-triazine (TPTZ) complexed with mercury ion or iron ion, a 2,2'-bicinchoninic acid, 1,10-phenanthroline, a universal pH indicator or any combination of these.

In an embodiment, for example, one or more color-responsive reagents are provided in a biofluid collection structure of a microfluidic network. In an embodiment, for example, one or more color-responsive reagents are provided in a reservoir. In an embodiment, for example, one or more color-responsive reagents are provided in microfluidic channel.

In an embodiment, for example, the biofluid collection structure of the microfluidic network is at least partially optically transparent in the visible or infrared region of the electromagnetic spectrum. In an embodiment, for example, the biofluid collection structure having the color-responsive reagents is characterized by a volume selected over the range of 1000 $\mu m^3$-1000 $mm^3$. In an embodiment, for example, one or more color-responsive reagents are immobilized within the biofluid collection structure. In an embodiment, for example, one or more color-responsive reagents are immobilized within or on one or more walls of the biofluid collection structure. In an embodiment, for example, one or more color-responsive reagents are immobilized within a hydrogel provided within the biofluid collection structure.

In an embodiment, for example, the color-responsive reagents are provided along the length of the biofluid collection structure comprising a microfluidic channel, wherein the volume of the biofluid in the microchannel is sensed as the biofluid fills the microchannel. In an embodiment, for example, a leading edge of the volume of biofluid in the microchannel is sensed (e.g., optically, visually, mechanically, electrochemically, chemically, etc.) as a function of time. In an embodiment, for example, the leading edge of the volume of the biofluid in the microchannel is sensed optically. In an embodiment, for example, the microchannel is a serpentine microchannel, thereby providing improved sensitivity over a larger operating range without unduly increasing substrated footprint area.

In an embodiment, for example, the color-responsive reagent is provided in the biofluid collection structure, and wherein the concentration of the one or more biomarkers in the biofluid are sensed as the biofluid is provided to the biofluid collection structure. In an embodiment, for example, the concentrations of the one or more biomarkers in the biofluid are sensed optically, optionally visually or with a camera.

In an embodiment, for example, the one or more biofluid collection reservoirs are one or more conduits and/or reservoirs, or are one or more reservoirs. In an embodiment, for example, the one or more biofluid collection reservoirs are one or more chambers. In an embodiment, for example, the one or more biofluid collection reservoirs are one or more microfluidic channels. In an embodiment, for example, the microfluidic channels are characterized by a length selected from a range of 1 mm to 50 cm. In an embodiment, for example, the microfluidic channels are characterized a cross sectional area selected from a range of 100 $\mu m^2$ to 10 $mm^2$.

In an embodiment, for example, the device is read-out passively, for example, by a passive optical, mechanical or electronic signal. In an embodiment, for example, the device is read-out actively, for example, wherein the device actively generates an NFC signal.

In an embodiment, for example, wherein the device is for collecting, storing or analyzing the biofluid. In an embodiment, for example, the biofluid is sweat, blood or interstitial fluid from a subject. In an embodiment, for example, the biofluid is selected from the group consisting of sweat, tears, saliva, gingival crevicular fluid, interstitial fluid, blood and combinations thereof.

In an embodiment, for example, wherein the device is for determining the concentration in one or more biomarkers in the biofluid. In an embodiment, for example, the one or more biomarkers in the biofluid are electrolytes or metabolites.

In an embodiment, for example, the device further comprises an actuator. In an embodiment, for example, the actuator generates electromagnetic radiation, acoustic energy, an electric field, a magnetic field, heat, a RF signal, a voltage, a chemical change or a biological change. In an embodiment, for example, the actuator comprises a heater, a reservoir containing a chemical agent capable of causing a chemical change or a biological change, a source of electromagnetic radiation, a source of an electric field, a source of RF energy or a source of acoustic energy. In an embodiment, for example, the device further comprises a transmitter, receiver or transceiver. In an embodiment, for example, the device further comprises at least one coil. In an embodiment, for example, the at least one coil is a near-field communication coil. In an embodiment, for example, the at least one coil is an inductive coil. In an embodiment, for example, the at least one coil comprises a serpentine trace.

In an embodiment, for example, the device has an average Young's modulus and a thickness within a factor of 2 of a modulus and a thickness of an epidermal layer of the skin of a subject. In an embodiment, for example, the device has an average Young's modulus less than or equal to 500 kPa. In an embodiment, for example, the device has an average Young's modulus selected from a range of 0.5 kPa to 100 kPa. In an embodiment, for example, the device has a net bending stiffness less than or equal to 1 nN m. In an embodiment, for example, the device has a net bending stiffness selected from a range of 0.1 to 1 nN m. In an embodiment, for example, the device has a 2D footprint (e.g., area of the skin interface) selected from a range of 300 mm$^2$ to 2000 cm$^2$.

In an aspect, provided herein are methods of analyzing a biofluid; the methods comprising: (i) providing a device for handling a biofluid; the device comprising: (1) a functional substrate for mounting on a surface of the skin; and (2) one or more sensors supported by the functional substrate; wherein the functional substrate provides for microfluidic transport of at least a portion of the biofluid to the one or more sensors; and wherein the one or more sensors provide for characterization of at least one temporal property of the biofluid; (ii) contacting the functional substrate of the device with a surface of the skin of a subject; and (iii) analyzing the biofluid from the surface of the skin of the subject.

In an aspect, provided herein are methods of collecting a biofluid; the methods comprising: (i) providing a device for handling a biofluid; the device comprising: (1) a functional substrate for mounting on a surface of the skin; and (2) a plurality of biofluid collection structures supported by the functional substrate; wherein the functional substrate provides for microfluidic transport of at least a portion of the biofluid to the biofluid collection structures; and wherein each biofluid collection structure receives biofluid corresponding to a different time interval; (ii) contacting the functional substrate of the device with a surface of the skin of a subject; and (iii) collecting the biofluid from the surface of the skin of the subject.

In an aspect, provided herein are methods of analyzing a biofluid; the methods comprising: (i) providing a device for handling a biofluid; the device comprising: (1) a functional substrate for mounting on a surface of skin; and (2) a plurality of sensors supported by the functional substrate; wherein the functional substrate provides for microfluidic transport of at least a portion of the biofluid to the plurality of sensors; wherein the plurality of sensors include at least a first sensor for determining a first concentration of an analyte over a first concentration range and a second sensor for determining a second concentration of the analyte over a second concentration range different from the first concentration range; (ii) contacting the functional substrate of the device with a surface of the skin of a subject; and (iii) analyzing the biofluid from the surface of the skin of the subject.

In an aspect, provided herein are methods of sampling a biofluid; the methods comprising: (i) providing a device for handling a biofluid; the device comprising: (1) a functional substrate for mounting on a surface of the skin; and (2) one or more sensors or biofluid collection structures supported by the functional substrate; wherein the functional substrate provides for microfluidic transport of the biofluid including transport of a first portion of the biofluid to the one or more sensors or biofluid collection structures and transport of a second portion of the biofluid away from the device; (2) contacting the functional substrate of the device with a surface of the skin of a subject; and (3) sampling the biofluid from the surface of the skin of the subject.

As will be understood by one of skill in the art, any of the devices, device components and device features described herein can be used in the present methods. In an embodiment, for example, the biofluid is sweat in a method of the invention. In an embodiment, for example, the method determines a temporal characteristic of the sweat. In an embodiment, for example, the method determines a compositional characteristic of the sweat.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
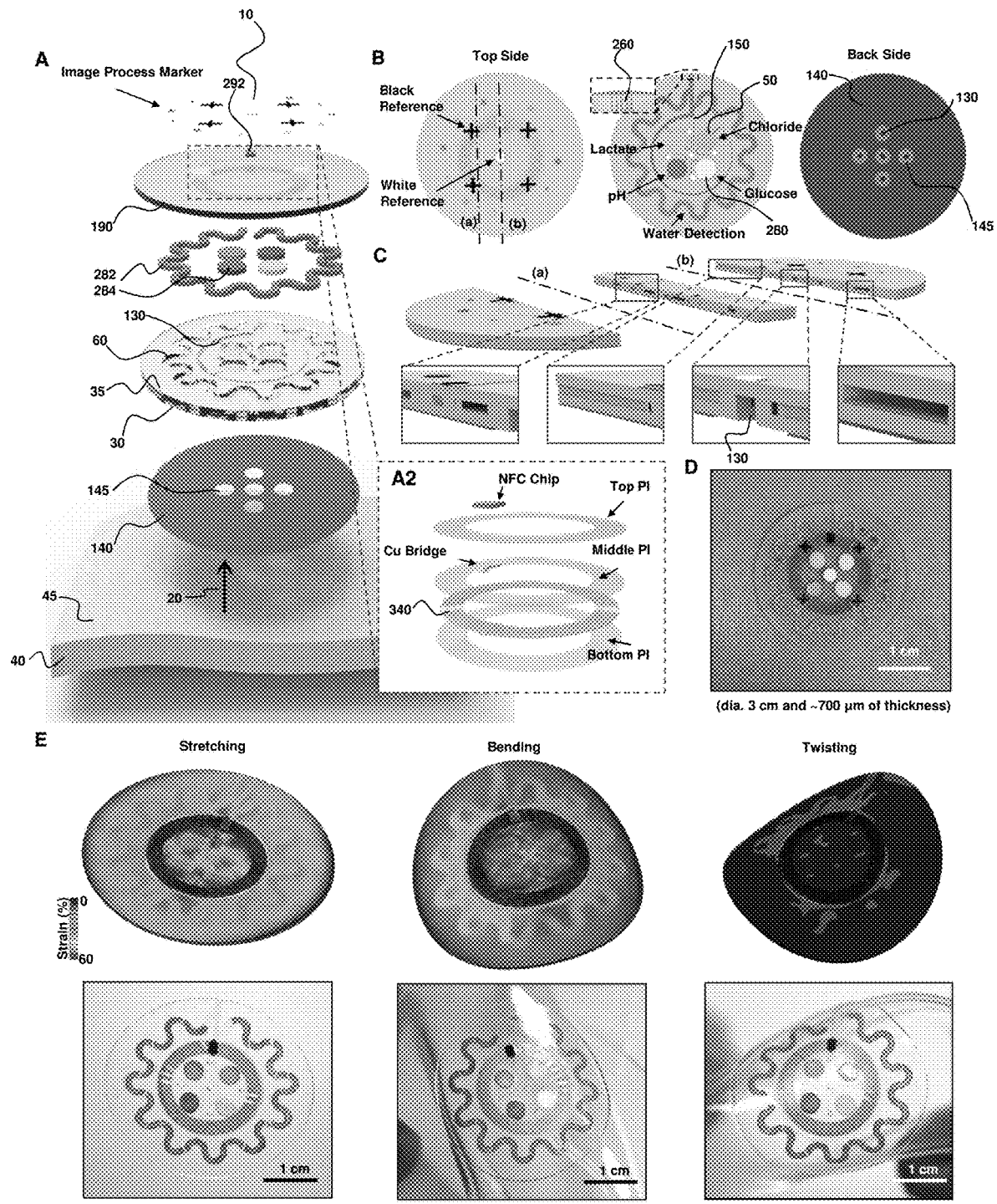
FIG. 1. Schematics, optical images, and theoretical stress modeling of an epidermal microfluidic biosensor integrated with flexible electronics for sweat monitoring. (A) Schematic illustration of an epidermal microfluidic sweat monitoring device and an enlarged image of the integrated near-field communication (NFC) system (panel A2). (B) Illustration of the top, middle, and back sides of a device. The reference color (white and black) markers are on the top side, along with the NFC electronics. The microfluidic channels with colorimetric assay reagents (water, lactate, chloride, glucose, and pH) are in the middle. The bottom side consists of a uniform layer of adhesive bonded to the bottom surfaces of the PDMS-enclosed microchannels with openings that define sweat access and openings that connect to these channels. (C) Cross-sectional diagrams of the cuts defined by the dashed lines (a) and (b) shown in the top side illustration in (B). (D) Optical image of a fabricated epidermal microfluidic sensor (E) Calculated finite element analysis (FEA) results of stress distribution on the devices on phantom skin (PDMS) and respective optical images under various mechanical distortions: stretching at 30% strain, bending with 5 cm radius, and twisting with skin.

In general, the terms and phrases used herein have their art-recognized meaning, which can be found by reference to standard texts, journal references and contexts known to those skilled in the art. The following definitions are provided to clarify their specific use in the context of the invention.

"Functional substrate" refers to a substrate component for a device having at least one function or purpose other than providing mechanical support for a component(s) disposed on or within the substrate. In an embodiment, a functional substrate has at least one skin-related function or purpose. In an embodiment, a functional substrate of the present devices and methods exhibits a microfluidic functionality, such as providing transport of a bodily fluid through or within the substrate, for example via spontaneous capillary action or via an active actuation modality (e.g. pump, etc.). In an embodiment, a functional substrate has a mechanical functionality, for example, providing physical and mechanical properties for establishing conformal contact at the interface with a tissue, such as skin. In an embodiment, a functional substrate has a thermal functionality, for example, providing a thermal loading or mass small enough so as to avoid interference with measurement and/or characterization of a physiological parameter, such as the composition and amount of a biological fluid. In an embodiment, a functional substrate of the present devices and method is biocompatible and/or bioinert. In an embodiment, a functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another.

In some embodiments, a functional substrate that is mechanically matched to a tissue, such as skin, provides a conformable interface, for example, useful for establishing conformal contact with the surface of the tissue. Devices and methods of certain embodiments incorporate mechanically functional substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched functional substrate is characterized by one or more mechanical properties and/or physical properties that are within a specified factor of the same parameter for an epidermal layer of the skin, such as a factor of 10 or a factor of 2. In an embodiment, for example, a functional substrate has a Young's Modulus or thickness that is within a factor of 20, or optionally for some applications within a factor of 10, or optionally for some applications within a factor of 2, of a tissue, such as an epidermal layer of the skin, at the interface with a device of the present invention. In an embodiment, a mechanically matched functional substrate may have a mass or modulus that is equal to or lower than that of skin.

In some embodiments, a functional substrate that is thermally matched to skin has a thermal mass small enough that deployment of the device does not result in a thermal load on the tissue, such as skin, or small enough so as not to impact measurement and/or characterization of a physiological parameter, such as a characteristic of a biological fluid (e.g. composition, rate of release, etc.). In some embodiments, for example, a functional substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a functional substrate that is thermally matched to skin has a thermal mass low enough that it does not significantly disrupt water loss from the skin, such as avoiding a change in water loss by a factor of 1.2 or greater. Therefore, the device does not substantially induce sweating or significantly disrupt transdermal water loss from the skin.

In an embodiment, the functional substrate may be at least partially hydrophilic and/or at least partially hydrophobic.

In an embodiment, the functional substrate may have a modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements. In the context of communications, actuating may refer to a NFC chip useful in providing communication capability to and/or from the electronics portion of any of the devices provided herein.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by, or embedded in, one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin, polydimethylsiloxane, polysodiumacrylate or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a useful contour profile, for example a contour profile allowing for conformal contact with a surface having surface features, e.g. relief or recessed features. In certain embodiments, a desired contour profile is that of skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa. In some embodiments, the functional substrate is a low modulus material, such as a low modulus elastomer.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The invention can be further understood by the following non-limiting examples.

Example 1: Soft, Wearable Microfluidic Systems Capable of Capture, Storage, and Colorimetric Sensing of Sweat Capabilities in health monitoring via capture and quantitative chemical analysis of sweat could complement, or potentially obviate the need for, approaches based on sporadic assessment of blood samples. Established sweat monitoring technologies use simple fabric swatches and are limited to basic analysis in controlled laboratory or hospital settings. Here, we present a collection of materials and device designs for soft, flexible and stretchable microfluidic systems, including embodiments that integrate wireless communication electronics, which can intimately and robustly bond to the surface of skin without chemical or mechanical irritation. This integration defines an access point for a small set of sweat glands such that perspiration spontaneously initiates routing of sweat through a microfluidic network and set of reservoirs. Embedded chemical analyses respond in colorimetric fashion to markers such as chloride and hydronium ions, glucose and lactate. Wireless interfaces to digital image capture hardware serve as a means for quantitation. Two separate human studies demonstrated functionality of this microfluidic device in different subjects during indoor fitness cycling in a controlled environment, and also during long distance bicycle racing in arid and complex conditions. The results include quantitative values for sweat rate, total sweat loss, pH and concentration of both chloride and lactate.

A convergence of advances in materials, new concepts in mechanics design, and specialized device architectures, is beginning to establish the foundation for the next generation of wearable electronic technologies, where sensors and other functional components reside, not in conventional rigid packages mounted on straps or bands, but instead directly on the skin (1, 2). Here, we describe constructs that combine soft, low-modulus physical properties and thin layouts allowing robust, non-irritating, and long-lived interfaces with human epidermis (2). This developing field involves innovative ideas in both organic and inorganic functional materials, where mechanical and manufacturing science play important roles. Although most devices described in the literature focus on measurement of physical characteristics such as motion, strain, stiffness, temperature, thermal conductivity, biopotential, electrical impedance, and related parameters (1, 3-10), complementary information—often with high clinical value—could be realized through capture and biochemical analysis of biofluids such as sweat (11, 12).

As a representative biofluid, sweat is of particular interest owing to its relative ease of non-invasive collection and its rich content of important biomarkers including electrolytes, small molecules, and proteins (13, 14). Despite the importance of sweat analysis in biomedicine, interpreting information from sweat can be difficult due to uncertainties in its relationship with other biofluids, such as interstitial fluid and blood, and due to the lack of biomedical appliances for direct sampling and detection of multiple biomarkers without evaporation (15). In situ quantitative analysis of sweat is therefore of great interest for monitoring of physiologic health status (e.g., hydration state) and for the diagnosis of disease (e.g., cystic fibrosis) (16, 17). Existing systems for whole-body sweat collection have been confined to the laboratory (18), where standard chemical analysis technologies (chromatography, mass spectroscopy, electrochemical detection) can reveal the composition of collected samples (19). Recent attempts to detect and collect sweat simultaneously have focused on direct contact of sensors on the skin (e.g., temporary tattoo) or use of fabric or paper substrates to accumulate sweat for electrochemical and/or optical assessment (20). For instance, electrochemical sensors directly laminated on the epidermis can detect chemical components, such as sodium ions and lactate, in real-time (21-23). Colorimetric responses in functionalized porous substrates can yield chemical information, such as the pH of sweat, and further enable simple quantitative assays using devices capable of capturing high-quality digital images, such as smartphones (24-26). Radio frequency identification (RFID) systems, which can be integrated on top of porous materials for wireless information transfer, provide additional functionality (27, 28). These and related technologies have come together to quantify sweat generation rate (27), but because the sweat gland density is not known, the total sweat rate and volumetric loss cannot be determined accurately in conventional technologies. Additionally, the formats do not simultaneously reveal the concentration of multiple chemical components, nor do they offer full compatibility with the growing availability in soft, skin-mounted electronics, physical sensors, radio technologies, and energy storage devices.

Here, we report a type of thin and soft, closed microfluidic system that can directly and reliably harvest sweat from pores on the surface of the skin. The device routes this sweat to different channels and reservoirs for multi-parametric sensing of markers of interest, with the option to wirelessly interface with external devices for image capture and analysis. This type of microfluidic technology includes fluid handling, fluid capture, and biochemical analytical capabilities. The devices could be mounted at multiple locations on the body without chemical or physical irritation by biocompatible adhesives and device mechanics, and formed flexible and stretchable, water-tight interfaces. These devices were able to measure total sweat loss, pH, lactate, chloride, and glucose concentrations by colorimetric detection using wireless data transmission. We tested these devices in two human studies: a controlled, indoor, mild sweat inducing study; and a "real world", outdoor use study conducted during a long distance bicycling race.

Materials and Methods: Study design: The objectives of indoor and outdoor human trial studies were to investigate feasibility of using these epidermal microfluidics devices in practical scenarios under controlled and uncontrolled environmental conditions and during moderate and vigorous exercise. Nine subjects were recruited through the Clinical Research Laboratory, LLC for indoor studies with anonymous collection of information including date of birth, gender, contraceptive status, weight, height, body mass index (BMI), blood pressure, and information from a simple survey of medical condition to ensure all subjects were healthy. The experimental conditions, including temperature, humidity, time course of application of device, and weight of absorbing Webril pads for sweat collection were all controlled and/or documented. Results obtained from image analysis methods (described in the section "Near-field communication and image processing for quantitative analysis") were compared with those from chemical laboratory analysis. For the outdoor study, twelve healthy subjects volunteered under eligibility requirements including enrollment and participation in El Tour de Tucson, a 104-km bike race. Age, height, and weight were recorded from subjects at the start of the race and used to calculate BMI and body surface area (BSA). Environmental conditions including temperature, humidity, and UV index were recorded every 2-3 hours from information provided by the National Weather Service. In both studies, sweat patches were placed on two different geographical body areas (volar arm and lower back) and image data were obtained by smartphone and digital single-lens reflex (DSLR) cameras.

Fabrication of epidermal microfluidic devices with integrated electronics for colorimetric sweat analysis: Standard soft lithographic techniques enabled fabrication of epidermal microfluidic devices (56). Briefly, casting and curing PDMS against lithographically prepared molds yielded solid elastomers with features of relief on their surfaces. Bonding separate pieces of PDMS formed in this manner defined sealed microfluidic channels and containment reservoirs. Mechanical punches created openings to define the inlets for sweat collection. A separate, double-sided thin adhesive layer with matching holes bonded to the bottom surface of the device on one side and to the skin on the other. As an option, separately fabricated thin electronic systems with open architectures were mounted on the top surface. For colorimetric analysis, the chromogenic reagents for detecting glucose, lactate, chloride, and pH were spotted onto filter paper and inserted into containment reservoirs. Cobalt chloride dissolved in pHEMA hydrogel was added to serpentine channels. Complete fabrication and colorimetric analysis details are provided herein.

Figure 23:
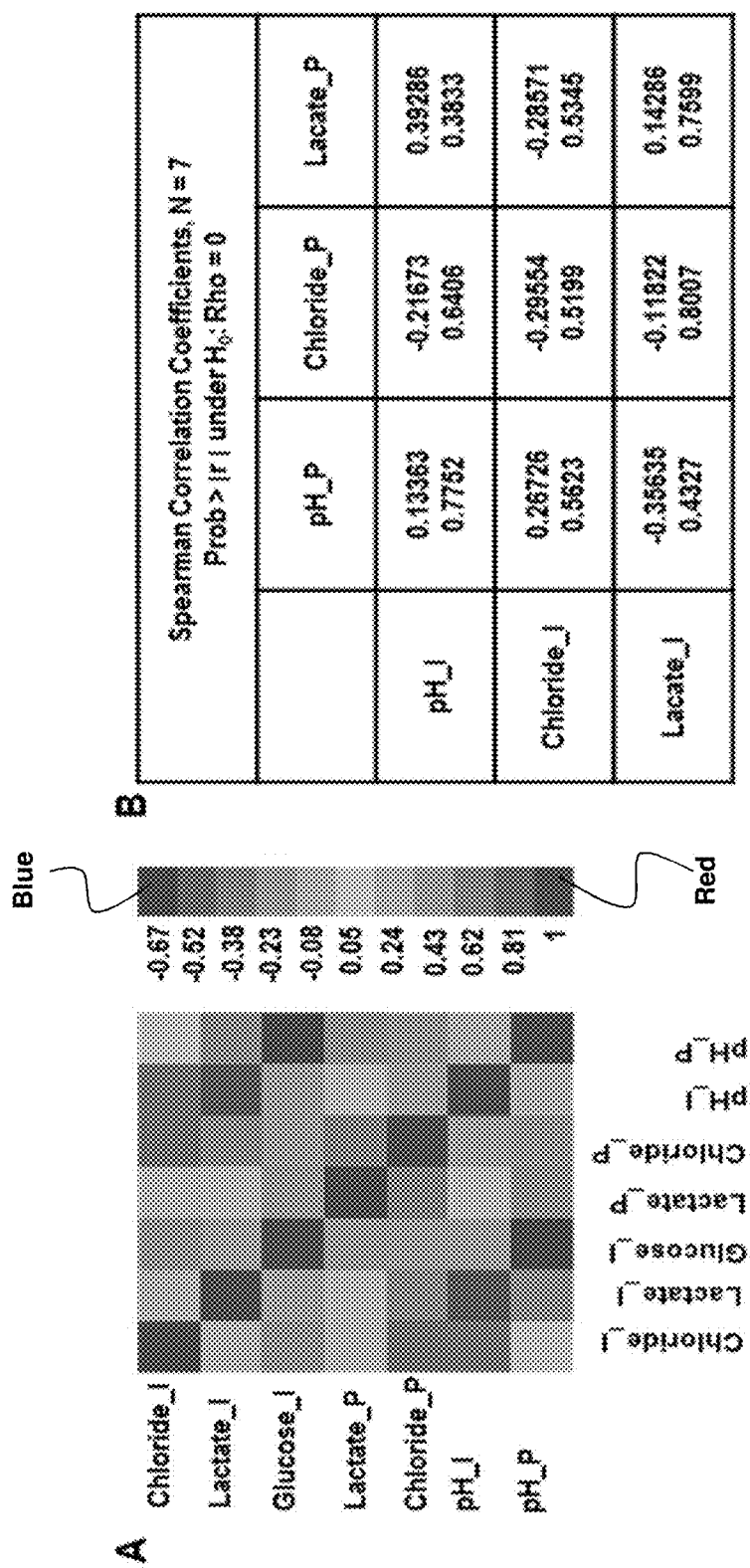
FIG. 23. Multivariate statistical analysis for correlations in biomarker concentrations between patch (p) and lab (l) analysis. (A) Pearson correlation map. (B) Spearman rank-order statistic.

Statistical analysis: Data are presented with average values and standard deviations (SD) unless noted in the figure caption. Significant difference was calculated based on the two-tailed t-test. Pearson and Spearman correlation analyses were conducted on the patch and laboratory results (FIG. 23). The matrix of bivariate correlations in analyte concentrations between the patch and lab analysis are displayed using a heat map representation. Blue and red denote negative and positive correlations, respectively. Bivariate correlations are described using Spearman rank-order statistics. Analyses were performed using SAS and JMP statistical software.

Figure 7:
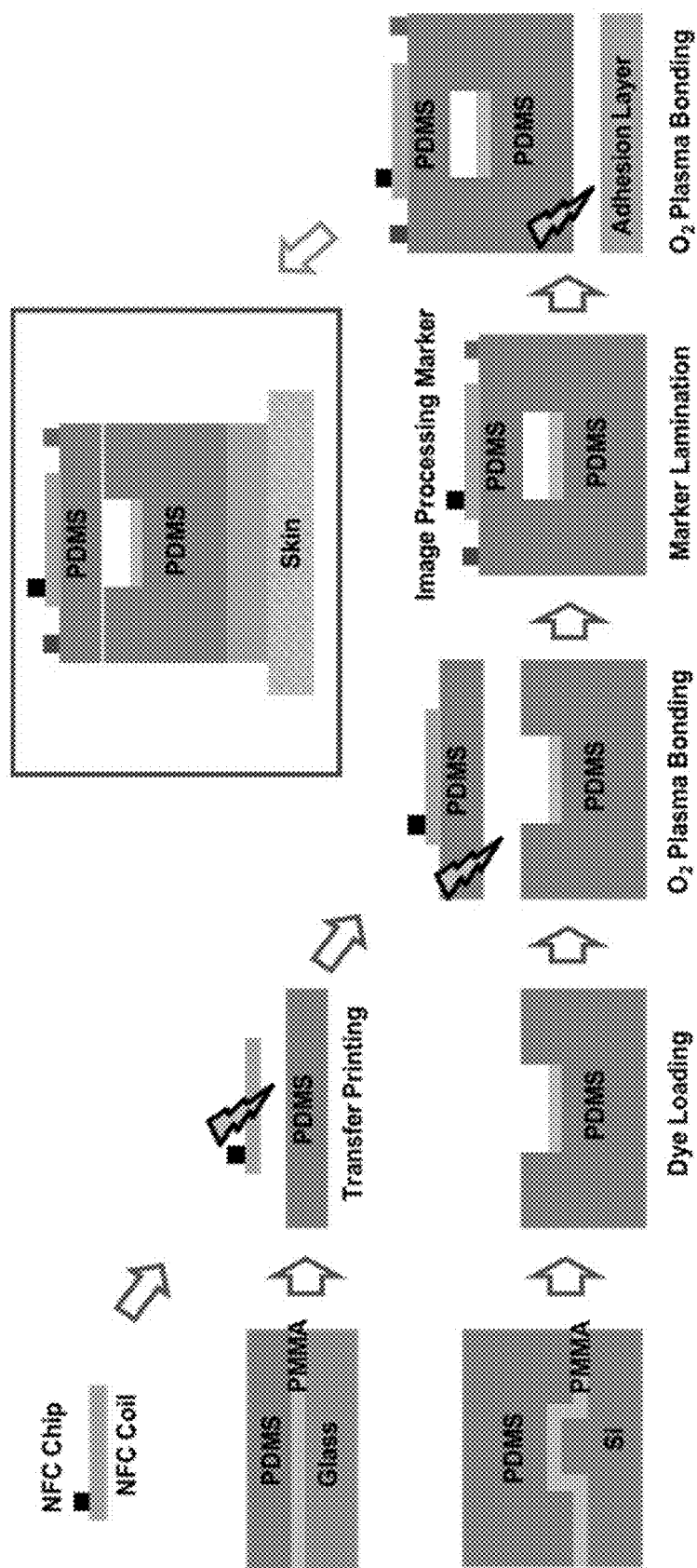

Soft epidermal microfluidics for sweat monitoring: The soft, epidermal microfluidic device that we have developed adheres and conforms to the skin in a manner that captures and routes sweat through a network of microchannels and reservoirs—using a combination of capillarity and action of the natural pressure (~70 kPa) associated with perspiration—for volumetric assessment and chemical analysis in situ (13). Low modulus biocompatible materials, soft silicon elastomers (~1 MPa), were created using soft lithography to define the microfluidic constructs (diameter 3 cm and ~700 µm in thickness) (FIG. 1, FIG. 7). The specific designs described can retain ~50 µL of sweat corresponding to an effective working time of 1-6 hours of exercise, depending on the rate of sweat loss and the mounting location on the body (12-120 µL/h/cm$^2$) (32). Stretchable electronics technology allows direct integration of wireless sensing and data transfer capabilities into these platforms.

Figure 8:
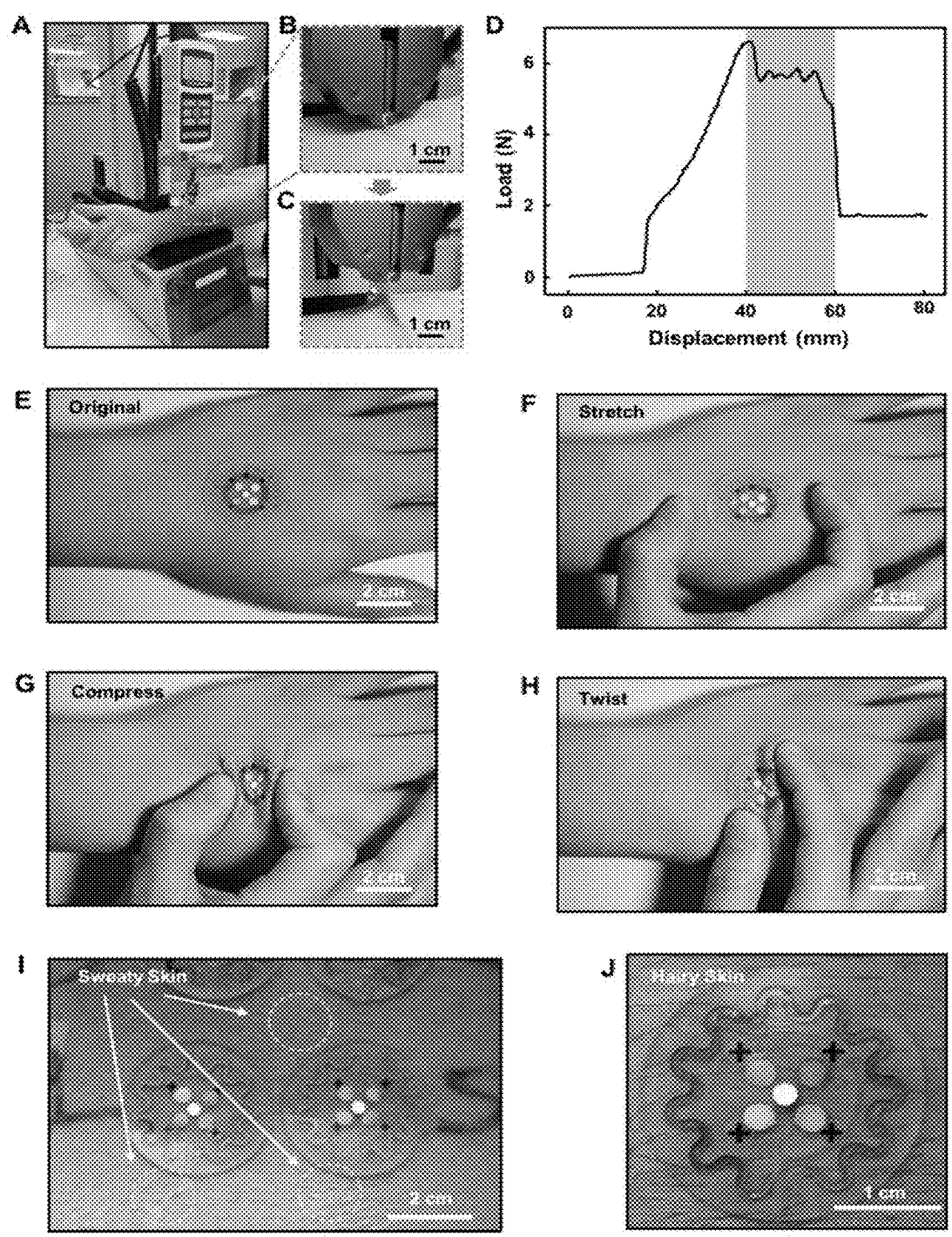
FIG. 8. Determination of adhesion forces and conformal adhesion between device and skin. (A) Experimental set-up for 90° peel adhesion property testing (standard ISO 29862: 2007) using a force gauge (Mark-10, Copiague, NY). Images of (B) holding a device adhered on the skin with force gauge and (C) peeling devices at an angle of 90°. (D) Force measurement while displacing the device at the rate of 300 mm/min indicating the gray region where peeling was occurred. Determined average peeling force was 5.7 N. Sweat patches conformably adhere under various conditions, such as applying (E) no strain, (F) stretching, (G) compressing, and (H) twisting distortions as well as laminating on (I) sweaty and (J) hairy skin.
Figure 9:
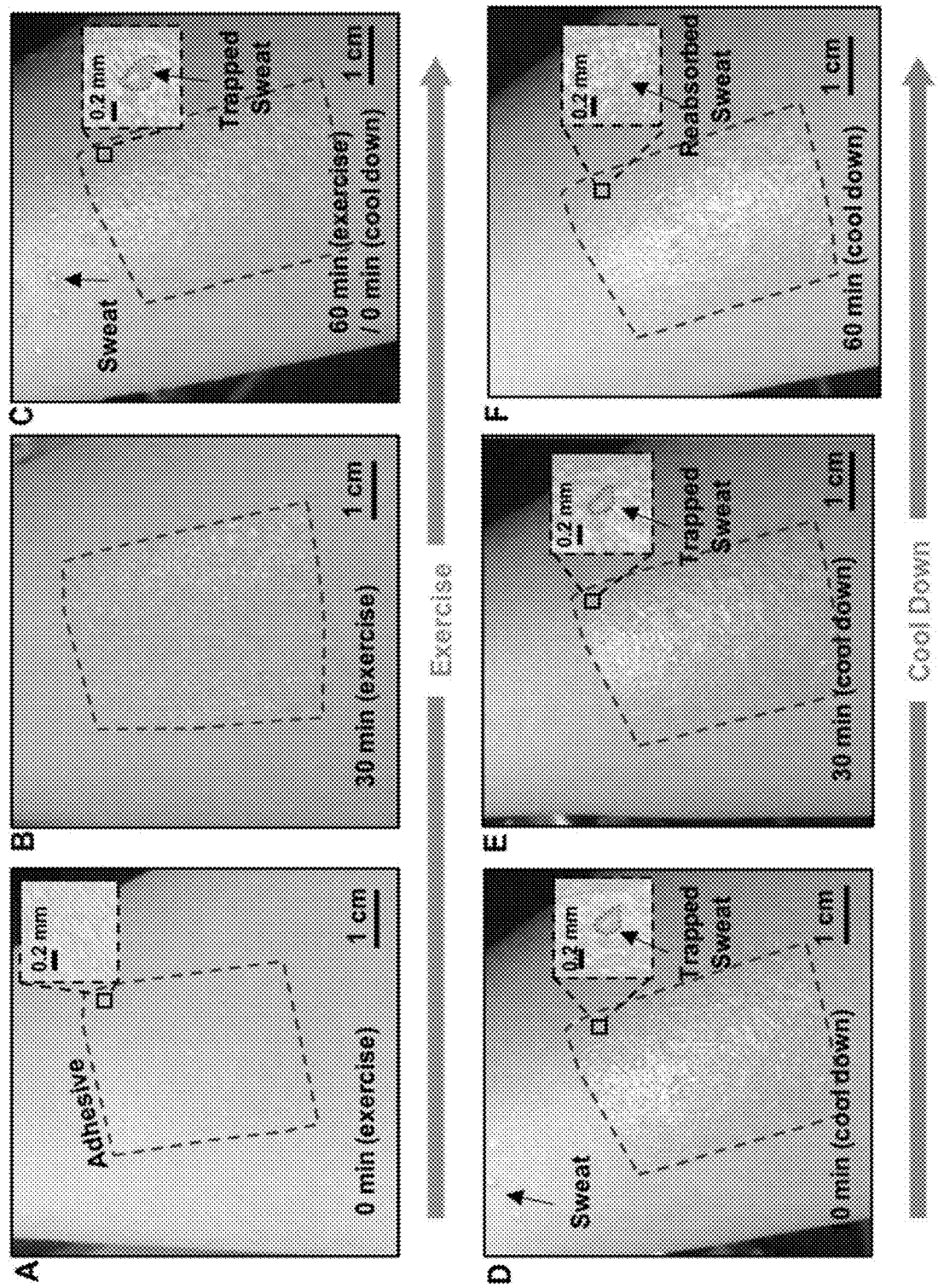
FIG. 9. Observations of sweat at the interface between an adhesive layer and the skin. (A) A picture of a piece of medical adhesive on the skin and (B-C) images of the sweat trapped under the adhesive during exercise. (D-F) Images collected at various times during a resting state immediately after the exercise. The sweat appears in isolated pockets, and gradually reabsorbs into the skin, consistent with negligible lateral flow. The reabsorption rate evaluated from such experiments was ~12 mg/cm$^2$ h, while the moisture vapor transmission rate (MVTR) of the acrylic adhesive is 2.08 mg/cm$^2$ h.

Devices are composed of a multilayer stack of three sub-systems: (1) a skin-compatible adhesive layer with a micromachined opening that defines the area of sweat collection; (2) a sealed collection of soft microfluidic channels and reservoirs filled with color-responsive materials for quantitative analysis of sweat volume and chemistry; and (3) a magnetic loop antenna and associated near-field communication (NFC) electronics for interfacing to external wireless devices (FIG. 1a). A medical-grade acrylic adhesive film ensured stable, strong and seamless adhesion (~5.7 N) of the device to the skin without irritation in a manner that offered compatibility with sweaty or hairy skin (FIG. 8). This adhesive exhibited ~5 times greater adhesion force than the typical medical adhesive Tegaderm (1.02 N) (33). The thin geometry (25 µm) and low modulus (~17 kPa) of this layer provided stress release during deformation of the skin (FIG. 8) facilitating comfort and long-term wearability. An opening defined the sweat harvesting area (3 mm diameter, corresponding to ~10 sweat glands) (34) through which sweat could pass into the inlet region of the overlying soft microfluidic system (FIG. 1b). The pressure that drives fluid flow arises from the action of the sweat glands themselves, assisted by capillary effects in the microchannels and the materials embedded within them. The conformal contact of the adhesive layer inhibited lateral flow of sweat from regions located outside the defined openings, ensuring fluid issuing from the harvesting area dominated the sweat sample (FIG. 9).

The microfluidic system may comprise a bottom polymer layer (e.g., polydimethylsiloxane (PDMS)), such as having a 500 µm thickness, embossed with desired relief geometry to provide a microfluidic network, such as a uniform depth of 300 µm and filled with reagents for colorimetric analysis (FIGS. 1, a and b). A top-capping layer of PDMS served as a seal (200 µm thick). One layout includes four chambers (such as circular chambers having a diameter of about 4 mm) as independent reservoirs for analysis, preventing any crosstalk, that are surrounded at the outer perimeter by an orbicular serpentine channel. This channel and each of the reservoirs are connected by separate guiding channels to the hole segments (diameter 0.5 mm) that spatially align with the openings (diameter 3 mm) in the skin adhesive layer (FIGS. 1, b and c). To avoid backpressure that can impede fluid flow, all channels and reservoirs may interface to an outlet microfluidic channel (100 µm width) that terminates on the top-side edge of the device (FIG. 1b). Quantitative colorimetric assay reagents in the circular reservoirs in the middle of the device facilitates assessment of pH and the concentration of selected essential markers, including glucose, lactate, and chloride, through either enzymatic or chromogenic reactions. As such, with the exception of pH, the colorimetric schemes embedded in the current devices do not afford real-time tracking of changes in analyte concentration. A water-responsive chromogenic reagent in the serpentine channel allows determination of the extent of filling with sweat, which can be converted to overall sweat rate and volume.

Figure 10:
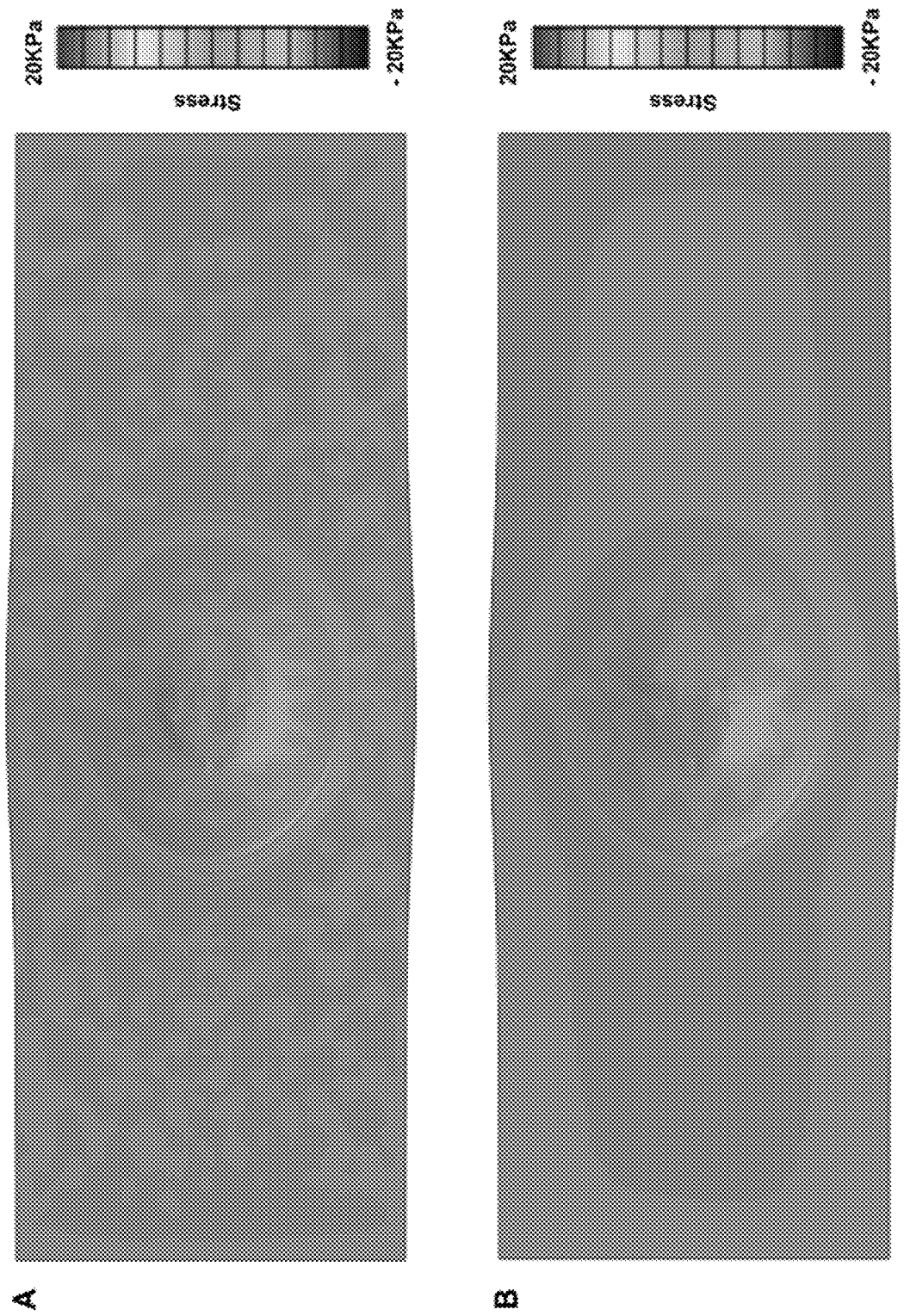
FIG. 10. Normal (A) and shear (B) stress distribution at device/skin interface under 30% stretch plotted on deformed skin.

Specially formulated variants of PDMS offer physical characteristics that are attractive for this application, including optical transparency, ease of patterning into microfluidic systems, biocompatibility, and favorable mechanics (low modulus, ~145 kPa; high elasticity, up to ~200% strain at break) (35). The soft mechanics and thin geometry enabled soft, non-irritating intimate contact with the skin through principles similar to those established for epidermal electronics (2, 36). The finite element analysis (FEA) results of strain/stress distributions and corresponding optical images in FIG. 1e show deformation of a representative device under various mechanical distortions with a phantom skin (a PDMS substrate exhibiting similar mechanical properties to skin). The maximum normal and shear stresses at the device/phantom skin interface were far below the threshold for somatosensory perception of forces (20 kPa) during ~30% stretch (37) (FIG. 10). Fabricated elastomeric microfluidic devices exhibited ~0.16 MPa of effective modulus, comparable to real skin and previously reported epidermal devices (37, 38).

Figure 11:
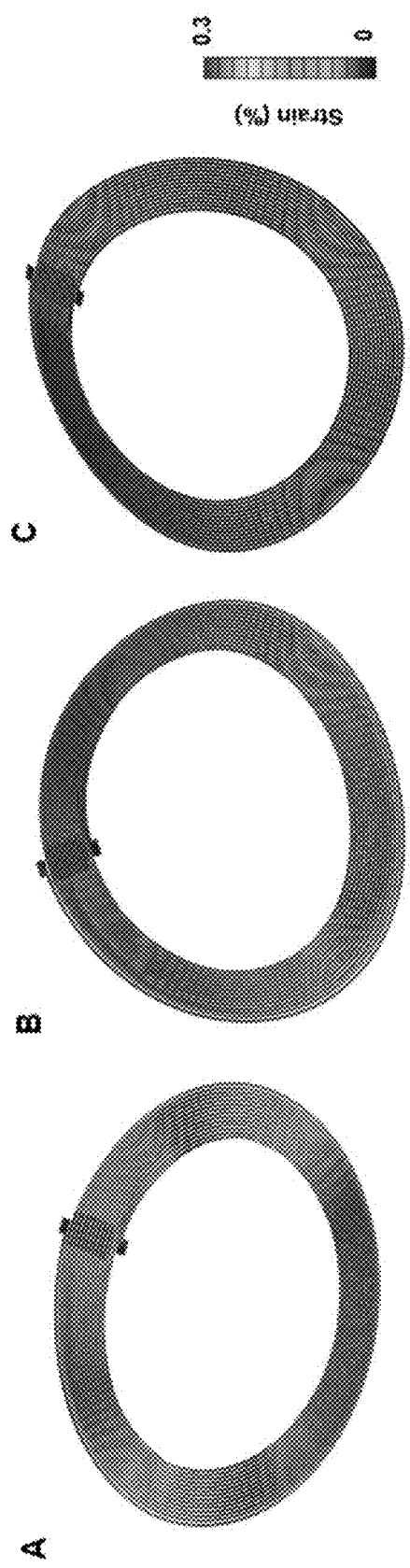
FIG. 11. Mechanical modeling results for NFC electronics. (A) Stretching, (B) bending, and (C) twisting deformations.
Figure 12:
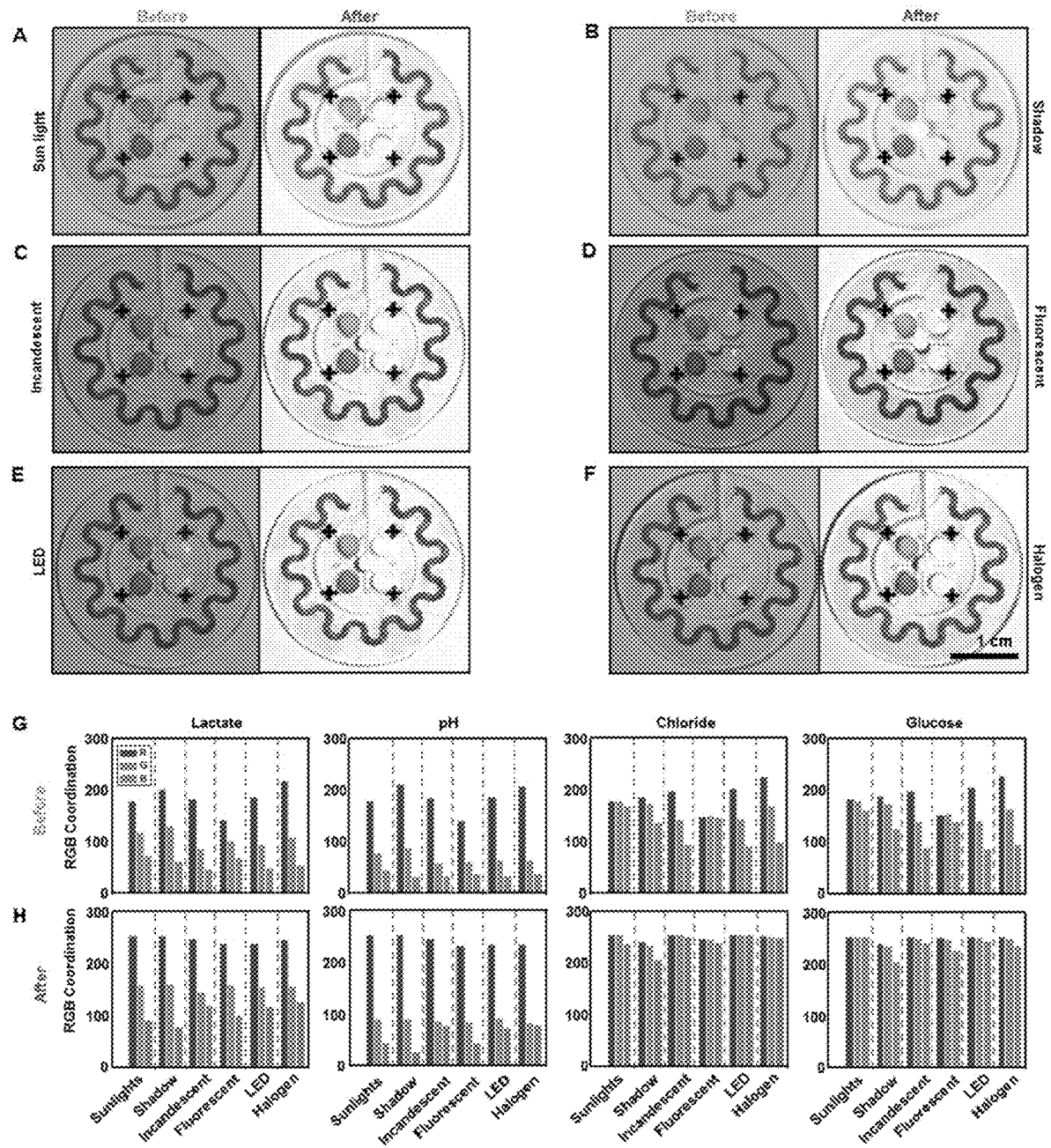
FIG. 12. Color balancing performed by internal calibration makers (black crosses and white circle) under various light conditions (A-F) and changes in numeric RGB representation obtained by respective images (G) before and (H) after white balance. Images before (left) and after (right) color calibration performed under various light conditions, including (A) sun light, (B) shadow, (C) incandescent, (D) fluorescence, (E) LED, and (F) halogen bulb light.
Figure 13:
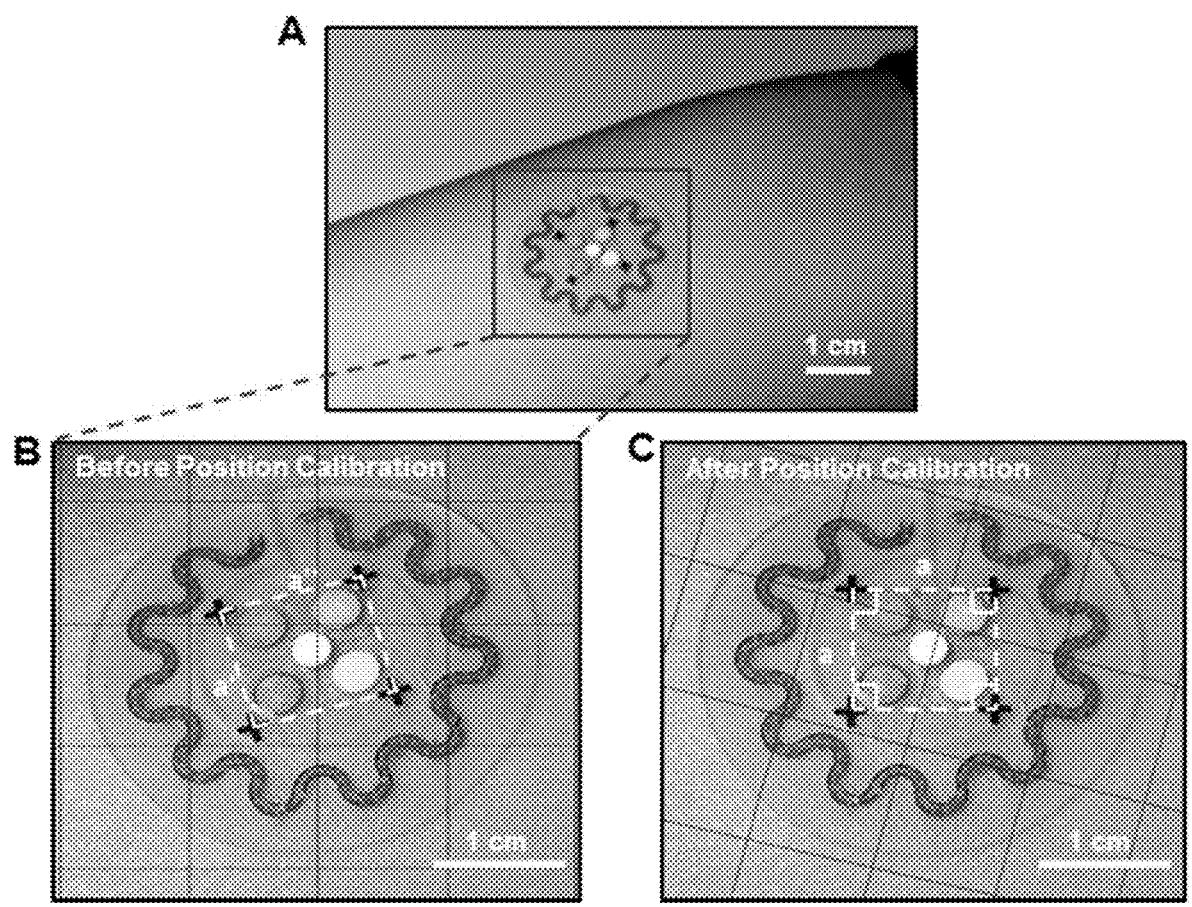
FIG. 13. Image processing for position calibration. (A) Original image and magnified images (B) before and (C) after position calibration.

Integrated electronics allow wireless interfaces to external computing and digital analysis systems using common platforms such as the smartphone. Our technology capitalized on NFC schemes to launch image capture and analysis software on such an external device, and/or to read temperature from an integrated sensor. The overall designs allowed stretchable electronics to operate under physical deformation without significantly altering the mechanical properties of the soft microfluidic system. Finite element analysis (FEA) results demonstrated that the maximum strain in the copper layer was below the elastic limit (0.3%) under all loading conditions (FIG. 11) (39). Reference marks on the top of the device platform (FIG. 1b) included a white dot and black crosses for color balancing to allow accurate color extraction under arbitrary lighting condition (FIG. 12). The crosses also helped determine the position and orientation from the images (FIG. 13).

Figure 14:
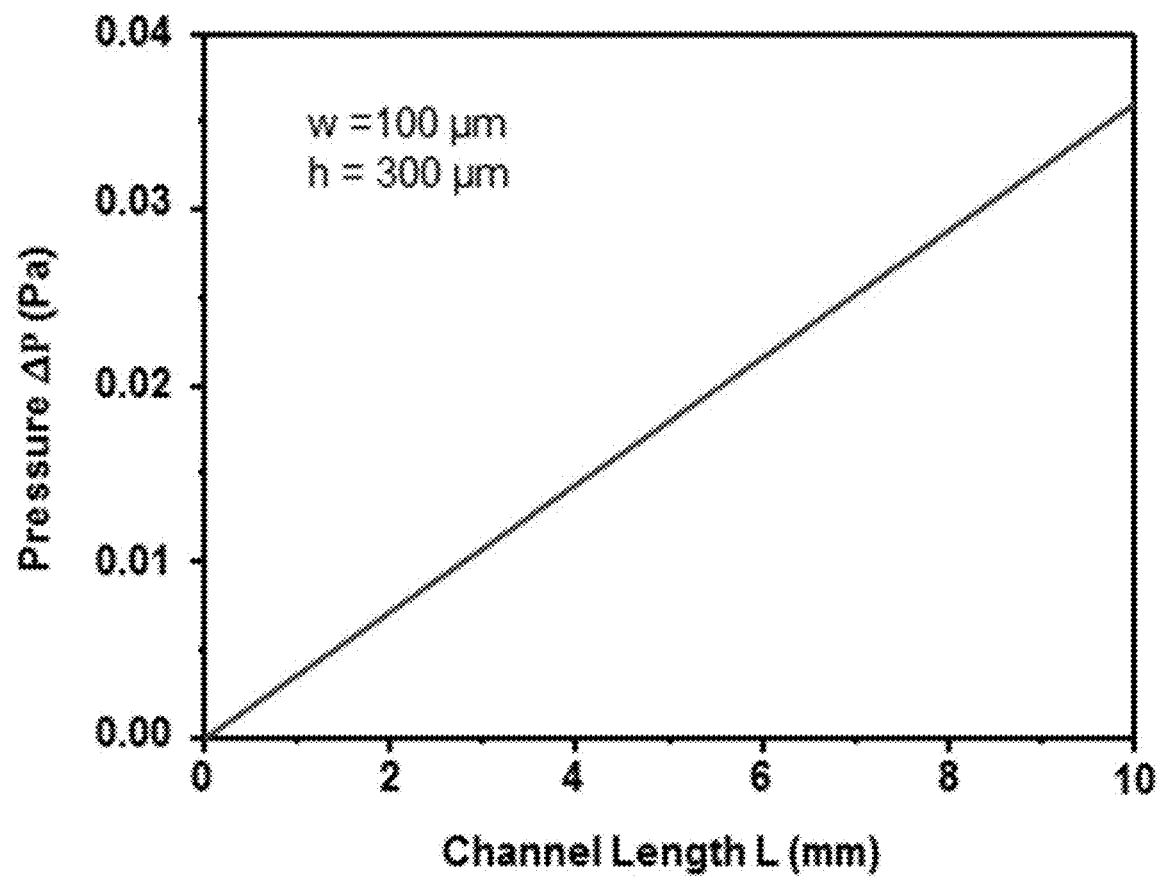
FIG. 14. Calculation of the inner pressure as a function of the outlet channel length.

Soft epidermal microfluidics for sweat monitoring: We optimized materials and channel design to adequately collect sweat in situ, with soft, stretchable mechanics that offer high structure stability, low vapor permeability, and minimal backpressure (flow impedance into the channel). FIG. 2a is a sketch of the channel geometry, representing the area of the outlet and the serpentine channel, used for theoretical calculation of the essential mechanics and flow properties. The blue and red dashed boxes highlight the dimensions of the serpentine and outlet channels, respectively. The outlet channels relieve backpressure. The outlet channels may yield some sweat loss as water (sweat) vapor. The water vapor loss showed little dependence on the length of outlet channel while backpressure was linearly proportional to this length according to calculations for a model system (FIG. 14 and FIG. 2b). A short outlet channel length of 2.5 mm was chosen to minimize backpressure. Our calculations further indicated that the vapor loss with 100 µm wide channels was ~3.2-fold lower than with 800 µm wide channels, while 25 µm wide channels differed only ~1.1-fold from the 100 µm wide channels (FIG. 2b). In the range of widths under 100 µm, backpressure notably increased and bending deformation of the device was obstructed with negligible effects on vapor loss. Considering calculated values and practical resolution limits of soft lithography, optimized outlet channel dimensions of 100 µm in width and 2.5 mm in length were selected.

Figure 15:
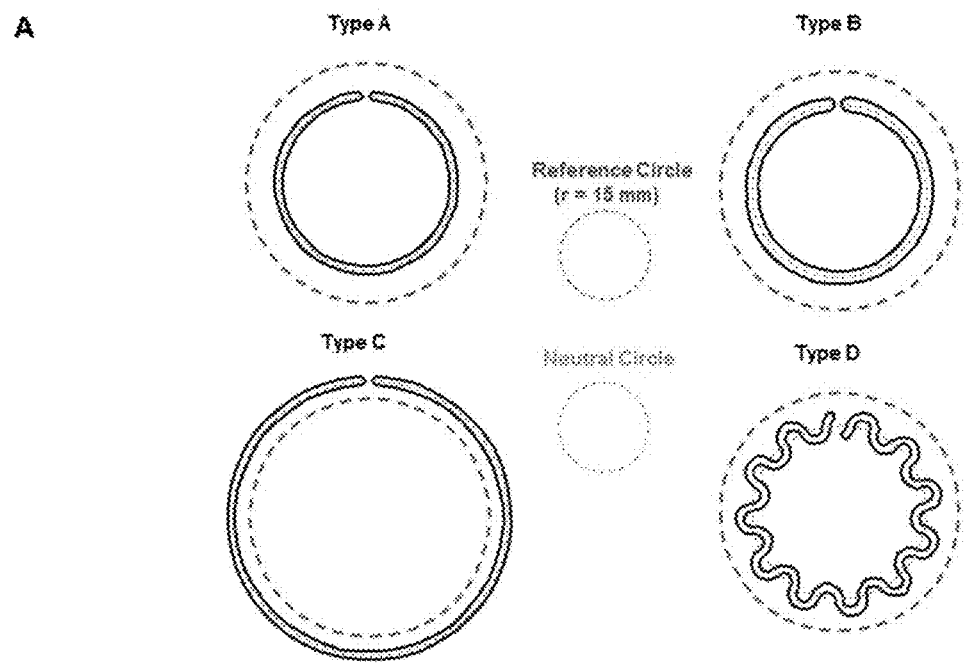
FIG. 15. Strategies and optimization of the orbicular channel design. (A) Illustration of four different types of channel designs. Red broken lines represent a reference circle (r=15 mm) that corresponds to the outer edge of the sweat patch. Blue broken lines show neural circles of various designs of orbicular channels. (B) A comparative table showing quantitative values for each channel design.

As with vapor loss and backpressure, stretchability and structural stability are two other competing issues that demand careful optimization. Although thin geometries and low modulus elastomer are key to achieving mechanical compatibility with the skin, such characteristics may also yield substantial deformation or even collapse of the channel under external pressure (40), in the as-fabricated form or in states induced by natural deformations of the skin. Modeling yielded predictions for percentage changes in the volume of the serpentine channel associated with externally applied pressures between 100 and 400 Pa (FIG. 2c) comparable to those that might be associated with a gentle touch by a fingertip (41). The volume change increased the aspect ratio (AR, width to height). For example, the volume change for AR 5 (1.5 mm width and 300 µm height) was ~5-fold greater than that for AR 3.3 (1.0 mm width and 300 µm height). Because the channel also needs to consider the total volume of sweat that can be captured and the overall size of the device, we chose the lower limit AR 3.3 for the channel design. Additionally, serpentine channel layouts provided a convenient means to increase the total channel volume for a given device size (FIG. 15). All of these optimizations led to the overall design, the cross-sectional channel, and the outlet shapes illustrated in FIG. 2d.

Figure 16:
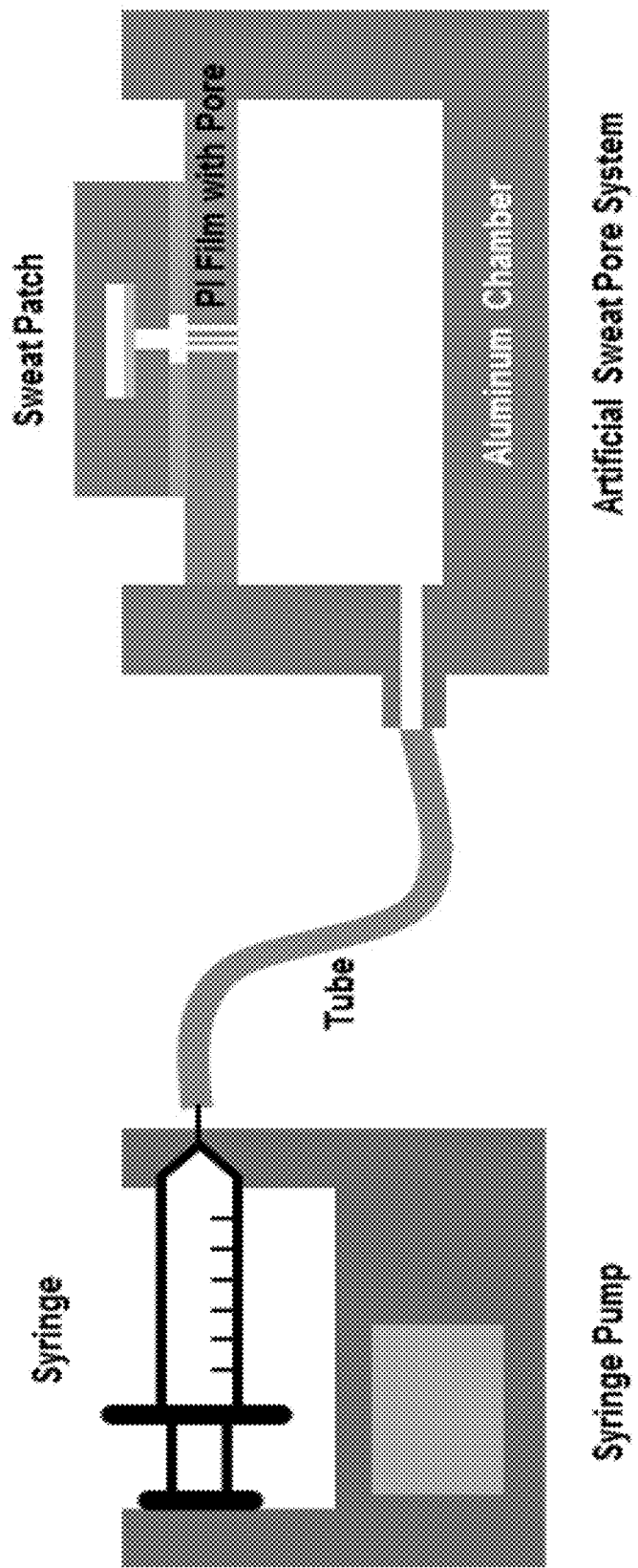
FIG. 16. Schematic illustration of the artificial sweat pore system.

Microfluidic sweat capture and quantitative colorimetric analysis: Quantitative in vitro testing of microfluidic performance first involved a simple, artificial sweat pore system (FIGS. 2e and f, and FIG. 16) to mimic human eccrine sweat glands (42), consisting of a perforated polyimide (PI) membrane (pores with diameter 60 μm, ~100 pores/cm$^2$) mounted in a fixture with an underlying fluid reservoir connected to a syringe pump. A device (0.07 cm$^2$ of harvesting surface area) laminated on the perforated membrane captured dyed water pumped at 5.5 μL/hour (FIG. 2g), demonstrating the first step in quantitative analysis of liquid uptake. The experimentally determined harvested liquid volume in the channel is consistent with the input volume introduced by the syringe pump, is consistent with linear hydrodynamic flow in the microfluidic channel, showed negligible loss of water vapor, and no fluid leakage under these conditions.

In terms of device design, three factors determine the time resolution: (1) the rate of fluid flow into the reservoirs and the serpentine channel; (2) the harvesting area; and (3) the time and spatial resolution of the camera system and image analysis software. For the device layout with harvesting area (~10 mm$^2$), the human studies presented subsequently showed volumetric sweat harvesting rates of ~1.2-12 μL/h, corresponding to linear filling rates of ~0.07-0.7 mm/min along the serpentine channels. The reservoirs would fill within ~0.3-3.2 hours at these sweating rates, with time scaling linearly with reservoir volume. Decreasing the cross-sectional area of the channel would increase the filling rate proportionally. For image capture once every 5 minutes, a spatial resolution of ~0.35-3.5 mm can easily resolve changes in the positions of the fluid fronts, providing 12 data points within the ~60 min timeframe, which we considered relevant for changes in sweat chemistry (13).

Figure 17:
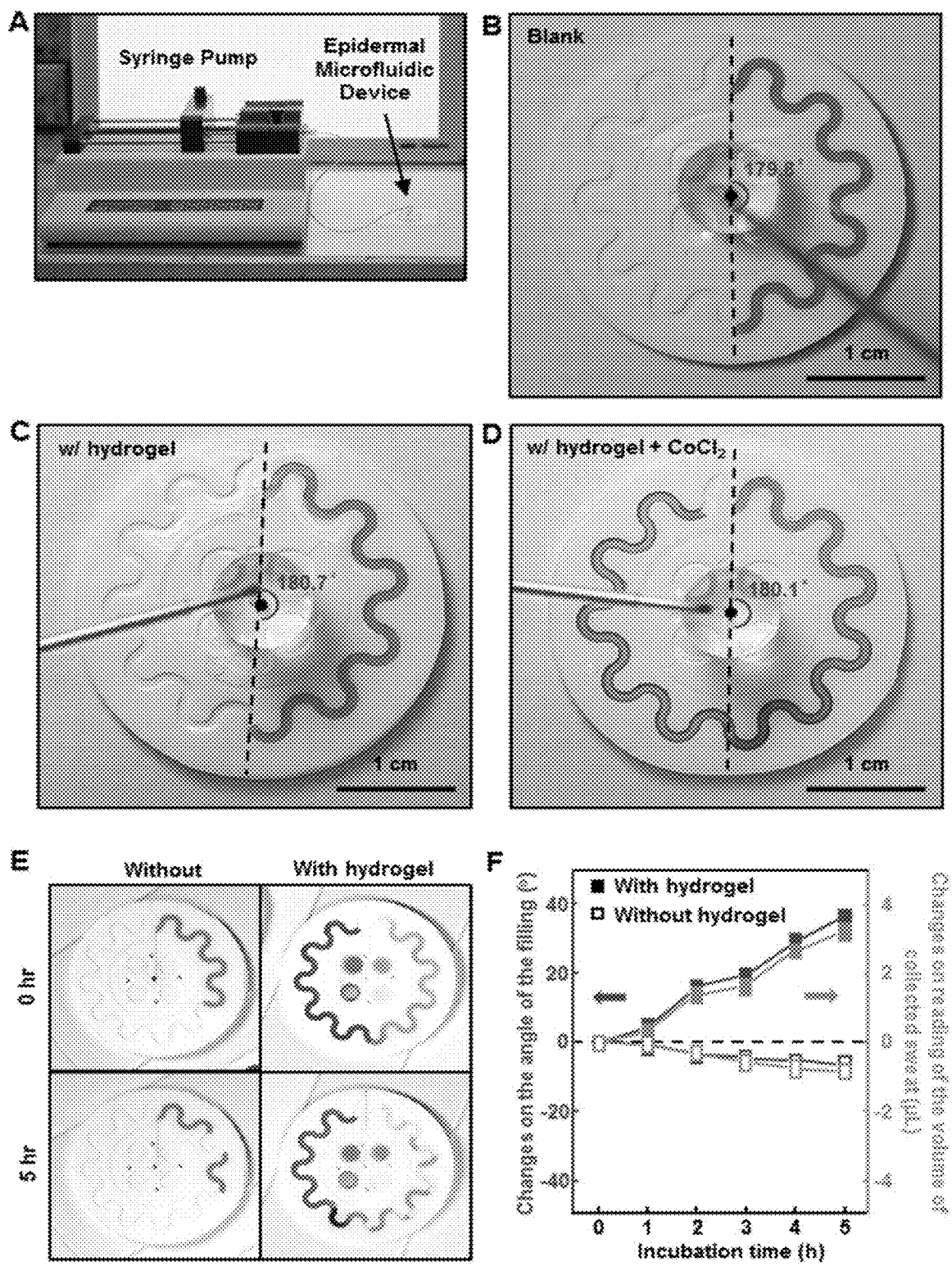
FIG. 17. Hydrodynamic test to verify the influence of the hydrogel matrix on channel volume. (A) Picture of the experimental set-up. A syringe pump introduced 15 μL of water with red dye into the microfluidic device at the rate of 120 μL/hour. Optical images of devices consisting of (B) blank channel and the channels coated (C) without and (D) with $CoCl_2$ embedded in the thin (25 μm) hydrogel matrix. (E) Images of devices with and without hydrogel coatings on the serpentine channel at the certain period incubation time. (E) Angular position of the change in color of the serpentine channel (black) and respective reading of the harvested volume of artificial sweat in the device (blue) as a function of incubation time. (F) Plot of changes on the angle of the filling vs Incubation time (h).
Figure 18:
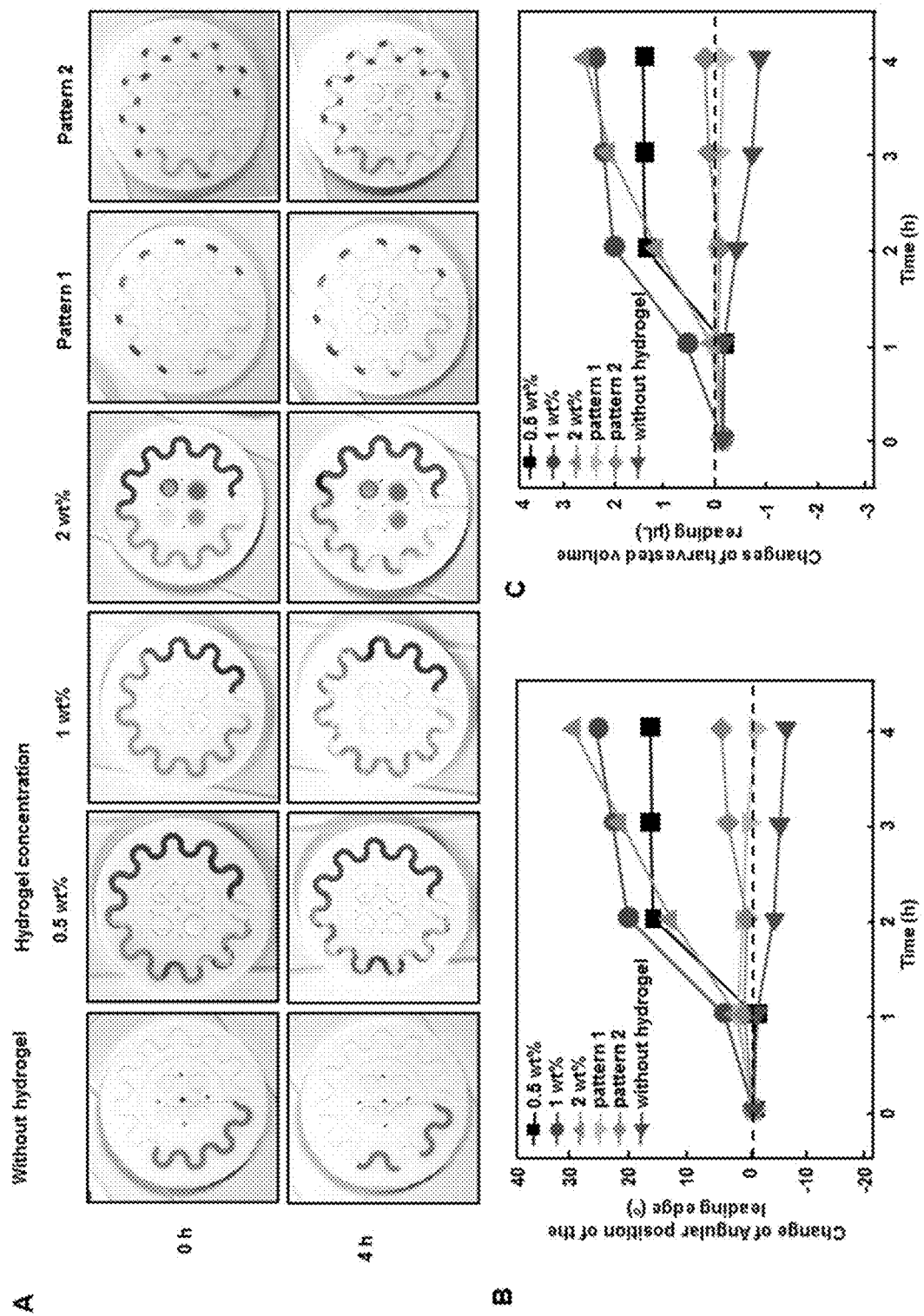
FIG. 18. Assessment of the angular position of the liquid front in partially filled serpentine channels in devices with different hydrogel concentrations and segmented hydrogel patterns. (A) Images of devices at various times after partially filling the serpentine channels. (B) Changes of angular position of the leading edge and (C) respective reading of harvested volume as a function of incubation time for these various cases.

The colorimetric sensing approach allowed simple, rapid quantitative assessment of instantaneous rate and total volume and sweat loss, pH, chloride, lactate, and glucose in sweat (FIG. 3a). The first parameters relate to thermal regulation and dehydration, where continuous monitoring yields important information of relevance to electrolyte balance and rehydration (43). In the orbicular serpentine channel, cobalt (II) chloride (i.e., CoCl$_2$) contained in a coating of a polyhydroxyethylmethacrylate hydrogel (pHEMA) matrix, served as a colorimetric indicator. As sweat entered the channel, the anhydrous cobalt (II) chloride chelated with water to form hexahydrate cobalt chloride (CoCl$_2$.6H$_2$O), generating a change in color from deep blue ($\lambda_{max}$=657) to pale purple ($\lambda_{max}$=511) (FIG. 3b). The position of the leading edge that defines this color change, along with the dimensional characteristics and geometry of the channel, yields quantitative information on the sweat rate and volume. Owing to the thin layer (~25 μm) coated on the channel wall and the hydrophilic properties of the pHEMA hydrogel matrix, the hydrodynamics of flow within the channel were not influenced during conditions of momentary flow (FIGS. 17 a-d). The sweat could, however, continue to travel slowly through the channel by spontaneous internal flow (0.68 μL/h), with the possibility of a ~2% reading error (FIGS. 17 e and f). This artifact does not occur in channels without the hydrogel; its effect could be determined, for practical purposes, by patterning the hydrogel into short segments (FIG. 18).

Four different paper-based colorimetric chemical assays resided in the central reservoirs. The cellulose matrices in each reservoir could be filled with as little as 5-10 μL of sweat sample. The color changes occurred on timescales of <1 min. The concentration of lactate in sweat is an indicator of exercise intolerance and tissue hypoxia (44, 45). Enzymatic reactions between lactate and co-factor NAD+ by lactate dehydrogenase and diaphorase induce a change in color of a chromogenic reagent (i.e., Formazan dyes). The formulation of enzyme and dyes in the detection cocktail solution ensured a dynamic range compatible with human sweat. The color change in the detection reservoir correlated with the concentration of lactate throughout the relevant range expected in sweat (1.5-100 mM) (FIG. 3c) (13, 46, 47).

Figure 19:
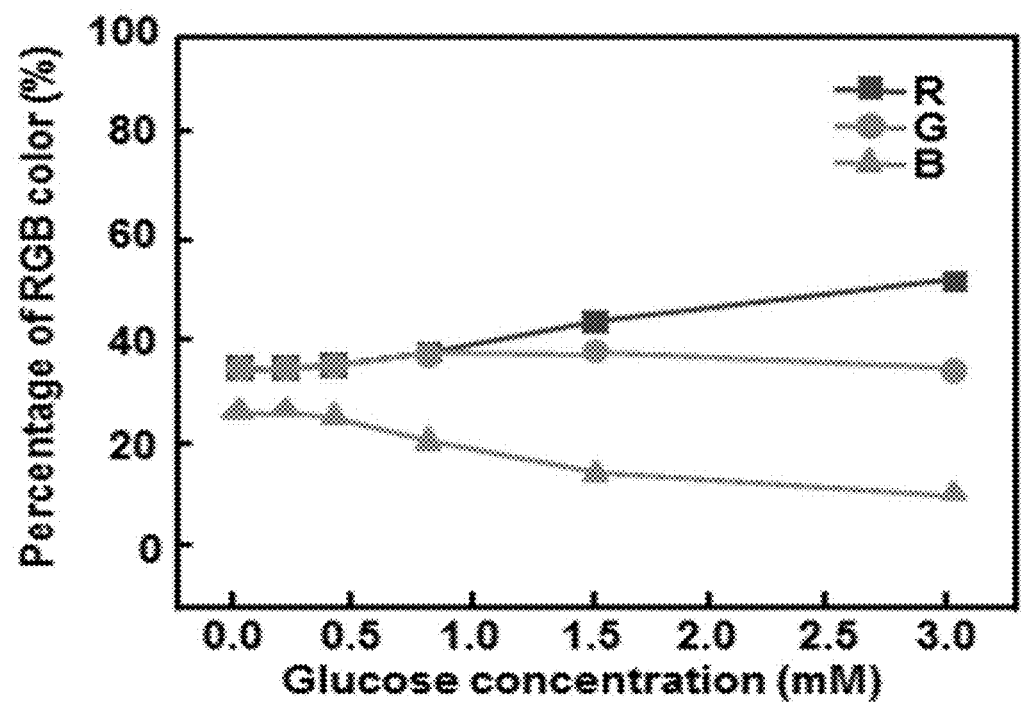
FIG. 19. Quantitative colorimetric analysis of glucose detection at low concentrations. (A) Standard calibration curve of normalized % RGB as a function of glucose concentration and (B) corresponding optical images of color in the detection reservoir.
Figure 19:
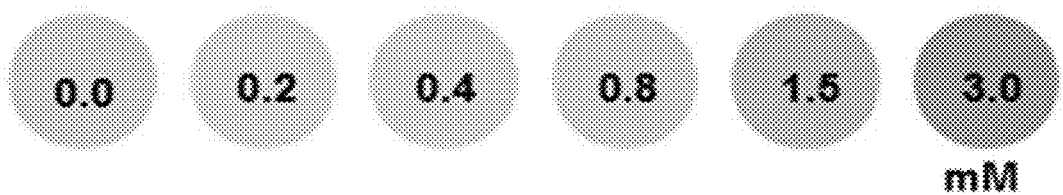

Glucose concentration could also be analyzed by an enzymatic reaction (FIG. 3d). Glucose oxidase physically immobilized in a cellulose matrix produces hydrogen peroxide associated with oxidation of glucose and reduction of oxygen. Following this reaction, iodide oxidizes to iodine by peroxidase, to yield a change in color from yellow (iodide) to brown (iodine), to an extent defined by the concentration of glucose (48, 49). We note that glucose concentration in sweat is typically one order of magnitude lower than in plasma; the range of sensitivity in the reported devices could diagnose hyperglycemia, for example [limit of detection (LOD)=~200 μM] (FIG. 19) (50). Further development of colorimetric chemistries based on enzymatic reactions and/or enzyme-mimetic nanomaterials could improve the limits of detection (52, 53). Similarly, creatinine, a vital marker of hydration status and renal function, was detected in sweat using a mixture of enzymes (creatininase, creatinase, and peroxidase) and a corresponding responsive dye (4-amino phenazone) (FIG. 3e) (51).

Figure 20:
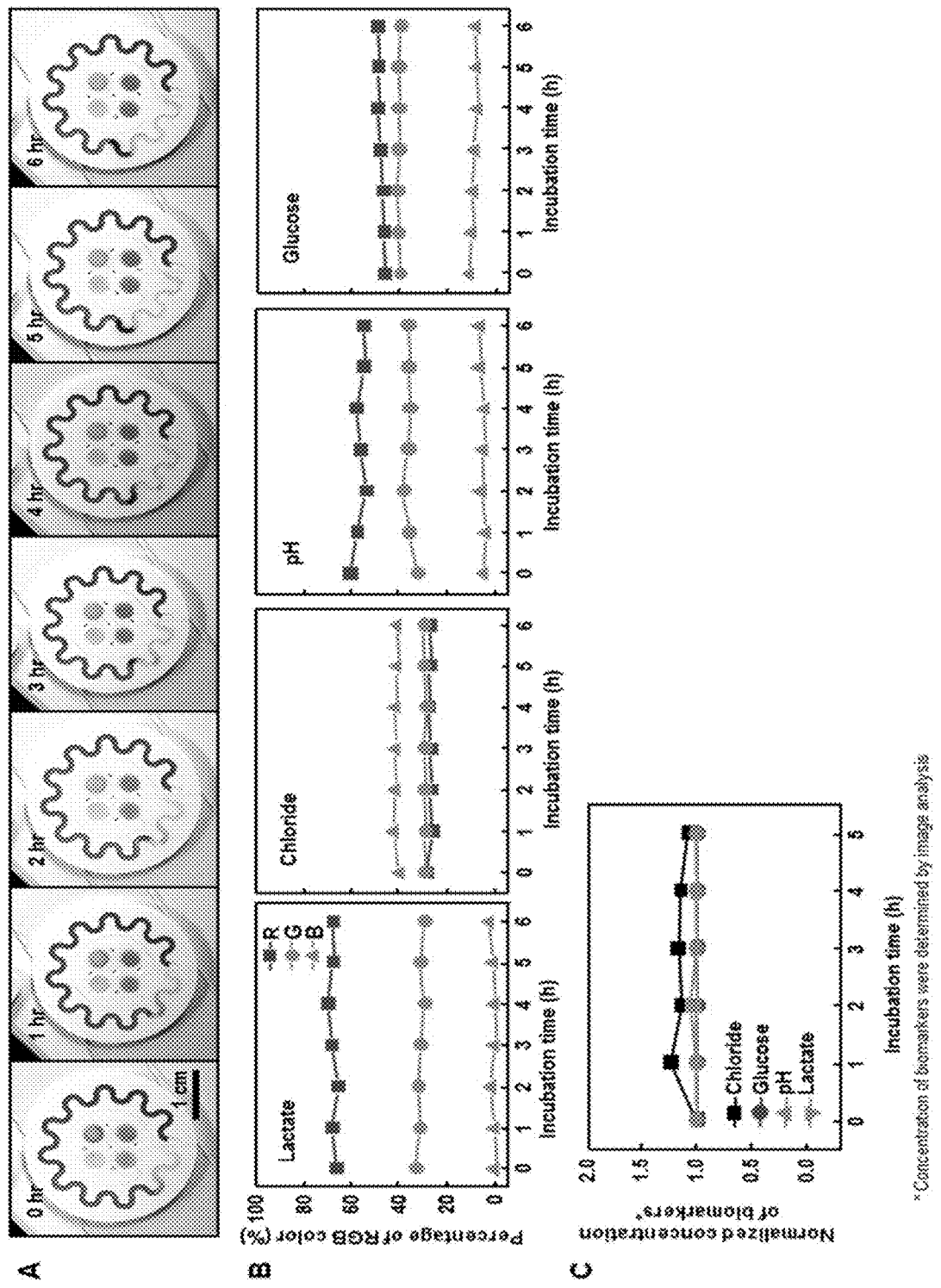
FIG. 20. Colorimetric analysis of device response as a function of time after introduction of artificial sweat. (A) Optical images of a device mounted on a glass slide on a white background collected hourly during a 6 hour period. (B) Corresponding % RGB information collected from the four biomarker detection reservoirs. (C) Relative changes of concentration normalized by the initial values via image analysis.

In sweat, pH is often considered an index of hydration state; the concentration of chloride ions serves as a marker of cystic fibrosis; and altered electrolyte levels correspond to a sodium ion imbalance (17). A universal pH indicator that includes dyes such as bromothymol blue, methyl red, and phenolphthalein yielded colorimetric responses over a medically relevant range (pH 5.0-7.0) (FIG. 3f). Colorimetric detection of chloride involved competitive binding between Hg$^{2+}$ and Fe$^{2+}$ with 2,4,6-Tris(2-pyridiyl)-s-triazine (TPTZ). In the presence of chloride ions, iron ions (Fe$^{2+}$) bind with TPTZ while Hg2+ participates as HgCl$_2$, thereby inducing a change in color from transparent to blue as shown in FIG. 3g. Although PDMS is known to have some permeability to water and certain small molecules, the colorimetric responses in these devices are not influenced for most practical applications due to the relevant operational timescale and the analyte chemistries used (FIG. 20).

Figure 4:
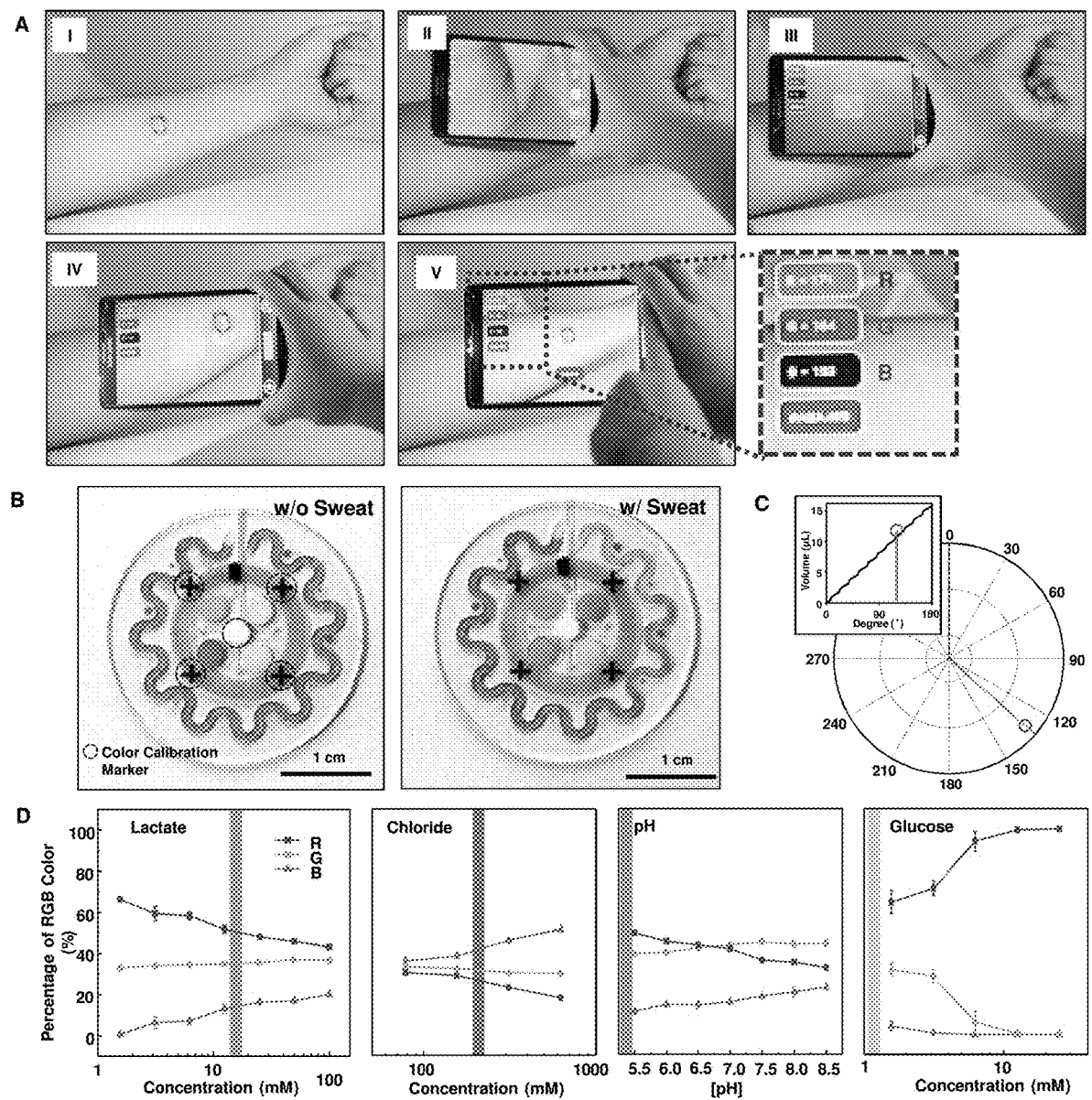
FIG. 4. Near field communication interface to a smartphone and image processing. (A) Pictures demonstrating near field communication between sweat monitoring device and a smart phone to launch software for image capture and analysis. (B) Images of the epidermal microfluidic biosensor (left) before and (right) after injecting artificial sweat. (C) Location tracking of sweat accumulation with polar coordinates and their relationship to total captured volume of sweat (inset). (D) Standard calibration curves between normalized % RGB value and concentration of markers for quantitative analysis (n=3, error bars represent the standard deviation). Each vertical colored bar represents the marker concentration determined from the corresponding reservoirs in the right image of (B) as an example.

Near field communication interface to a smartphone and image processing: Recording color changes and converting them into quantitative information was accomplished by digital image capture and analysis. FIG. 4a shows frames from a video clip in which the proximity of a smartphone to the device initiated image capture and analysis software automatically using NFC. The user then adjusted the viewing position to the targeted spot to determine exact RGB color in situ. The application digitized RGB color information on the screen, enabling the user to read the concentration of the marker. The previously reported ultrathin NFC electronics (39) integrated on the top of the microfluidic device enabled wireless communication to external devices, with stable operation and a soft, biocompatible set of mechanical properties, even under a 30% strain condition (39). The NFC electronics facilitated image capture, and built-in temperature sensors on the NFC chips provided wireless, digital data on skin temperature.

After wirelessly collecting images, image processing for assessment of color changes was achieved as shown in FIGS. 4b-d. Reference color markers (true white and black) allowed white balancing to eliminate the dependence of the analysis on lighting conditions of practical relevance (daylight, shadow, and various light sources) (FIG. 12). In particular, a white dot in the middle of the device and four black crosses distributed near the center established values for 100% and 0% in % RGB coordinates, respectively (FIG. 4b). The crosses further allowed rotations/translations of the images to facilitate accurate analysis of sweat rate and volume on the serpentine channel (FIG. 13). After image correction, the digital color data (in % RGB format) were converted into analyte concentrations using calibration curves (FIG. 4d). We could reliably measure changes of 0.5 pH units and 0.2, 0.3, and 0.1 mM of chloride, lactate, and glucose concentrations, respectively, corresponding to a 1% change in the R channel of the RGB images. Although the calibration curve in FIG. 4c captures the non-linearities associated with the serpentine shape of the channel, the angle of the filling front (the leading edge of the color change) in the serpentine channel defined the volume of sweat collected, thereby allowing calculation of total sweat loss and, with the time interval, total sweat rate.

Human testing of the skin-mounted sweat sensor: The first demonstration of practical utility involved nine human subjects with the device mounted on two different body locations (lower back and volar forearm, FIG. 5b) and with two different harvesting areas (size of the opening in the adhesive shown in FIG. 5a) during intermediate-level activity on cycle ergometers under controlled 38° C. temperature and 50% relative humidity conditions. We compared the performance of the device in situ to conventional procedures that use absorbing pads applied onto the skin with subsequent weighing and lab-based analyses, such as spectrophotometry.

Figure 5:
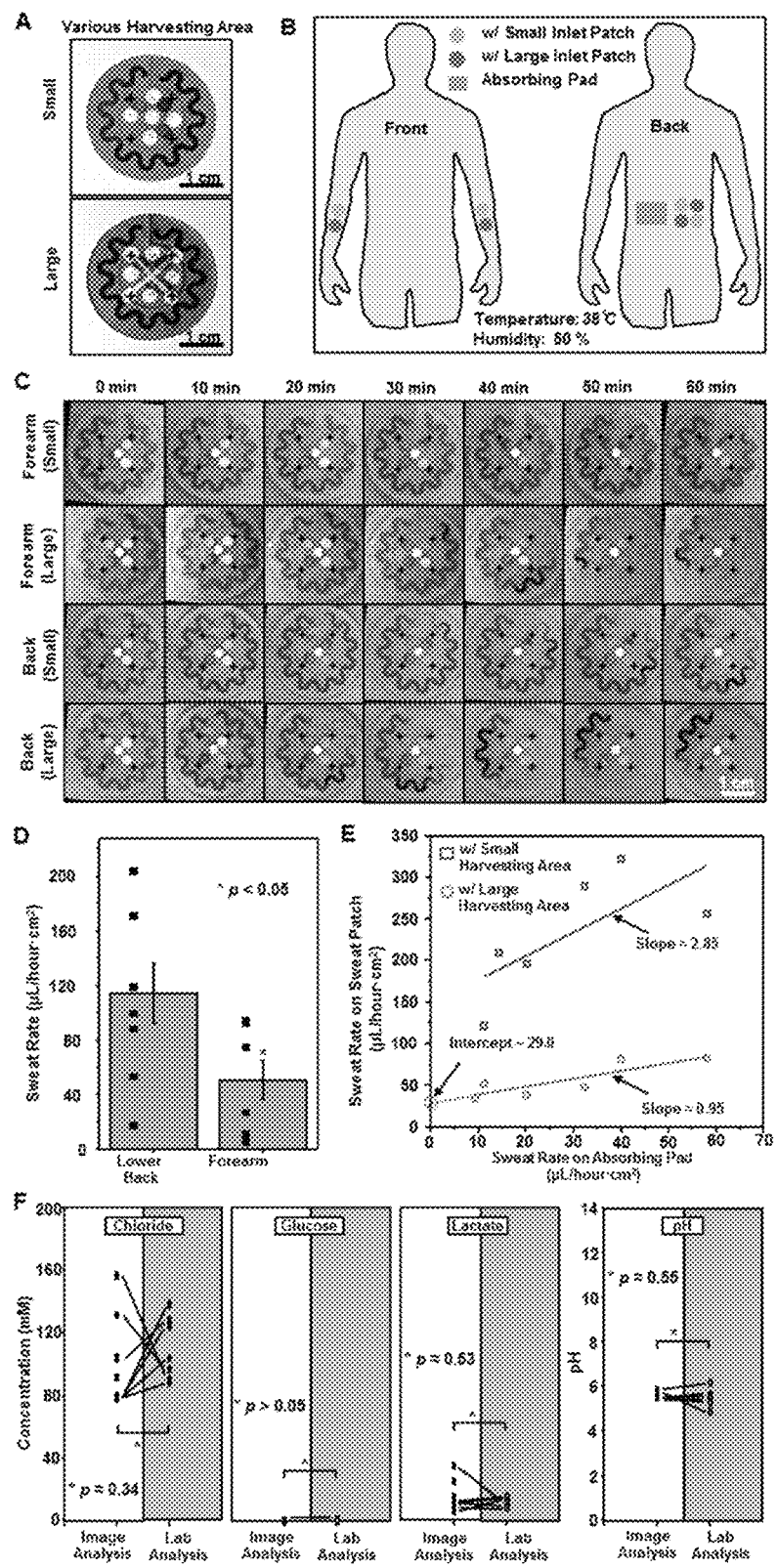
FIG. 5. Human trials of sweat monitoring devices in a temperature and humidity controlled room (35° C. at 50% relative humidity). (A) Adhesive layers utilized for human studies in a controlled setting. Brown color corresponds to the adhesive layer on the backside of the device with small and large harvesting areas (inlets). Absorbing pads served as a reference control. (B) An illustration indicating locations of sweat patches on the subjects (volar forearm and lower back). (C) Images of two different types of sweat patches (small and large harvesting areas) applied to the lower back and volar forearm according to study periods. (D) Difference of sweat rate according to body areas (lower back and volar forearm). Bars represent mean of n=8, error bars SD. *p<0.05, two-tailed t-test. (E) Correlation of sweat rate between the sweat patches and the reference-absorbing pads (n=7). (F) Marker concentrations in sweat obtained by image processing of data from the device (un-shaded) versus lab-based analysis of sweat collected from absorbing pads (shaded) (n=7). *p<0.05, two-tailed t-test.

We quantified regional sweat rate normalized to unit area over the course of 1 hour (FIG. 5 c and d). Although the rates exhibited great variation among individual subjects, sweat rates measured on the lower back were typically ~2.3-fold greater than on the volar forearm, consistent with expectations from studies using conventional techniques (54). Rates determined using the devices with large harvesting areas showed agreement with those obtained using absorbing pads (FIG. 5e). Furthermore, the devices accurately captured the volume and rate information continuously, without the need for removal. Notably, the y-intercept in FIG. 5e corresponds to the limit of sweat measurement with the absorbing pad due to water evaporation (0.349 g/cm$^2$s of water evaporation at 38° C., 50% relative humidity) during sample collection, highlighting one of its limitations. Devices with small harvesting areas yielded somewhat higher inferred rates than those with larger harvesting areas, perhaps due to alternations in perspiration behavior caused by the physical presence of the device (FIG. 5e) (55).

Concentrations of the markers chloride, glucose, lactate, and pH obtained by the colorimetric readouts demonstrated excellent agreement with conventional laboratory analysis of sweat collected from absorbing pads as shown in FIG. 5f. The glucose concentration in sweat from healthy subjects fell below the limit of detection for both image and lab analysis ($p<0.05$ refers to differences in background noise only). Bivariate and multivariate statistical analyses, together with Pearson correlation heat maps and Spearman rank-order statistics, quantified the correlations for all markers tested (FIG. 23).

Figure 6:
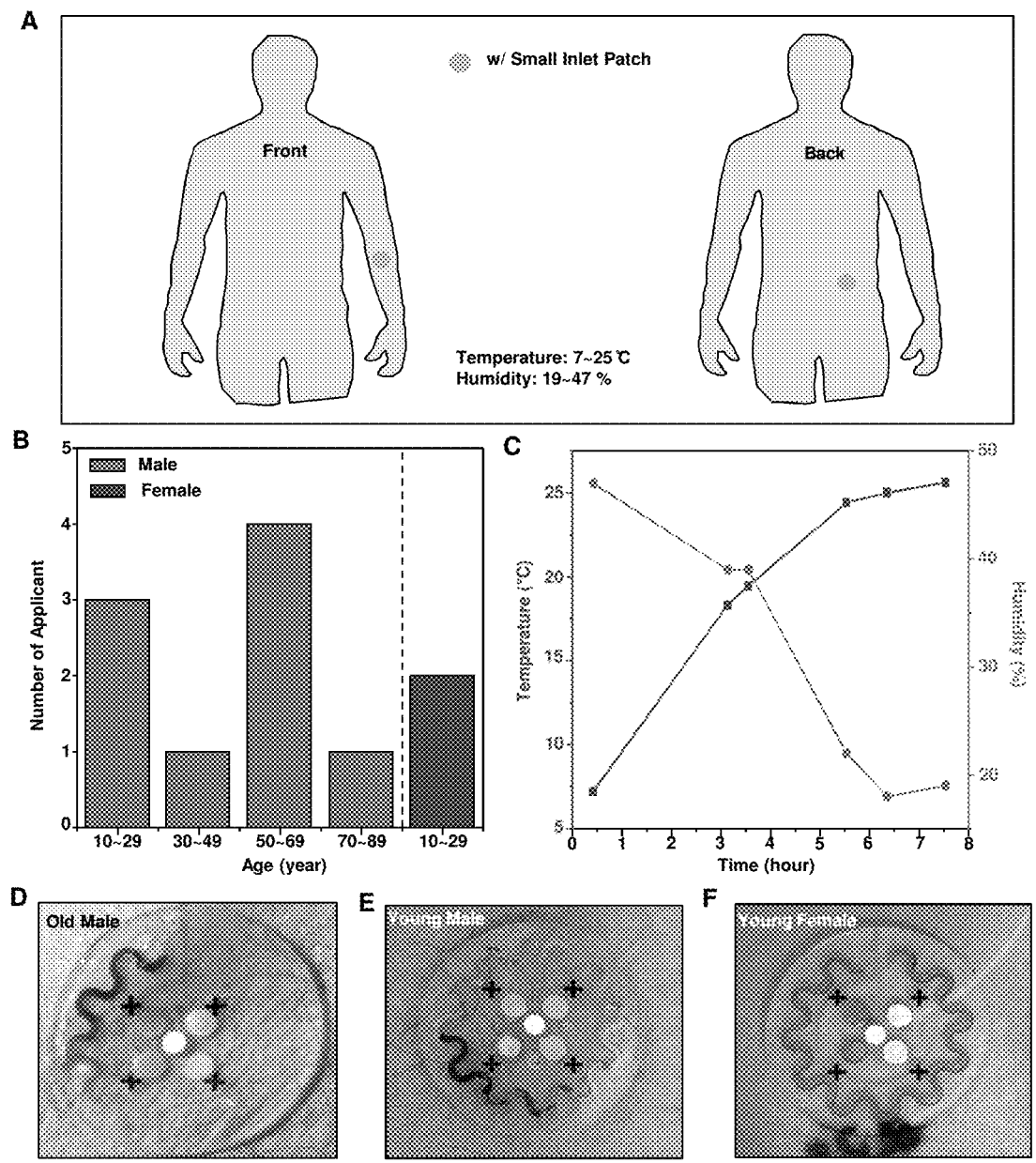
FIG. 6. Analysis of sweat monitoring devices on bikers in an uncontrolled environment. (A) An illustration indicating locations of sweat patches on the cycling subjects (volar forearm and lower back). (B) Histogram showing age distribution of cycling subjects. (C) Trends of temperature and humidity change during the race. (D) Elevation profile of the course. (E) Sweat patches on the volar forearms of study subjects, imaged after ~84 km of cycling (i.e., middle point of total race). (The purple ink in the lower part of the image on the right is from a marking formed on the skin using a pen, prior to application of the device.) (F) Sweat patches on the volar forearms of young female subject FIG. 7. Fabrication procedures of the epidermal microfluidic device using soft lithography.

To examine the mechanical and fluidic integrity of the devices in a demanding exercise scenario, we assessed robustness in adhesion and fluidic collection and capture using devices on volunteers in a competitive long distance outdoor bicycling race—El Tour de Tucson. Testing involved patch placement on the lower back and the volar surface of the forearm of 12 volunteer riders (FIG. 6b). In all cases, the devices performed as anticipated, successfully collecting sweat with regional colorimetric change without patch detachment, even with substantial changes in temperature and humidity. Participants reported no sense of discomfort or limitation in body or arm movement during the cycling. Older subjects (ages 50-69) had greater rates of sweating in comparison to that of younger subjects (ages 10-29), and male subjects exhibited greater rates of sweating than females (FIG. 6e).

The epidermal microfluidic devices introduced herein represent versatile platforms for evaluating athletic performance and monitoring health and disease status. The devices may detect sweat volume and rate, as well as several key markers including glucose, creatinine, lactate, chloride, and pH. Compared to previously described technologies for sweat analysis consisting of porous materials and fabrics or hydrogels as fluidic interfaces, our systems are unique in their use of fully integrated, soft microfluidics consisting of a network of functionalized channels and reservoirs for sweat capture, routing, and storage with spatially separated regions for analysis. The devices herein may provide further quantitative modes of use for additional applications. In addition to systematic investigations of the key engineering aspects and design parameters, initial studies demonstrated practical utility through tests on nine volunteers during moderate intensity exercise in controlled conditions, with correlation of measured results to standard methods based on absorbent pads and laboratory chemical analyses. Evaluations on twelve cyclists during high intensity physical exertion revealed real-word performance without loss of adhesion, leakage of fluids or other modes of failure, and without discomfort or irritation at the device/skin interface.

The soft mechanical properties, biocompatible constituent materials, digitally analyzable colorimetric responses, and overall careful optimization of structural, evaporative and fluidic properties are integral to the effectiveness of these devices and differentiate them from other sweat analysis devices. The applications include use of these devices for real-time, in situ sweat analysis and as storage vehicles for ex situ laboratory evaluation. In this latter context, it is important to note that we observed that the microfluidics structures described here can hold captured sweat for ~125 hours upon removal from the skin and sealing of the open channels (~75 hours without sealing) with negligible deterioration of colorimetric analysis.

These colorimetric schemes may be extended to include enzymatic reactions or chromogens aimed at a broad range of possible applications for specific clinical diagnosis or for illicit drug use detection. Advanced electronic or non-electronic strategies for temporal tracking of sweat chemistry are of interest. An alternative approach is in microfluidic designs that enable time-dependent sampling of sweat into spatially distinct reservoirs for separate analysis. In all cases, digital image capture analysis represents a simple, 'wireless' means of quantitation. Direct electronic readout represents an additional possibility, where epidermal power supplies or wireless power transfer schemes could be useful.

In addition to their use in sweat monitoring, similar systems are usable as direct capture and storage vehicles for subsequent colorimetric or conventional lab-based analysis for various accumulated biofluids such as tears, saliva, or discharges from wounds, especially for small sample volume collection (<~50 μL). The same platforms are combinable with electronic or pharmacological means to actively initiate the release of sweat or extraction of other biofluids (e.g., interstitial fluids). In both such active and passive collection modes, the devices are usable in athletic and military training to gain insight into critical electrolyte loss, thereby guiding earlier supplementation before symptomatic cramping and 'hitting the wall' points in time at which appropriate preventative treatment is no longer effective. In this scenario, and in others of interest, data accumulated over time from individual users is usable as the basis for the development of analytic approaches for interpreting trends in marker concentrations, with the potential to provide warning signs associated with physical activities that lead to abnormal responses. The intrinsically simple, low-cost nature of the devices facilitates rapid, broad distribution for use in these contexts.

Fabrication of epidermal microfluidic devices with integrated electronics: Photolithography using a negative photoresist SPR 220 4.5 (MicroChem) and deep reactive-ion etching (STS Pegasus ICP-DRIE, SPTS Technologies Ltd) generated topographically defined channels (300 μm in depth) on a silicon wafer, as a master. A thin, spin-cast layer of polymethyl methacrylate (PMMA; 3000 rpm for 30 s following with curing at 180° C. for 5 min) prevented adhesion of a layer of polydimethylsiloxane (PDMS; Sylgard 184, Dow Corning; mixed at a 30:1 ratio of base to curing agent by weight) cast at 200 rpm for 30 s and cured at 70° C. for 4 h. This process yielded an inverse replica of the relief on the silicon in a slab of PDMS (~700 μm total thickness). The colorimetric dyes were then loaded by fill-and-dry and drop-casting method in the channels and reservoirs, respectively. Details of preparation of detection cocktails are listed below.

The electronic part of the system consisted of a thin device with open, deformable architecture and near field communication (NFC) capabilities, constructed according to procedures described elsewhere (39). Electrodeposition of the backside of this system with $SiO_2$ allowed covalent bonding to a film of PDMS (~200 μm thickness) through chemical interactions where —OH groups formed by exposure to oxygen plasma. A similar bonding strategy joined this sub-system to the molded PDMS, to yield a network of closed microfluidic channels. A final bonding step integrating a layer of skin adhesive (PC2723U, ScapaHealthcare) also used a same condition. All plasma bonding steps used an oxygen plasma equipment (Harrick Plasma Cleaner, Harrick Plasma) under pressure of 500 mTorr with 'high' power for 1 min. A custom temporary tattoo laminated on the top of device provided alignment marks and color calibration features for image processing. The devices were stored at 4° C. in a refrigerator with food-saver sealing to preserve the enzymes and NAD+.

Preparation for quantitative colorimetric analysis of biomarkers: The serpentine microfluidic channels were coated with a solution of 100 mg/mL cobalt (II) chloride dissolved in a 2 wt % polyhydroxyethylmethacrylate (pHEMA) hydrogel. The resulting blue material formed thin layers on the internal walls of the channels after drying at ambient conditions for 30 min. Colorimetric analysis reagents were spotted on filter paper (i.e., 4 mm dia.) in their respective test zones. A 2 μL volume of a universal pH indicator solution (Ricca Chemical Company) served as a chromogen for pH detection. Preparation of the glucose detection cocktail involved dissolving 1.2 mg of glucose oxidase, 0.12 mg of horseradish peroxidase, 102 mg of trehalose, and 99.6 mg of potassium iodide into 1 mL of sodium citrate buffer solution (pH 6.0) (48, 49). A small volume (i.e., 5 μL) of this cocktail was introduced into the glucose detection reservoir. The lactate assay reservoir was prepared by adding a 3 μL mixture of lactate enzyme, substrate solution, and assay buffer (D-Lactase Assay Kit; Sigma-Aldrich) in a ratio of 3:2:5, respectively. A chloride detection reagent (3 μL; Chloride Assay Kit, Sigma-Aldrich) titrated with 0.1 wt % HgSCN until a clear appearance provided the functional component of the chloride assay reservoir. All of these paper-based assays were allowed to dry before physically inserted into the four circular reservoirs regions.

Optical absorption spectra in the UV-Vis range (i.e., 400-700 nm) collected using a double-beam Cary 5G spectrophotometer (Varian) with disk-shaped specimen holders (2 mm dia.) provided data to calibrate the various colorimetric responses. Test samples consisted of 5 μL of standard solutions with various concentrations placed on the paper-based assay substrates. Bare filter paper served as a reference material. These experimental samples were also used for constructing calibration curves of image processing.

Assessment of an epidermal microfluidic device: Scanning electron microscope (SEM; HITACHI S-4700, Hitachi) images were collected at an accelerating voltage of 5 kV after sputter-coating a thin layer of gold (20 nm). Mechanical properties were assessed with a DMA 800 (TA instruments) using a single cantilever for the rectangular shape block prepared by cutting the device. An artificial sweat simulator enabled in vitro evaluation of the device performance by mimicking the human perspiration system. The simulator consisted of a membrane with an array of pores prepared by laser drilling through a polyimide membrane (pores with 60 μm diameters at a density of 100 pores/$cm^2$ on membranes with 50 μm thickness). The pore-containing membrane was mounted onto a fluid chamber connected to a syringe pump while feeding water containing blue food dye with 5.5 μL/hour input rate for 6 hours (42).

Finite element analysis (FEA) and mechanics model of the microfluidic structures: ABAQUS commercial software (Dassault Systems) was used for FEA of the device under different external loads (stretching, bending and twisting). The focuses are to ensure that (1) the interfacial normal and shear stresses below the low somatosensory perception of the device on the human skin; and (2) the strain in the copper layer of the NFC electronics below the elastic limit such that no plastic yielding occurs. The classic theory for plates was used to calculate the deflection of the cover layer and volume change of the microfluidic channel under uniform in-plane pressure. An analytic model was established to quantitatively estimate the backpressure induced by inlet sweat flow for different outlet width. Simulation details and material properties (e.g., Young's modulus) are described below.

Full 3D FEA was used to study the mechanical performance of the devices, which were mounted on skin (100× 50×2 $mm^3$) subjected to stretching, bending and twisting. For stretching, displacements corresponding to 30% stretching were applied to two ends of the skin, which resulted ~16.8% average tensile strain on the bottom surface of the device along the stretching direction. For twisting, each end of the skin was subjected to 90-degree rotation such that the two ends of the skin had a 180-degree rotation. For bending, the displacement field applied to the bottom surface of the skin corresponded to 2 cm bending radius of curvature. Eight-node 3D solid elements were used for skin and PDMS microfluidic system, while four-node shell elements were used for the NFC electronics.

The elastic modulus and Poisson's ratio used in the simulations are 0.06 MPa and 0.49 for the skin (37); 0.145 MPa and 0.49 for the PDMS of the microfluidic system; 0.017 MP and 0.49 for the skin adhesive; 119 GPa and 0.34 for copper in the NFC coil; and 2.5 GPa and 0.34 for the PI of the NFC coil encapsulation.

Figure 21:
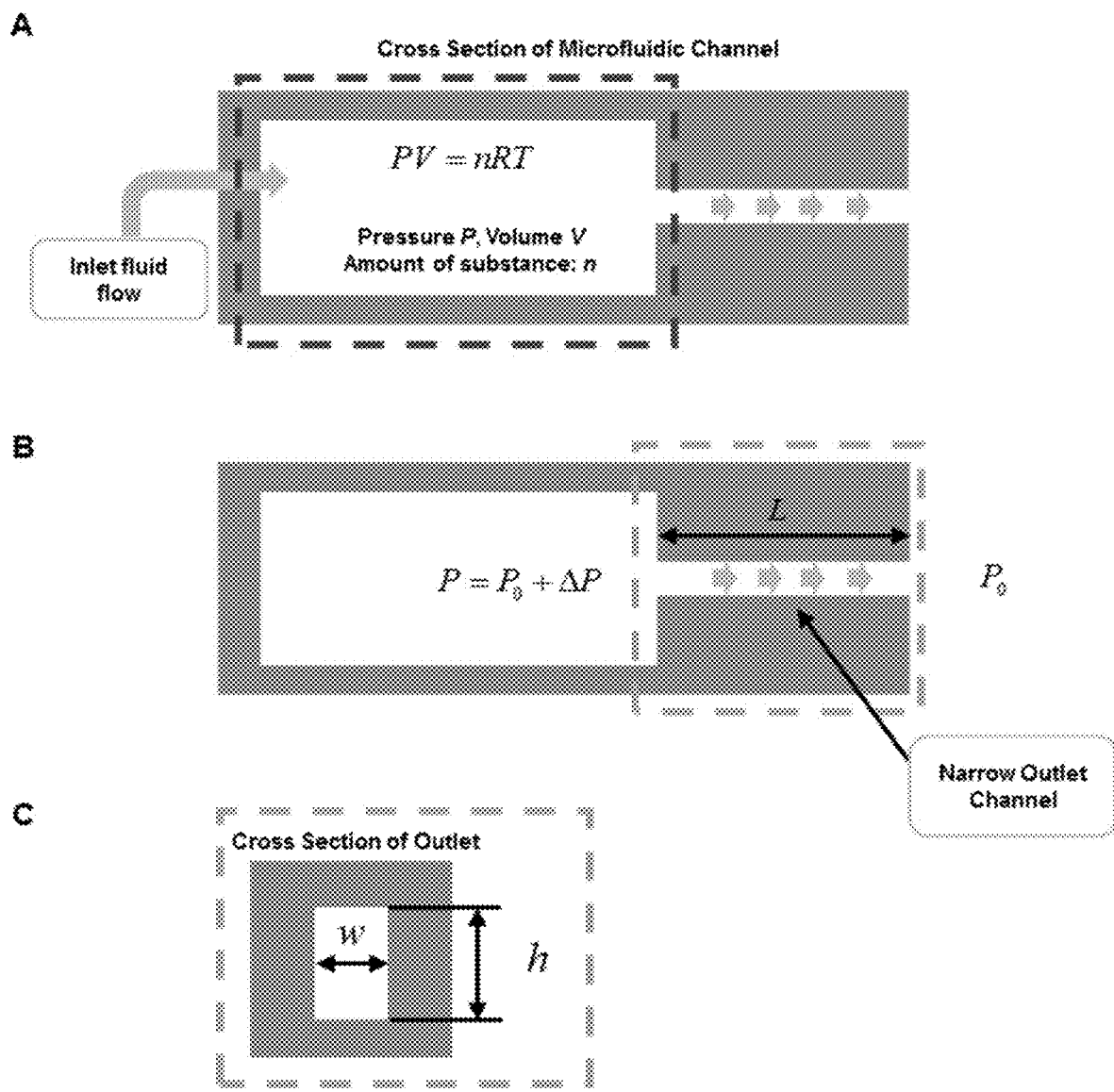
FIG. 21. Cross sectional sketch of the microfluidic channel and outlet channel geometry used for analytical analysis of backpressure. (A) The air inside the microfluidic channel obeys the ideal gas law, and (B) the relation between pressure drop ΔP and air escape rate is determined from fluid dynamics analysis of the outlet channel. (C) Cross sections view of the outlet channel.
Figure 22:
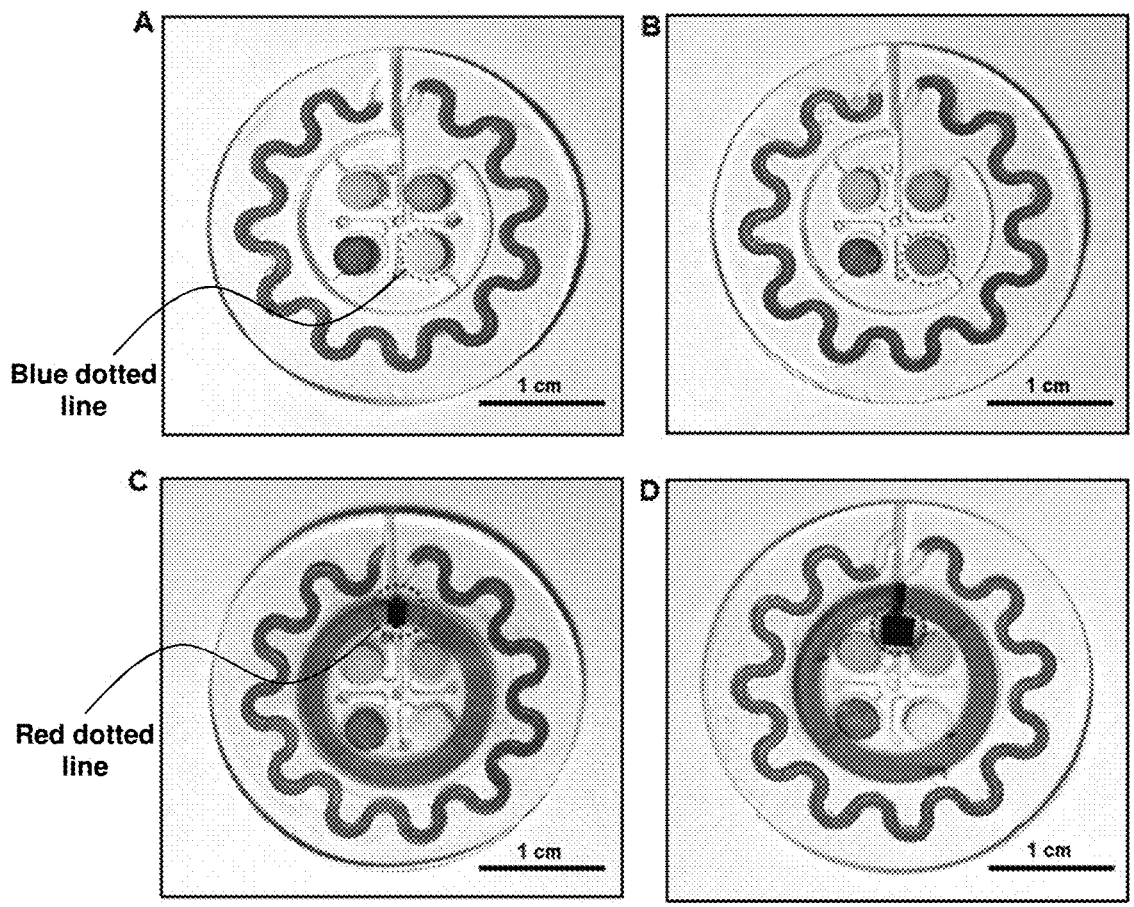
FIG. 22. Various device configurations. The sweat patch supports capabilities in detecting four difference biomarkers, including chloride, pH, lactate, and (A) glucose or (B) creatinine, where the latter two regions occur in the bottom right corners of the devices (indicated with blue dotted line). The near-field communication electronics can facilitate (C) image capture and (D) temperature sensing by use of M24LR04E (ST Microelectronics) and SL13A (AMS AG) chips, respectively (indicated with red dotted line).

Deformation under Uniform Pressure: The cross-section of the serpentine channel is shown in FIG. 2a and FIG. 21. The cover layer of the channel is modelled as a shell under cylindrical bending with clamped boundary conditions. For a channel of width under uniform pressure, the maximum deflection of the cover layer is (57)

$$w_{max} = \frac{pa^4}{384 \overline{EI}} \quad \text{(II)}$$

Here $$\overline{EI} = \frac{E}{1-v^2} \frac{t^3}{12}$$

is the bending stiffness, where E, v are Young's modulus and Poisson's ratio of the elastomer, respectively, and r is the thickness of the cover layer. The percentage change of volume can be calculated by integrating the deflection along the cover layer as $$\frac{\Delta V}{V_0} = \frac{pa^4}{720 \overline{EI} h} = \frac{ph^3}{720 \overline{EI}} \left(\frac{a}{h}\right)^4 \quad \text{(III)}$$

It scales with the fourth power of the channel width a, and therefore can be drastically decreased as a decreases (FIG. 2c).

Analysis of Backpressure: For the air inside the microfluidic channel (FIG. 21a), its volume V decreases as sweat flows into the channel, and satisfies the ideal gas law $$PV=nRT \quad \text{(IV)}$$

where P, T and n are the pressure, temperature and amount of substance (number of moles), respectively, and R is the ideal gas constant. It is important for the microfluidic channel to have an outlet, without which the pressure P would continue to increase as V decreases, and would impede the fluid flow. For a constant temperature, the rate form of Eq. V gives $$\dot{P}V+P\dot{V}=\dot{n}RT \quad \text{(V)}$$

Here $\dot{V}=-\dot{V}_{inlet}$ for an incompressible fluid, where $\dot{V}_{inlet}$ is the inlet sweat flow rate. For a constant $\dot{V}_{inlet}$ and sufficiently long time such that P reaches a steady-state value (and $\dot{P}$ approaches zero), the air escape rate $\dot{n}$ is given by $$\dot{n} = -\frac{P\dot{V}_{inlet}}{RT} \quad \text{(VI)}$$

Another relation between $\dot{n}$ and pressure P can be obtained from the air flow through outlet channel, which is modelled as a rectangular tube of length L, height h and width w (FIG. 21 b and c). The mean velocity $\bar{u}$ of air through the outlet is linearly proportional to the pressure difference on both sides of the outlet channel $\Delta P=P-P_0$ ($P_0$ is the atmosphere pressure) (58)

$$\bar{u} = \frac{\left(\frac{2wh}{w+h}\right)^2 \Delta P}{32 \mu L} \quad \text{(VII)}$$

where μ is the viscosity of the air. The air escape rate $\dot{n}$ is related to $\bar{u}$ by $$\dot{n} = -\frac{\bar{u}wh\rho}{M_{air}},$$

where ρ and $M_{air}$ are the density and molar mass of the air, respectively. The relation between $\dot{n}$ and ΔP is then given as $$\dot{n} = -\frac{\left(\frac{2wh}{w+h}\right)^2 hw\rho}{32 \mu L M_{air}} \Delta P \quad \text{(VIII)}$$

Elimination of from Eq. VI and Eq. VII gives backpressure ΔP $$\Delta P = \frac{P_0}{\frac{w^3 h^3}{8L(w+h)^2} \frac{\rho}{\mu M_{air}} \frac{RT}{\dot{V}_{inlet}} - 1} \approx \frac{8L(w+h)^2}{w^3 h^3} \frac{\mu M_{air}}{\rho} \frac{\dot{V}_{inlet} P_0}{RT} \quad \text{(IX)}$$

The constants used in all calculations include the atmosphere pressure $P_0=10^5$ Pa; temperature T=300K; molar mass $M_{air}$=29.0 kg/mol, viscosity μ=1.8×10$^{-5}$ Pa·s, and density ρ=1.2 kg/m$^3$ of air; idea gas constant R=8.31 J·mol$^{-1}$·K$^{-1}$; and the sweat flow rate $\dot{V}_{inlet}$=15 μL/hour, which corresponds to the maximum sweat rate 150 μL/(hour·cm$^2$) (32) multiplied by the device inlet area (0.125 m$^2$).

Near-field communication and image processing for quantitative analysis: The NFC electronics allowed communication with NFC enabled smartphones. This wireless interface automatically launched open color analysis application software to yield RGB values that can be connected to the concentrations of the selected biomarkers. Image-processing algorithms allowed quantitative analysis. Black crosses at the four corners and a white circle in the center yielded reference colors for white balancing, by defining 1 and 0 for all RGB values, respectively. Image analysis performed in this manner enabled extraction of accurate RGB color components, independent of lighting conditions. Known concentrations of biomarkers resulted in color changes to establish standard calibration curves. The black crosses facilitated image positioning, for reliable detection of the angular position of the leading edge of color change in the serpentine channel.

Human studies: In the controlled indoor study, volunteers consisted of healthy individuals (n=9, males and females, ages 18-40) with healthy intact skin in the investigational areas; systolic blood pressure 90-130 mmHg; diastolic blood pressure 50-90 mmHg; and a Body Mass Index (BMI) between 20-30. Clinical Research Laboratories, Inc. (NJ, USA) recruited volunteers and the Allendale Institutional Review Board approved the protocol (No. ACR/SWET/15-0121). Subjects provided written informed consent. The four investigational areas included the right and left volar forearm and the right and left lower back. The investigational areas were gently cleaned with soap and water, and dried before application of the devices. Two sets of microfluidic patches (a set of sweat patches includes small and large inlet sweat devices (n=2)) were applied on the right lower back while one set of microfluidic patches were applied to the right and left for each volar forearm. A total of eight sweat patches were thus laminated on each subject. One Webril®

Handi-Pad applied to the left lower back as a reference absorbing pad. Evaluation consisted of 60 minutes of cycling, sitting, and image capture intervals. Subjects sat for 5 minutes first and then peddled on a bicycle ergometer for 5 minutes (22.5±1.6 km/h). After the cycling was completed, one image of each investigational area (lower back, right and left forearm) was captured with an iPhone camera, an Android camera, and a Cannon camera, in standard lighting conditions. This procedure continued for 60 minutes in a conditioned room at 38±2° C. and 50±5% humidity. The subjects were provided water during the intervals as needed. After the tests, the microfluidic patches and the Webril® Handi-Pad were removed and the pad were stored in a freezer (−80° C.) until time of analysis For the outdoor real life demonstration, twelve volunteers, providing informed consent, participating in the El Tour de Tucson (Tucson, Ariz.) perimeter bike race were enlisted. The volunteers consisted of healthy individuals (10 Males and 2 females; ages ranging from 23-70 years; with BMI 20-33; and a body surface area (BSA) between 1.6-2.3 $m^2$). Temperature during the El Tour inclined from 7 at the start of the race to 25.6° C., while humidity dropped from 47 to 19% during the race. Nine, two, and one volunteers completed 167, 88, and 64 km of racing, respectively, with a collective average speed of 26.9 km/h. All volunteers wore the sweat monitoring patches on their lower back and volar forearms. Before, during and after the race, sweat patch images were collected via a digital camera and additional sweat patches were applied at the mid-point of race (i.e., ~84 km) in selected individuals. Images were obtained immediately after the race to avoid any artifacts due to reabsorption of sweat.

Lab-based Sweat Analysis: Sweat obtained from subjects during the indoor human study was collected as infranatant (i.e., lower liquid portion) by centrifuging at 2,500×g for 2 min using a tube divided with 3D printed porous barrier layer. Absorbance microplate reader examined chemical compositions (i.e., glucose, chloride, and lactate) of the collected sweat (50 μL for each well) in the lab using a standard colorimetric analysis kit (Sigma-Aldrich). The pH value was determined using a micro pH meter (Hanna Instruments).

Statistical Analysis: Obtained data is presented with average value and standard deviation (SD). Pearson and Spearman correlation analyses were conducted on the patch and laboratory results (FIG. 23). The matrix of bivariate correlations in biomarker concentrations between patch and lab analysis has been displayed using a heat map representation. Blue denotes negative correlation and red positive correlation. Bivariate correlations have also been described using Spearman rank-order statistics. Analyses have been performed using SAS and JMP statistical software.

Example 2: Thin, Soft, Skin-Mounted Microfluidic Networks with Capillary Bursting Valves for Chrono-Sampling of Sweat Systems for time sequential capture of microliter volumes of sweat released from targeted regions of the skin offer the potential to enable analysis of temporal variations in electrolyte balance and biomarker concentration throughout a period of interest. Conventional methods that rely on absorbent pads taped to the skin do not offer the ease of use or the fidelity in sweat capture needed for quantitative tracking in realistic settings; emerging classes of electronic wearable sweat analysis systems do not directly manage or exploit sweat-induced fluid flows for sample isolation. Here, we introduce a thin, soft, 'skin-like' microfluidic platform that bonds to the skin to allow for collection and storage of sweat in a set of microreservoirs. Filling occurs pressure induced by the glands themselves to drive flow through a network of microchannels that incorporate capillary bursting valves designed to burst at different pressures, for the purpose of passively guiding sweat through the system in a well-defined, time-ordered fashion. The operation is robust to mechanical stresses encountered during application, operation and removal from the skin, with negligible chemical contamination or unwanted fluid mixing. After use, a set of collection chambers located in a radial array at the periphery of the device can be filled by centrifugal force, with capability for long or short term sample storage prior to ex situ chemical analysis. The materials and fabrication schemes support a broad range of choices in layouts, sizes and numbers of microchannels and microreservoirs, for different use scenarios and mounting locations. Human studies demonstrate applications in the accurate chemical analysis of lactate, sodium and potassium concentrations and their temporal variations.

Sweat, a biofluid excreted from eccrine glands in the epidermis, contains electrolytes (sodium, chloride) and lactate, urea and small concentrations of proteins, peptides and metal ions.[1] The concentrations of these and other biomarkers can provide important information on physiological state, such as dehydration[2], and on diseases such as cystic fibrosis[3] and childhood pancreatic disease.[4] Temporal changes and variations in the chemistry of sweat across body positions offer additional valuable insights into health status. [5-7] In this context, wearable devices capable of collecting and storing sweat into discrete chambers have potential value. Established technologies rely on absorbent patches (PharmChee® [8]) or coiled tubes (Macroduct® [9]), and serve only as passive vehicles for sweat collection over a certain period of time. Capturing samples at different times requires repeated application and removal of such devices [5-7]. Emerging forms of wearable, electronic sweat analysis systems [12-19] exploit electrochemical approaches for monitoring biomarker concentrations, but they also do not allow for collection, capture or subsequent analysis of discrete samples of sweat captured at well-defined time points.

Recent work on thin, soft, skin-mounted microfluidic systems establishes routes for exploiting sophisticated concepts in lab-on-a-chip technologies for sweat collection and analysis [10-17]. Here, sweat glands, which create pressure due to natural differences of osmolality between plasma and sweat [18], actively drive flow into a network of microchannels and microreservoirs. The maximum pressures generated in this manner are estimated to be ~70 kPa per gland, sufficient for this purpose[19]. Although previously reported systems do not incorporate any valves for controlling the direction of flow through the microfluidic network, piezoelectric[20], electrokinetics[21] and chemical [22] approaches are compatible with the basic platform, and can be considered for this purpose. Herein, we report an approach that guides flow in these type of skin-mounted microfluidic devices via a collection of carefully designed capillary bursting valves (CBVs) that direct the flow of sweat to fill a collection of microreservoirs in a time sequential manner, thereby providing a precise sampling capability. Past work on conventional lab-on-a-chip technologies demonstrates that CBVs are used for stop valves [23-26] and flow guides [27, 28], but not for the type of control achieved here. Systematic in vitro tests illustrate robust, stable function in various conformal, skin-compatible designs that additionally allow efficient means for storage and final extraction of discrete samples of sweat. Human field testing validates the utility of platforms configured for sequential sweat sampling followed by extraction and ex situ chemical analysis, with a focus on lactate, sodium and potassium. Results indicated differences between sweat generated by thermal exposures and by running exercises, as well as variations with position across the body.

Experimental Section: Materials and Methods:
Device Fabrication

Figure 29:
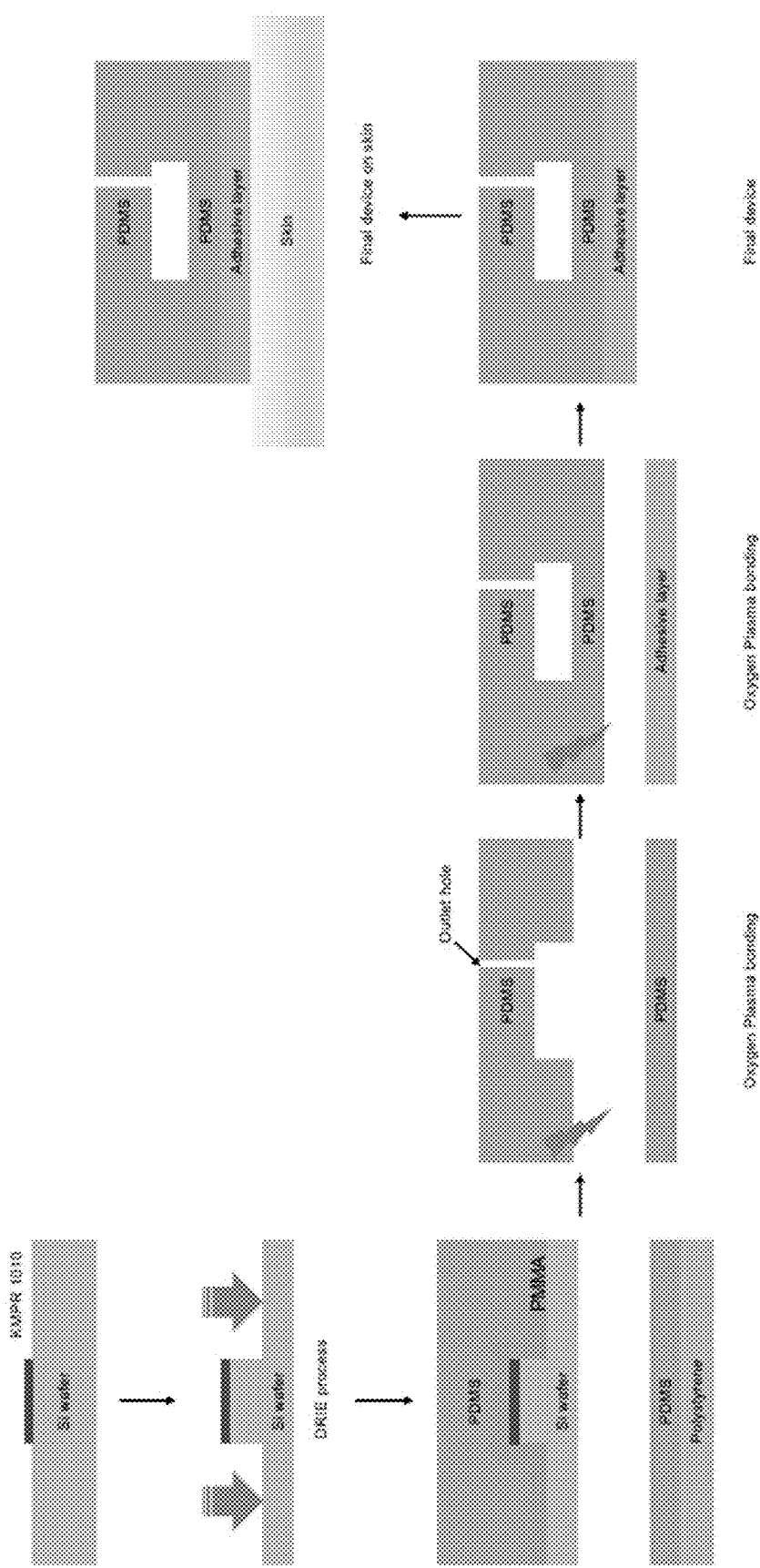
FIG. 29. Fabrication procedures of the epidermal microfluidic device.

Fabrication of molds began with spin coating of a 15 µm thick film of photoresist (KMPR 1010) on a silicon wafer (FIG. 29). After photolithography and developing, deep reactive ion etching (STS Pegasus ICP-DRIE, SPTS Technologies Ltd) created trenches in the silicon to a depth of 300 µm. Spin coating forms thin layer of poly(methylmethacrylate) (PMMA; Microchem, MA, United States) on the resulting mold. Pouring poly(dimethylsiloxane) (PDMS at a 30:1; Sylgard 184, Dow corning, MI, United States) onto the PMMA film and then spin coating at 200 RPM formed a thin (400 µm) layer. A mechanical punch tool defined holes with ~1 mm diameters at the outlet hole of each of the extraction chambers. For capping layer, pouring PDMS (30:1) onto polystyrene petri dish (VWR, IL, United States) and then spin coating at 400 RPM formed bare layer (200 µm). A mechanical punch tool defined hole with 1 mm diameter located at the center of the capping layer. Exposure to oxygen plasma generated at low (6.8 W) RF power at 500 mTorr (Plasma Cleaner PDC-32G, Harrick Plasma, NY, United States) for 10 sec, the channel part and capping layer are aligned for inlet and bonded. Aging the bonded structure for 24 hours allowed the PDMS surfaces to recover their hydrophobic properties. Bonding to a skin adhesive (PC2723U, ScapaHealthcare) with a 2 mm diameter hole aligned to the inlet completed the fabrication. Introduction of a solution of 100 mg/mL cobalt (II) chloride dissolved in a 2 wt % polyhydroxyethylmethacrylate (pHEMA) hydrogel (Sigma-Aldrich, MO, United States) into the channels facilitated visualization of the filling process.

In Vitro Chrono-Sampling Test and Measurement of Bursting Pressure:

A hydrostatic pressure generator served as the basis for a simple in vitro model of sweat generation, for the purpose of characterizing the CBVs (FIG. 30a). The height of the top of a water column at the bursting point provided an estimate of the BP. As calibration, the pressure created by the generator was compared to the value from a microfluidic pressure controller (Fluigent MFCS, Villejuif, France).

In Situ Chrono-Sampling Test:

Application of ethanol swabs cleaned the skin of volunteers involved in the studies, shortly before application of the devices. For the thermal exposure tests, the subjects remained in a dry sauna at 55° C. for 30~40 min.

For the running exercises, the subjects ran with a constant speed at ~10 km/h. After the tests, the devices were peeled from the skin and centrifuged at 5000 RPM to move sweat from the collection chambers into corresponding extraction chambers. For measuring sweat rate by conventional method, hydrophilic foam dressing (Covidien, MA, United states) in 2 cm×2 cm size was used.

Chemical Contamination Test:

Tests for chemical contamination of sweat by any of the materials used in the device construction materials used a PDMS channel 2 mm in width and 0.5 mm in depth with PDMS cover and adhesive which an overall construction identical to that of the actual devices (FIG. 30a). Artificial sweat consisted of an aqueous solution of 22 mM of urea, 2.2 mM of glucose, 3.8 mM of potassium, 31 mM of sodium, 58 mM of chloride and 5.2 mM of calcium (Sigma-Aldrich, MO, United States). This fluid filled the PDMS channel and remained there for 2 hours at room temperature prior to recovery for chemical analysis. A similar sample, without exposure to the test structure, served as a control.

Chemical Analysis:

Analysis of lactate involved 1 µl of sweat extracted from the device and subsequently diluted in 100 µl of water. This sample was introduced into liquid chromatography-mass spectrometry system (Waters Synapt G2-Si ESI, MA, United States) with an ACQUITY UPLC BEH C18 column (130 Å, 1.7 µm, 2.1 mm×50 mm) at a flow rate of 0.2 ml/min. Solvent A was 95% water, 5% acetonitrile and 0.1% formic acid; solvent B was 95% acetonitrile, 5% water and 0.1% formic acid. For sodium and potassium analysis, 0.5 µl of sweat were extracted from the device and subsequently diluted in 1 ml of water. The sample and three standard samples were diluted in 2 ml of 0.5% nitric acid as preparation for inductively coupled plasma mass spectrometry (ICP/MS; SCIEX ELAN DRCe, PerkinElmer, CT, United States). For chloride analysis, 1 ml of artificial sweat diluted in 25 mL of water and the 20 ml of solution was mixed with 0.4 mL of ionic strength adjuster. Ion selective electrode was used for measuring chloride concentration (Thermo Scientific, MA, United States).

Contact Angle Measurement:

Static contact angles were measured using 5 µl droplets of de-ionized water dispensed using an automated system and measured with a contact angle goniometer (KSV CAM200, Stockholm, Sweden). Contact angles were evaluated after 10 s of contact. The results establish the kinetics of recovery of hydrophobic properties of the PDMS surface.

Figure 24:
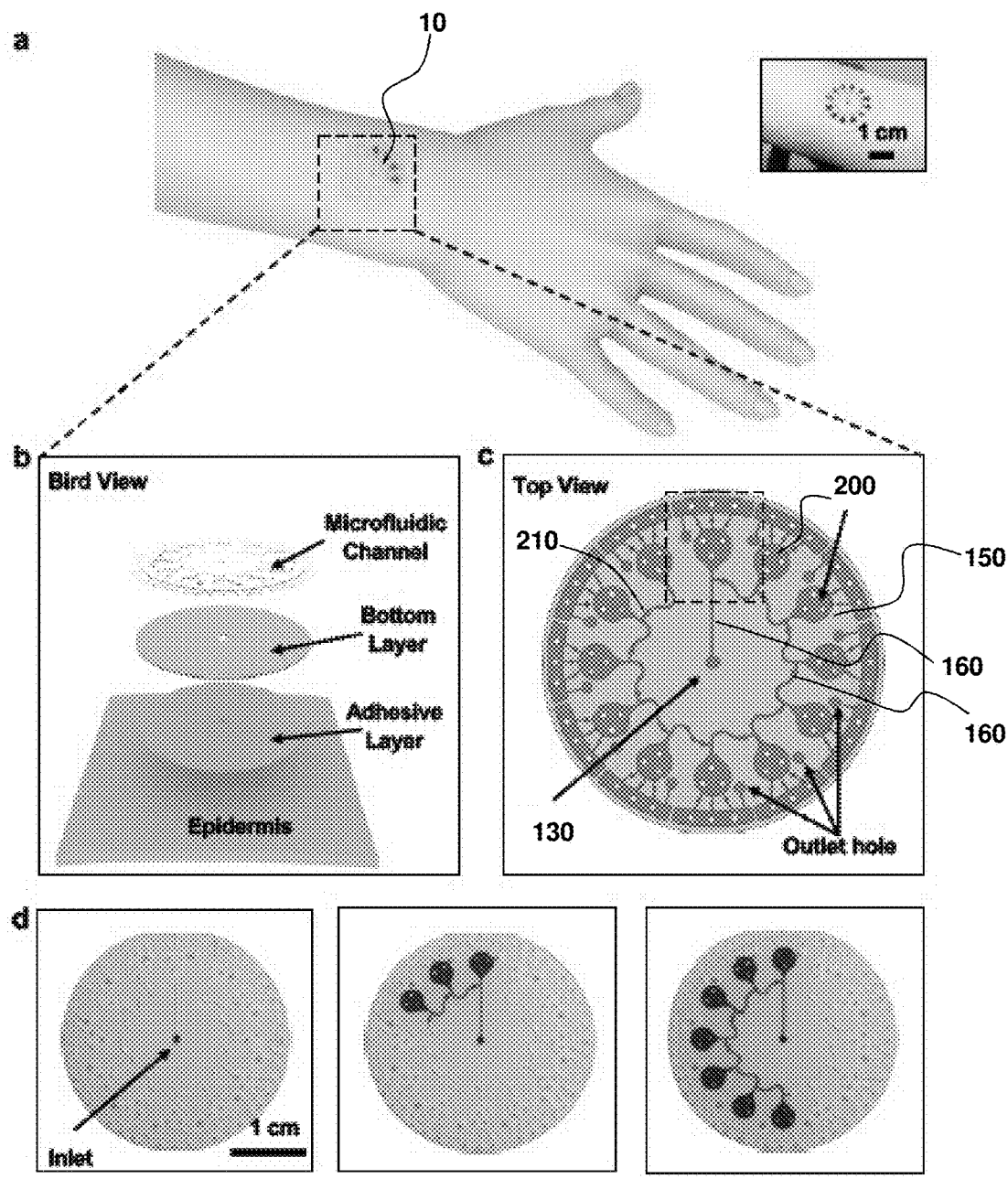
FIG. 24. (a) Schematic illustrations and optical images (inset) of thin, soft (i.e. epidermal) skin-mounted microfluidic systems for chrono-sampling of sweat. (b) Exploded schematic illustration of a device. (c) Top view illustration of microfluidic channels filled with dyed water. (d) Optical images of an in vitro test of sequential sampling of dyed water introduced into a device at constant pressure.

Thin, soft microfluidic devices for chrono-sampling of sweat: The thin, soft physical properties of these devices allows their intimate, comfortable bonding to the skin for the purpose of collecting, manipulating, analyzing and storing sweat, captured in a sequential manner. A representative device shown in FIG. 24a has a circular overall geometry with a diameter of 3 cm. The radial construction facilitates the use of centrifugation techniques for collection of sweat after removing the device from the skin, as described subsequently. The design involves two layers of poly(dimethylsiloxane) (PDMS) supported on a medical-grade acrylic adhesive film for bonding to the skin. The first layer defines a network of microfluidic channels (400 µm thickness; channel widths and heights are 200 µm and 300 µm, respectively) and the CBVs (designs described next), the second serves as a capping layer (200 µm thickness) and the third (50 µm thickness) establishes adhesion to the skin and defines openings (2 mm diameter) from which sweat enters the microfluidic system (1 mm diameter, inlet; FIGS. 24b and 29). The system in FIG. 24 consists of a network of microfluidic channels that connect to 12 separate chambers in parallel by bridging channels (FIG. 24c). Each chamber has an outlet opening (0.5 mm diameter) to release air pressure that would otherwise build during the filling process.

Figure 30:
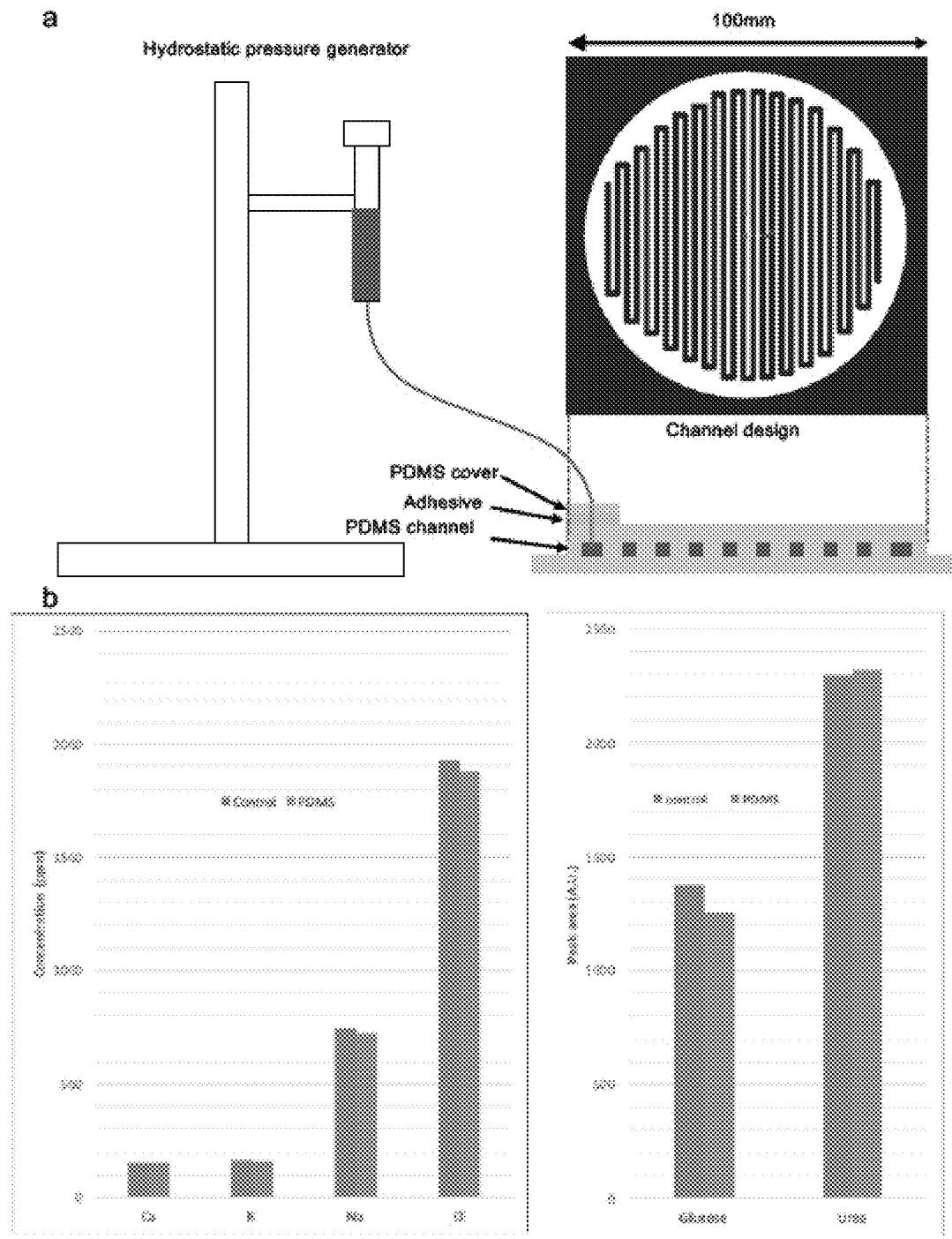
FIG. 30. Chemical contamination test in chrono-sampling device. (a) hydrostatic pressure generator fills the PDMS long channel. (b) quantitative chemical analysis of calcium, potassium, sodium and chloride in artificial sweat from PDMS device and control. (c) qualitative chemical analysis of glucose, urea in artificial sweat from PDMS device and control.

In vitro tests using dyed water illustrate the clockwise flow through this network (FIG. 24d). PDMS is a good choice due to its dimensional stability in water [29], materials biocompatibility[30], low modulus, elastic mechanical properties, and compatibility with simple molding and bonding processes for fabrication[31-33]. Careful testing indicates an absence of chemical contamination from the PDMS and the adhesive layer in analysis of biomarkers of interest in sweat (FIG. 30). These same results suggest a minor (~10%) decrease in glucose concentration, possibly due to slight absorption into the constituent materials of the device.

Figure 31:
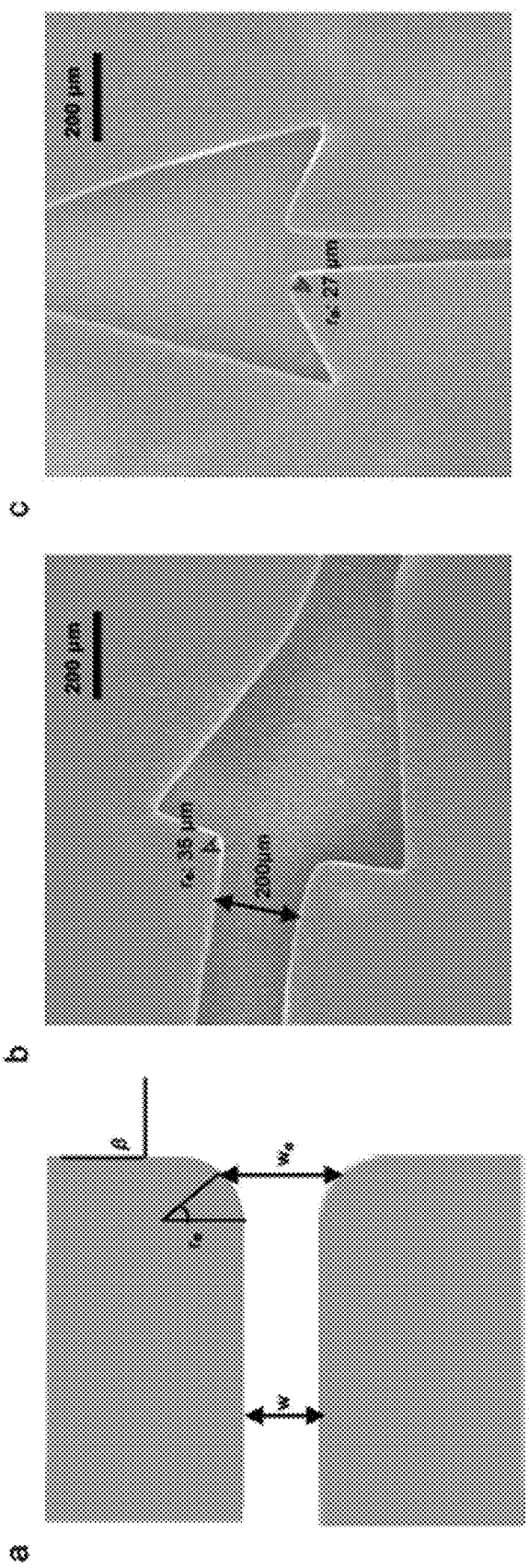
FIG. 31. Rounded edge of the capillary bursting valve (CBV). (a) actual description of the valve with round edges. The radius of the rounded edge of CBV #2 (b) and CBV #3 (c).

Principle and Design of the Capillary Bursting Valves for Time Sequential Sampling: The CBVs block flows at pressures lower than their characteristic bursting pressures (BPs) [34]. When liquid in a single connected channel encounters two separate CBVs with different BPs, at sufficient pressures, the flow will proceed first through the valve with lower BP. In this way, locating two CBVs with different BPs near the intersection between two channels allows control of the direction of flow. The Young-Laplace equation gives the BP in a rectangular channel as equation (Eq.) (X) [34, 35], $$BP = -2\sigma\left[\frac{\cos\theta_I^*}{b} + \frac{\cos\theta_A}{h}\right], \tag{X}$$

where $\sigma$ is the surface tension of liquid, $\theta_A$ is the contact angle of the channel, $\theta_I^*$ is the min[$\theta_A+\beta$, 180°], $\beta$ is diverging angle of the channel, b and h are width and height of the diverging section, respectively. For hydrophobic materials at high diverging angles, the BP increases with decreasing b and h. Each unit cell of the devices described here includes three CBVs, a collection chamber, an extraction chamber and a sampling outlet (FIG. 25a). In one embodiment, the first two CBVs, denoted #1 and #2, have diverging angles of 36° and 90°, respectively, and widths of 200 μm. The third CBV, i.e. #3, has a diverging angle of 120° and a width of 50 μm (FIG. 25b). The heights of the valves are 300 μm. According to Eq. (I), the contact angle of the channel surfaces affects the BP. PDMS, which is naturally hydrophobic, becomes hydrophilic after exposure to oxygen plasma for the purpose of activating the surfaces to enable bonding. The hydrophobicity recovers [36] after ~24 hours, to reach a constant, time-independent contact angle of 107°. Based on this value, the computed BPs for CBVs #1, #2 and #3 are 713.4 (BP #1), 881.7 (BP #2) and 3035.7 Pa (BP #3), respectively. Experimentally measured values are somewhat lower than these estimates, mainly due to imperfections in the fabrication and, in particular, diverging angles that are slightly smaller than the design values, as shown in the SEM images in FIG. 25a. For example, in CBV #2 and #3, the sharp edges where the straight channel and the diverging section intersect are rounded, with radii of curvature of approximately 35 μm and 27 μm, respectively (FIG. 31). Decreasing the channel opening angle tends to decrease the bursting pressure. Therefore, the bursting pressure of the valve with a round edge is lower than that with a sharp edge (FIG. 31.)

Liquid that initially arrives at CBVs #1 and #2 encounters them in their closed states (FIG. 25e(i)). Upon reaching or exceeding BP #1, CBV #1 opens to allow flow into the chamber (ii). After filling this chamber, the liquid flow bursts CBV #2 at sufficient pressure (BP of CBV #2 is lower than that of CBV #3) (iii). By this process, all 12 chambers fill in a sequential manner, for flows that involve pressures larger than BP#2. For constant flow rate, this effect translates to time-sequenced sampling, or chrono-sampling. After use, the device can be removed from the skin and then inserted into a centrifuge (5000 rpm) to open CBV #3, thereby for moving liquid from each of the storage chambers into corresponding extraction chambers to facilitate recovery for lab analysis (iv). The designs of the CBVs ensure that pressures generated by the sweat glands exceed BP #1 and BP #2, but not BP #3, and that centrifugal pressures exceed BP #3.

Figure 26:
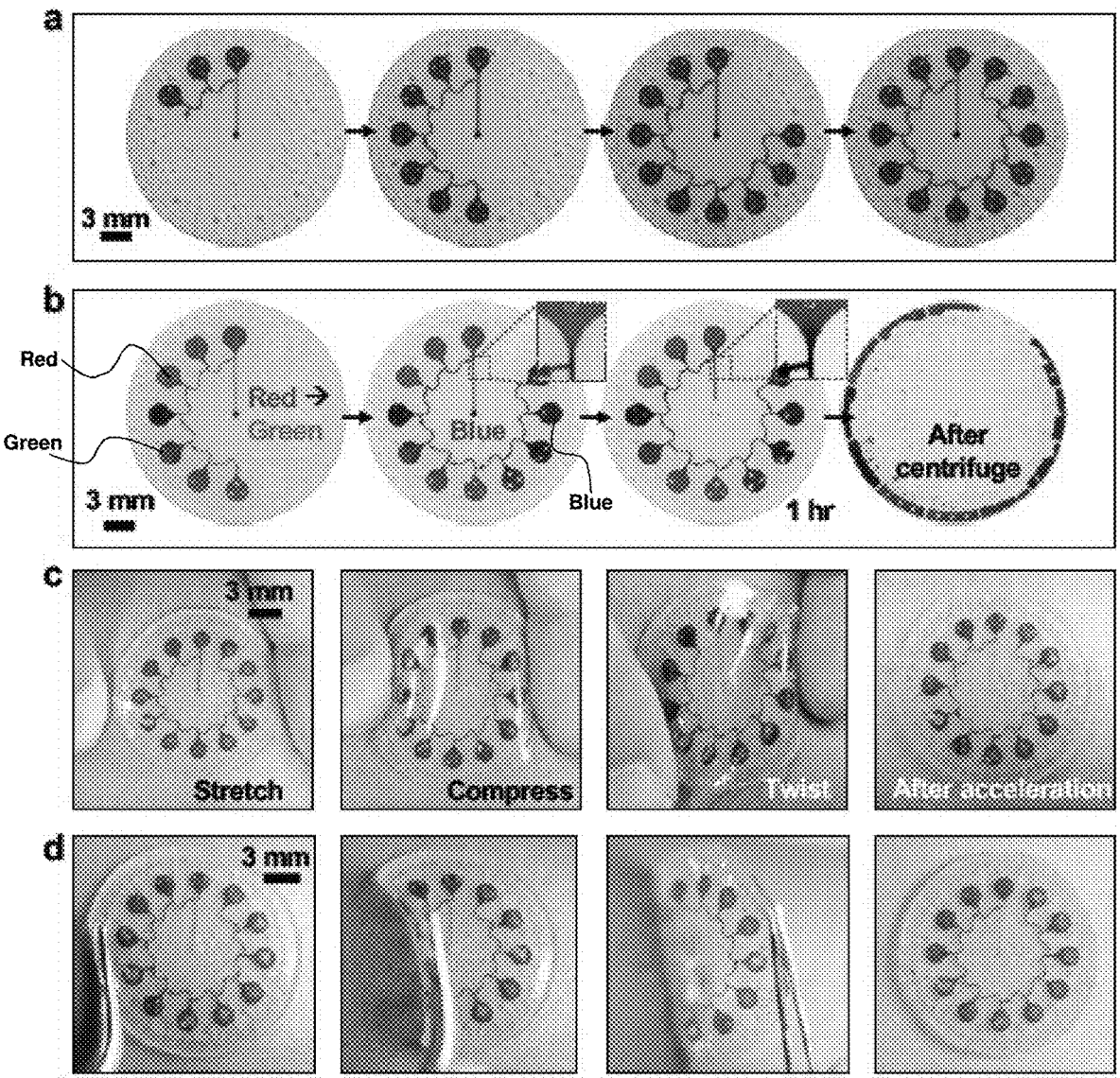
FIG. 26. Optical images of (a) in vitro test of chrono-sampling of dyed water introduced into 12 collection chambers, (b) in vitro test of chrono-sampling of different color dyes in water (red, green and blue) with enlarged image of the interface between adjacent colors and after separation by centrifugation, (c) chrono-sampling device filled with dyed water and attached to the skin under various mechanical distortions: stretching, compressing, twisting and undergoing rapid motion, (d) removing a device filled with dyed water and attached to the skin.

Fluidic operation and stability under mechanical perturbation: FIG. 26a shows that these epidermal microfluidic chrono-sampling devices can sequentially collect liquid without undesired bursting of CPVs. The flow properties of the microchannels ensure absence of unwanted mixing. Specifically, for channel dimensions of hundreds of micrometers and flow rates of 1-20 μl/min/glands, the flows are laminar, i.e. low Reynolds numbers (<1), and mixing occurs only by molecular diffusion [37, 38]. The example here illustrates operation with water dyed using different colors and introduced in a time sequenced manner. Over relevant time scales (~1 h) and temperatures (~22° C.), diffusion occurs only within ~1 mm of the interfaces between water with different colors, corresponding to less than 10% of the total volume of the collection chamber. The fourth chamber in this example is relatively dark due to mixing of the red dye in the bridge channel with green dye. Here, the red dye comes from the inlet and green dye follows the red, in sequence. After filling 11 chambers, removing the device and performing centrifugation, each separate sample of sweat moves into a corresponding extraction chamber. FIG. 26c highlights the soft nature of these devices and their ability to stretch, flex and twist without damage. The function of the microfluidic channels, CPVs and chambers is unaffected by these deformations or by shaking movements of the arm. Even the process of removing the device from the skin for chemical analysis, which includes significant mechanical stresses, does not affect the stability or fluidic containment (FIGS. 26c and 26d).

Figure 27:
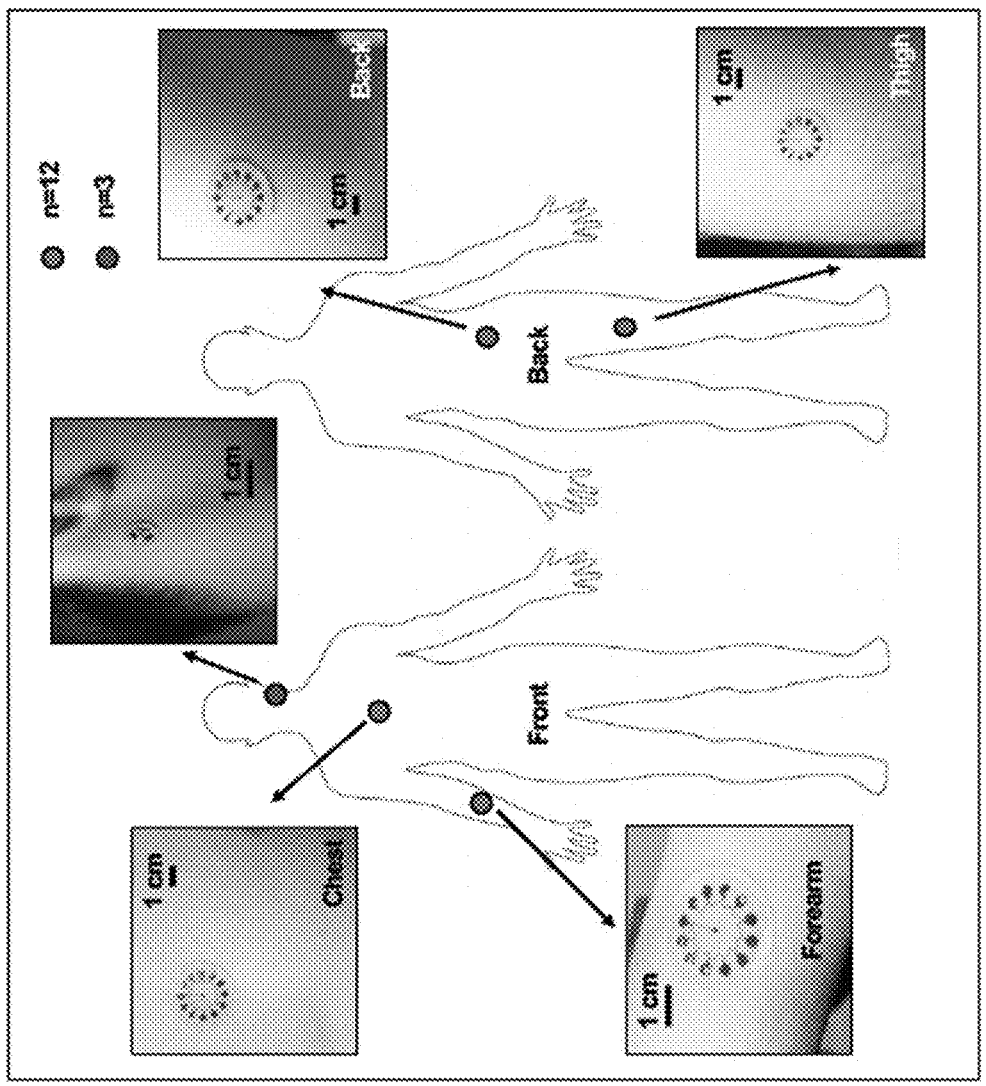
FIG. 27. Optical images of (a) devices with various sizes and configurations, each filled with dyed water. The sizes range from 1 cm to 4 cm in diameter, with numbers of chambers from 3 to 24, (b) devices at various mounting positions across the body; behind the ear, chest, back, forearm and thigh, (c) device with sweat guiding channels on its bottom side, as a mechanism for release of sweat from regions under the device but away from the inlet, (d) device with additional set of channels and chambers in the center, (e) device immediately after sampling of dyed water (0 h) and after 3 days of storage while held using a clamp designed to prevent evaporation through the outlet channels.
Figure 27:
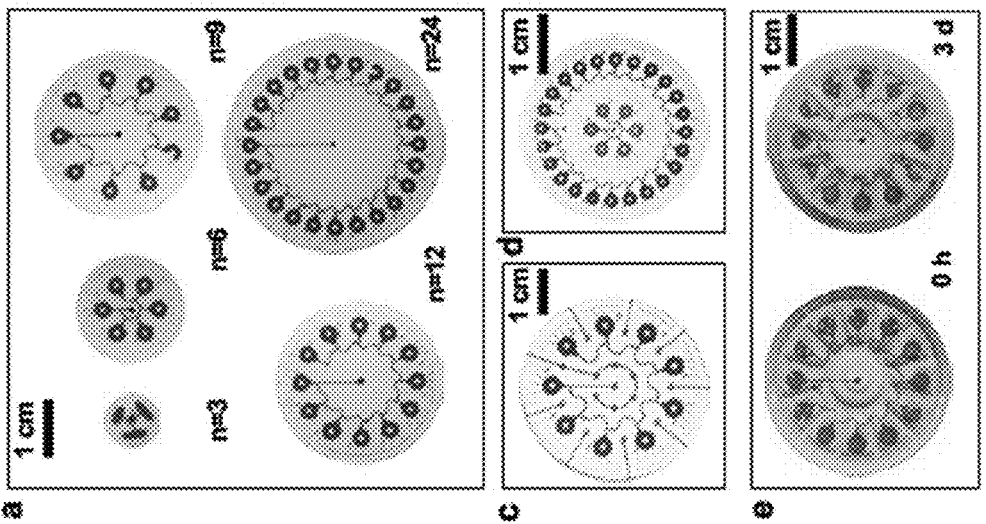
Figure 28:
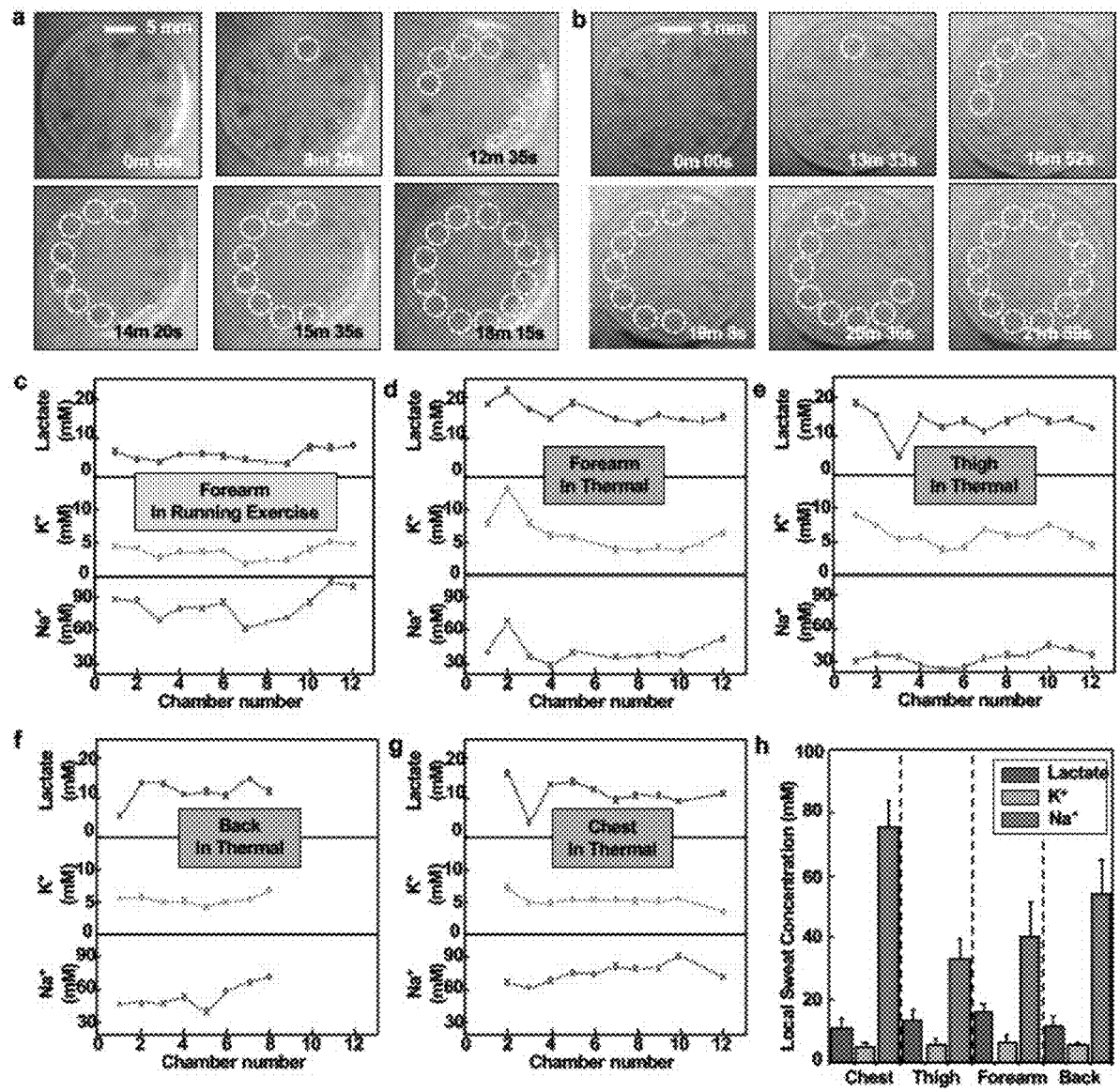
FIG. 28. In situ perspiration analysis from various body positions during running exercise and thermal exposure in a sauna. Chrono-sampling of sweat generated on the forearm during a running exercise under constant load (a) in thermal exposure at 56° C. (b). Cobalt (II) chloride dissolved in pHEMA and loaded into the devices aids in visualization of the filling process. Chemical analysis of lactate, sodium and potassium in the sweat extracted from a chrono-sampling device mounted on the forearm during a running exercise (c), from forearm (d), thigh (e), back (f) and chest (g) in thermal exposure. (h) Regional variations of biomarker concentrations in sweat (lactate, sodium and potassium) collected from different body positions; chest, thigh, forearm and back.
Figure 32:
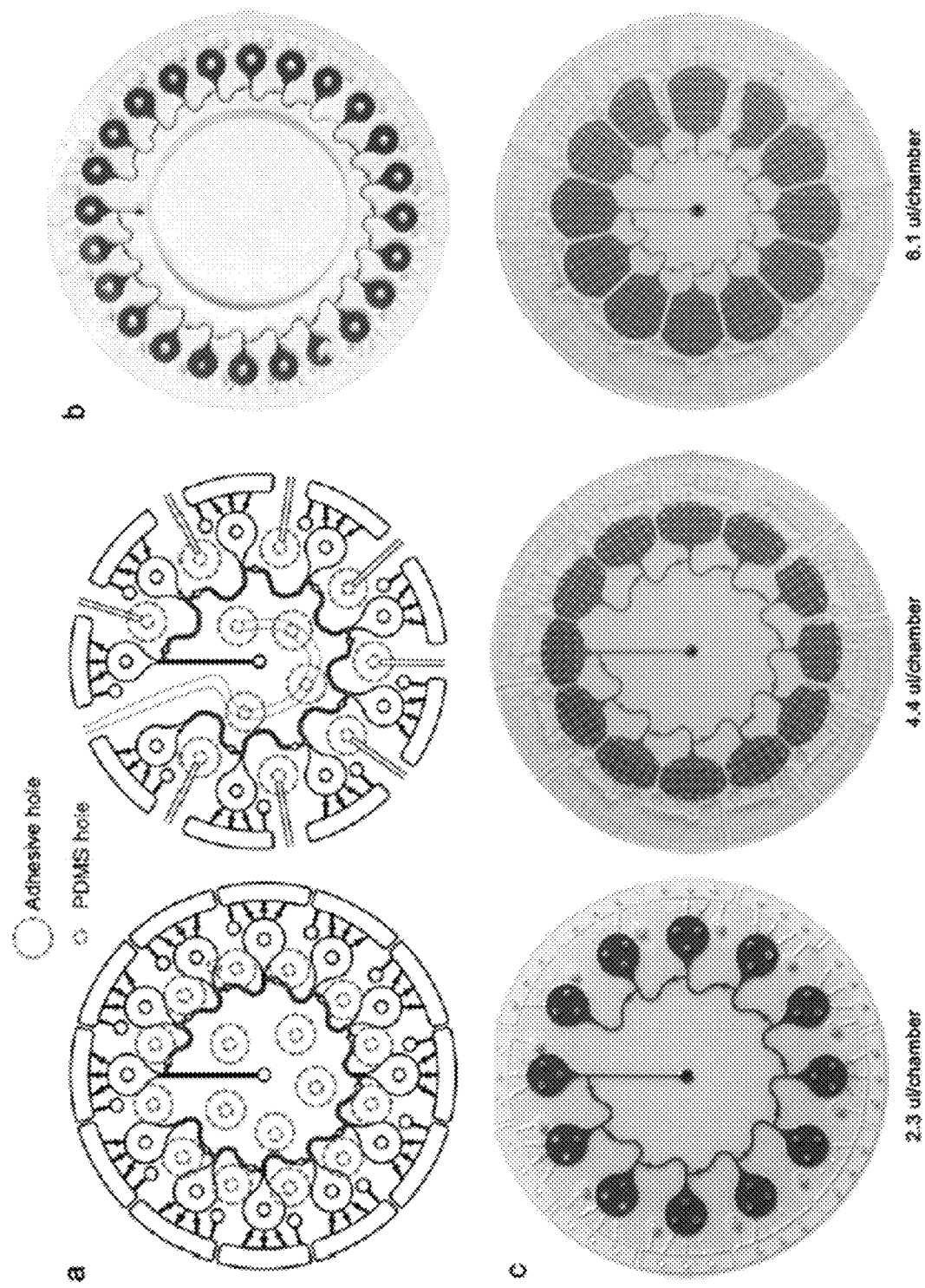
FIG. 32. a) chrono-sampling device with thorough hole in the device or leak out channel for guiding the sweat not for analysis b) chrono-sampling device with cutout in the middle. c) various device with different volume of chamber from 2.3 to 6.1

Various applications of epidermal microfluidic sweat chrono-sampling device: These device platforms offer significant design versatility in terms of overall dimensions, sizes of microfluidic channels and chambers, and numbers of chambers, as illustrated in FIG. 27a. The smallest device shown here has three chambers, and a circular layout with a diameter of 1 cm, for use in space constrained regions such as behind the ear. Due to the thin, soft mechanical construction, this device and others with different designs are mountable on various locations on the body with equal fidelity, including the chest, back, forearm and thigh (FIG. 27b). Additional features can be included. For example, in a standard layout, the adhesive covers the skin everywhere except for regions for collecting sweat. Possible effects related to blockage of sweat glands are reducible with the addition of channels of relief on the bottom surface of the device to define skin-interfaced microfluidic channels for transport of sweat to the outer perimeter (FIGS. 27c and 32a.) Another option involves the introduction of open architectures via removal of regions of the device where the skin adhesive interface is not necessary (FIG. 32b). Such layouts improve not only management of flows of sweat in these locations but they also increase the mechanical deformability. For a large device, it is possible to locate an additional set of sampling capabilities in the center region (FIG. 27d). The volume of the chamber can also be defined to meet requirements, with examples of 2.3 μl and 6.1 μl in FIG. 32c.

Figure 33:
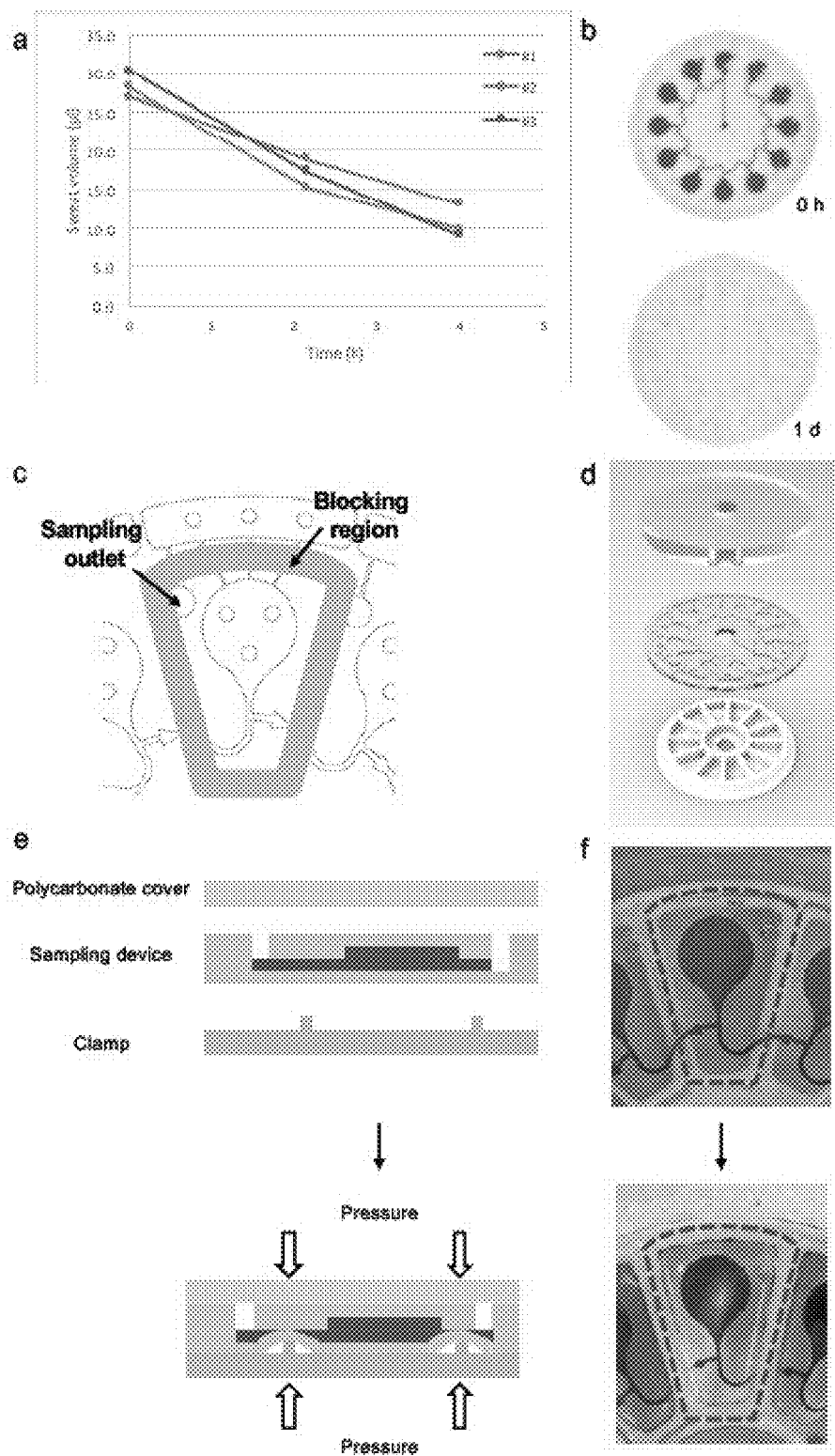
FIG. 33. Mechanical clamp for blocking evaporation (a) evaporation rate of chrono-sampling device filled with dye in water. (b) evaporation test of chrono-sampling device filled with dye in water. (c) blocking region in the device. (d) exploded schematic illustration of mechanical clamp and PDMS device. (e) cross-section illustration of working principle of clamp f) the device filled with due in water before and after clamping. The wall in the clamp block the channel in the device.

The microscale dimensions of the devices, the water permeability of PDMS and the presence of microchannels and chambers with open outlets collectively lead to non-negligible rates of evaporation of sweat during and after use. Experiments show that the evaporation rate from a typical device is ~3.5 μl/hr in a fully filled state, which corresponds to a per-chamber rate of ~0.25 μl/h at 35° C., 40% relative humidity (FIG. 33*a*). This rate corresponds to ~10% of the chamber volume per hour. Systematic studies show that most evaporation occurs through the sample outlets (FIG. 33*c*). For long-term storage, mechanical clamps designed to block these regions (FIGS. 31*c-e*) reduce the rate to 0.55 μl/hr at 25° C., 30% relative humidity such that more than 50% of the samples can be retained in the device for 1 day. Storage in high humidity conditions (99%) is possible for several days (FIG. 27*d*).

Figure 34:
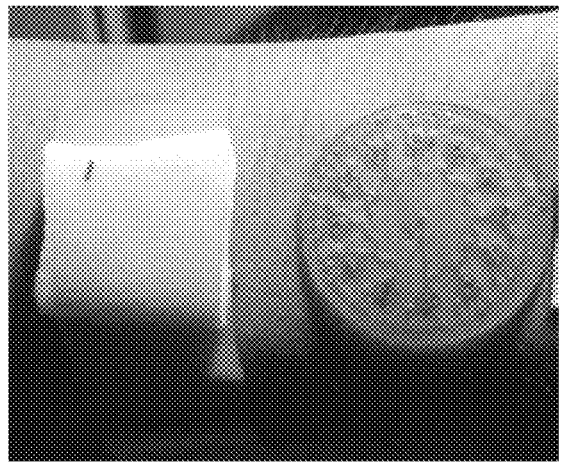
FIG. 34. Sweat rate measurement test. Top panel shows an exemplary device for calculating the sweat rate from conventional method and chrono-sampling device. Bottom panel illustrates enhanced sweat in the skin around the area blocked by adhesive. The sweat rate can be measured by the chrono-sampling device and conventional method FIG. 35. Overall view of the device illustration and optical image. (A) The exploded structure of device. (B) Assembled device, and logical operation. (C) The expansion of unit logical channel, and chemical, and mechanical functions. Arrows indicate the sequence order of sweat flow.
Figure 34:
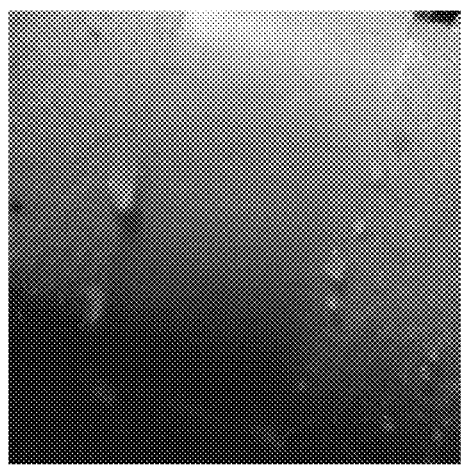

In situ chrono-sampling from the skin and chemical analysis of captured sweat samples: Human testing involved evaluations on volunteer subjects during running exercises and sessions in a sauna room. A formulation of $CoCl_2$ in polyhydroxyethylmethacrylate (pHEMA) coats the center regions of the chambers to produce a color change upon contact with sweat, thereby facilitating visualization of the filling process. For a representative running test, the first chamber filled after 8 min 20 s and the last chamber filled 10 min later. In a sauna, the first chamber filled after 13 min 33 s and the last chamber filled after 8 min 30 s. in both cases, the sweat rate increases with time and the time for filling each chamber after the first is less than one minute. In opening area (2 mm in diameter) of the adhesive, there are approximately 5 sweat glands.[39] In the running exercise, the average sweat rate over the first six minutes is 0.50 μl/min/gland and increases to 0.63 μl/min/gland. In the sauna, corresponding values are 0.54 μl/min/gland and 0.88 μl/min/gland. The initiation of perspiration is delayed in the sauna. Also, the initial sweat rates are similar in both conditions. But, the increase of sweat rate with time is high in the sauna. These values are tens of times higher than the rates from studies with conventional techniques (FIG. 34 top panel).[40] The increase of the sweat rate in the device is perhaps from the side effect of blocked region by adhesive film.[41] We find that there is more sweat in the skin around the area blocked by adhesive tape (FIG. 34 bottom panel). In the device, there is 3 $mm^2$ opening hole for sweat enters to the microfluidic channel and the other region about 700 $mm^2$ is covered by adhesive. To remove the enhance sweat collecting rate in the device, the adhesive region around the collecting region should be reduced. For that we design a different design to guide the sweat from the out of collecting region (FIGS. 27*c* and 32*a*). Using the device, the sweat rate from the chrono-sampling device is similar with the result from conventional method.

Centrifugation and extraction of samples from the extraction chambers of devices without $CoCl_2$/pHEMA allows mass spectrometer analysis of the concentrations of key biomarkers. This centrifuge approach does not allow analysis of glucose, urea, calcium and magnesium because microliter sample volumes with analytes at physiologically relevant ranges of concentration fall below limits of detection. For devices mounted on the forearm, samples collected after a running exercise indicate a systematic decrease in lactate concentration for chambers 1-9, followed by a slight increase for chambers 10-12. The concentration of sodium remains constant until chamber 6, decreases for chamber 7 and then increases again throughout. The decrease in concentration of lactate is consistent with the known dilution effect with increased sweating.[19] The overall concentration of lactate is higher for sweat generated by sauna exposure compared to running, and the reverse trend applies for sodium; both observations are consistent with previous studies using primitive sweat harvesting techniques.[6] The applicability of the epidermal microfluidic systems to locations across the body allows, as an example, comparisons of sweat from forearm, thigh, back and chest. Sodium and lacteal is more concentrated in the sweat collected from the chest and forearm, respectively, this agrees with data from other researchers.[39, 42, 43]. The data reveal no substantial differences in potassium concentration for these body positions. Interestingly, in all cases, peaks in concentration often occur at chambers 2 or 3, corresponding to the initial stages of sweating. This result might be explained by differences in biomarker concentrations between sweat stored in the glands and newly generated sweat. Alternatively, these changes indicate underlying physiological variations. Previous technologies, due to their lack in volumetric and/or temporal precision, do not allow observation of subtle effects such as these. Even the most sophisticated wearable electronic systems for sweat analysis do not separate the sweat with time, such that sweat released at different times mixes together at the point of measurement [10-16].

FIG. 29 provides in situ perspiration analysis from various body positions during running exercise and thermal exposure in a sauna. Chrono-sampling of sweat generated on the forearm during a running exercise under constant load (a) in thermal exposure at 56° C. (b). Cobalt (II) chloride dissolved in pHEMA and loaded into the devices aids in visualization of the filling process. Chemical analysis of lactate, sodium and potassium in the sweat extracted from a chrono-sampling device mounted on the forearm during a running exercise (c), from forearm (d), thigh (e), back (f) and chest (g) in thermal exposure. h) Regional variations of biomarker concentrations in sweat (lactate, sodium and potassium) collected from different body positions; chest, thigh, forearm and back.

In summary, this example introduces a soft, thin, skin-compatible, or 'epidermal', microfluidic device platform for time sequenced capture, storage and retrieval of microliter volumes of sweat. A key advance is in the development and use of microfluidic capillary bursting valves tailored to operate in a range of pressures commensurate with those naturally generated by sweat glands in human skin. Trials on volunteer subjects in various scenarios and regions of the body reveal temporal and spatial changes in the concentration of key biomarkers. The results demonstrate interesting time-dependent processes of relevance to exercise physiology and health/wellness more generally. Combined use of these platforms with colorimetric schemes for chemical sensing and with epidermal electronic components provide a broad range of engineering options in the design of advanced systems of use for personal and clinical use cases.

A microfluidics system is designed as suitable for quantitative colorimetric detection of chloride in sweat which is one of sweat biomarkers can predict dehydration when in the vigorous exercise and thermal condition. For the accurate detection of chloride, chloride assay solution based on the competition reaction of TPTZ chelation was modified to be used for raw sweat in situ. And two valves for the quantitative analysis and chrono-sampling are introduced in the microfluidic system. One is selective SAP valve which can close the channel when the flow of sweat is reached to the point of valve, and the other one is hydrophobic valve at which the sweat flow in microfluidic channel can select its direction by the hydrophobic resistance. The quantitative analysis using the device showed change of biomarkers in time course in human study, and should be utilized at the healthcare studies.

When the TPTZ has chelation with ferrous ion, the solution shows bluish color which is between 400-450 nm wavelengths. And the intensity of color development is concerned with the quantity of TPTZ chelation on the ferrous ion. Chelation is a kind of affinity competition, and if there is other ion substance which has strong affinity compared to chelating ion, TPTZ should migrate to the preferred ion. Mercury ion is more preferred than ferrous ion, and TPTZ would make the chelation with mercury ion when both mercury and ferrous ions are in the same solution. The solution shows no color and would be remained as transparent solution. It means almost TPTZ has chelation with mercury ion. Chloride has strong ion interaction with mercury which is stronger than the chelation of TPTZ. If chloride ion is added into the solution containing TPTZ, ferrous ion, and mercury ion, then, TPTZ chelation with mercury ion would be migrated to the ferrous ion, and bluish color intensity would be increased as the chloride concentration increases in the solution system. In the case of the raw sweat assay, the competition reaction may not be as effective as increase of all reactant concentration. Then, the competition reaction of TPTZ chelation should be re-designed as it is acceptable for the corresponding concentration of chloride when the raw sweat is directly used.

The microfluidic system is expected to have good performance at capturing and storing of sweat as soon as excreted from sweat gland. Conservation of sweat properties is very critical for sweat research because sweat is easily evaporated and contaminated as its own function. Thus, the strategies that capturing the sweat as soon as perspiration from sweat gland in epidermis have potential value. In the conventional study of sweat, patch type with either cotton or sponge to collect sweat have been used, and some kinds of electrochemical patches developed currently also limited in the patch type device which must be followed the chance of exposure to atmosphere which can induce evaporation, and contamination. The microfluidic system is not exposed to outside condition, and can be stored for relatively long time after sampling. In terms of storage with property maintaining, microfluidic system on epidermis is excellent. But there may be several drawbacks for precision analysis of sweat in situ if the colorimetric analysis paper is on the microfluidic channel in which sweat flows. The colorimetric analysis based chemical and enzymatic reaction is very sensitive for the volume or mass ratio of the reactant involved in the color expression reaction. Continuous flow of sweat in the channel can be an inappropriate condition for stable color development which is maintaining of the developed color. As the flow of sweat is ongoing, the colorimetric materials in the filter paper matrix should be washed out and developed colors would be diluted. It means the quantities of reactants containing biomarkers in sweat need to be controlled and conserved to be shown as same color index after color development. Then, microfluidic channel should be designed to support accurate color development and color maintaining.

Also, sweat composition is continuously changed as the subject gets in the situation of exercise or thermal condition. Then, chrono-sampling concept would be needed to see the change of sweat contents in time sequence. In nature, the manner of channel flow would be divided when it meets branched channel, and the dividing would be continued whenever it meets branched channel if the channel has several reservoirs which branched from the main stream channel. Finally the information of sweat in flow may be mixed with former and later flow, and be interfered. Introduction of microfluidics may helpful for the concept of sampling in time sequence.

For the precision analysis of biomarkers of sweat in time sequence, various strategies were integrated in the microfluidic device. The competition reaction of TPTZ chelation for chloride assay was designed for raw sweat analysis considering the affinities between $Fe^{2+}$ and $Hg^{2+}$. The instabilities of color development as increase of total concentration of ions also treated with the effect of surfactant and other ions. L-lactate assay cocktail was also modified in the ratio of enzymes and dyes for raw sweat analysis. Furthermore, several mechanical functions containing two key valves in microfluidics which were devised and integrated to maximize the effect of microfluidic system on the quantitative analysis of raw sweat. Poly sodium acrylate which is a kind of super absorbent polymer (SAP) was introduced for selective valve which can vent the air and block the leakage of sweat from the channel in same time. Also direction selecting valve using hydrophobic/hydrophilic characteristics was used for time sequential sampling of sweat to see the difference of biomarkers in time course. Finally, human tests were conducted with instrumental analysis to calibrate the quantitative analysis of biomarkers.

Figure 35:
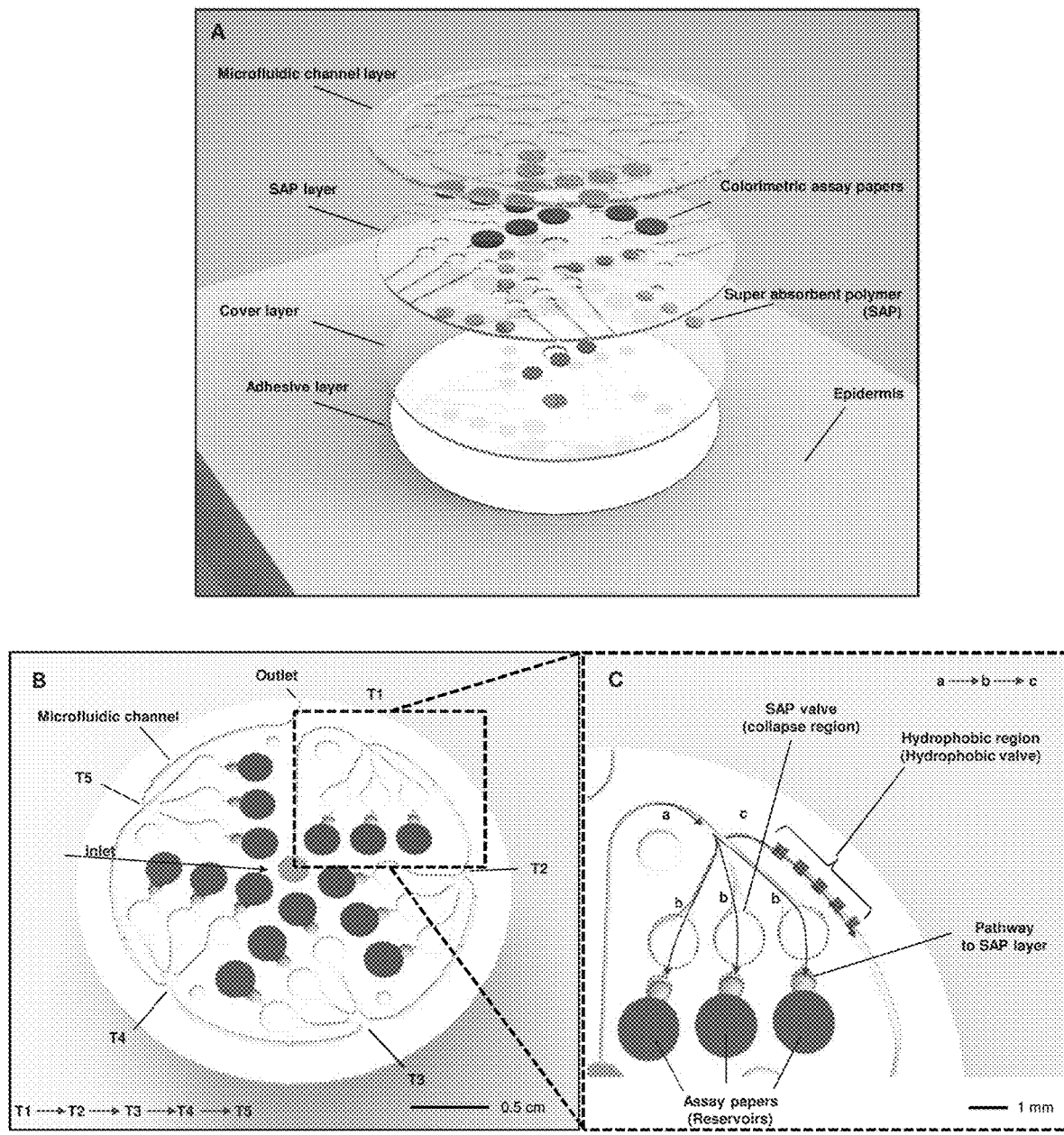

Skin-compatible microfluidic device for biomarker assay in time course: The device is comprised with several functional parts which are engineered using chemical and mechanical ideas to achieve accurate biomarker assay in perspiration. It has five different time points for sweat chrono-sampling and each of the time points has three reservoirs either to store collected sweat samples or to analyze biomarkers in colorimetric assay. FIG. 35 shows the overall view of microfluidic device design. The microfluidic channel system is structured in a double layer as the function of SAP valve which is selective valve to block the vent when sweat flow is reached at the valve point (FIG. 35a). The PDMS molds which are cured by soft-lithography are aligned and stacked up as flipping over as the channel side faces down, and bottom layer of ~200 μm thickness covers the channels of SAP layer. Also there is a piece of film which character is flexible but not stretchable on the SAP valve point of the bottom side to support and concentrate the swelling force toward upside of device. The inlet of microfluidic channel which is bottom side of the device should be anchored on the epidermis strongly and tightly because the device is designed as passive system which can be driven by the pressure of pumping up from sweat gland, and once the sweat is pumped from sweat gland, all system can be operated toward one orientation of inlet to outlet with filling up the reservoirs located along the main stream flow in series. Then, the anchorage of inlet on the sweat gland is very important to operate this device, and special adhesive for medical use is introduced. The fabricated device can be stretched, and is compatible with the skin shape and movement. The skin-compatible property make the device is available in the exercise environment in which vigorous movement should be followed. Also designed chemical and mechanical factors supported the accurate biomarker assay in situ.

FIG. 35b is the illustration of assembled device. Dimension of the device is 30 mm of diameter, 100-200 μm of channel width, ~300 μm of channel depth, 2.4 mm of single reservoir diameter, and ~500 μm of total device thickness. The microfluidic system can store total ~40 μL of sweat and ~6 μL can be stored for one time point. Once the reservoirs are filled up with sweat, inlet and outlet would be closed to prevent contamination and mixing by SAP valve and all reservoirs in each time points (T1-T5) would be filled up in the chrono-sampling manner. One time point station is consisted with hydrophobic valve, three reservoirs to analyze sweat, and three SAP valves for each reservoir (FIG. 35c). The reservoirs are used for colorimetric assay chamber, and it can be designed to use as sweat storage chamber without colorimetric assay paper. The device was also designed as chrono-sampling manner. The red arrows in the FIG. 35c indicate the flow order in time sequence. The sweat flow comes to the inlet of T1 point, it goes to the reservoirs at first, and never goes to next time point by hydrophobic valve unless T1 point is not filled up with sweat. In the process of filling up, the three colorimetric assay papers get wet and present the condition of corresponding quantities of biomarkers in sweat at that time moment. This flow manner would be repeated in the series of reservoirs on the device.

Chemical design for accurate and stable color development, and image processing: Human sweat contains around 50~100 mM concentration of chloride as the subjects are in the environment of exercise or thermal condition. Usually TPTZ method is conducted around 1 mM chloride concentration, and the color development could be observed at the range of chloride concentration of the sample. And the development of color could be calculated as color intensity or converted to the absorbance measuring from spectrophotometer. To assay high concentration chloride, total concentration of assay solution based on TPTZ method should be increased as corresponding quantity of chloride in the sample of raw sweat. But high concentration of complex solution containing various ions showed some issues about interference and unstable color development because of physical space saturation for the interactions of ion molecules in the limited solution volume. The complex of TPTZ chelation molecule must shows dipolar behavior and the distance of the complex which emit bluish color would be reduced in probability, and as closed the mercury ion and TPTZ chelated ferrous ion, TPTZ chelation would get destabilized, and finally the bluish color would be lost. Then, once the color has developed, the color index was easily changed as time. The TPTZ competition system might be affected as the increase of the competition ions. Though TPTZ is liberated from mercury as chloride is added, high concentration of mercury could still affect the chelation of TPTZ with ferrous ion and the changed solution color could not be maintained, and get dilute as solution stabilized. Then color development gets destabilized as total solution gets stabilized when high concentration of assay solution is used. Then, some stabilization agent was introduced. Other ions which do not affect the TPTZ chelation should be contained to buffer the effect of competition ions and should act as it secures physical space of molecules in the limited solution.

Figure 36:
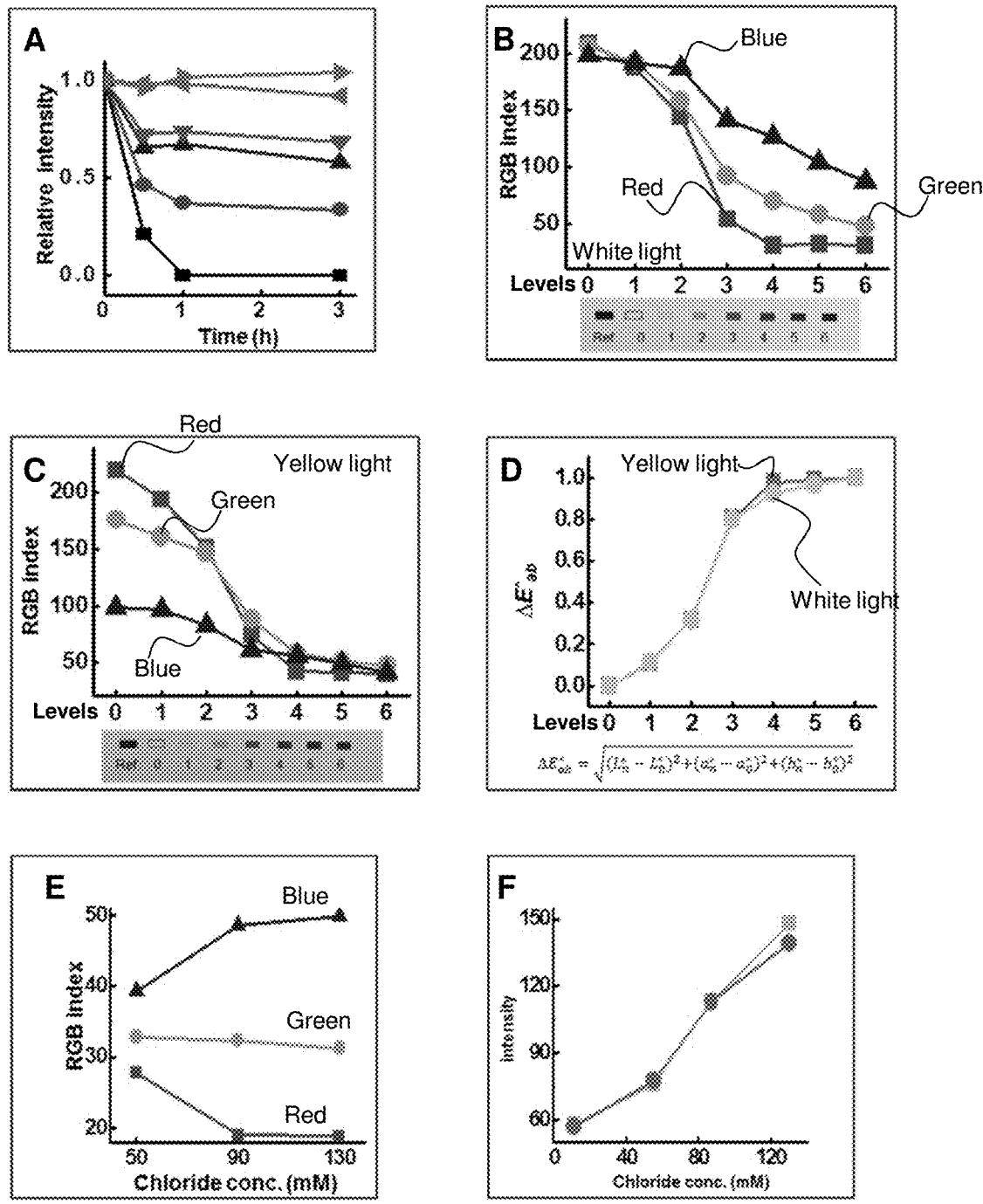
FIG. 36. Quantitative colorimetric assays. (A) The effect of Tween 80 on the stabilization of color development in TPTZ competition reaction for chloride assay. (B) Color index of blue color development under white light source. (C) Color index of blue color development under yellow light source. (D) Comparison of (B) and (C) after normalization of the RGB index using eq. 1. (E) The calibration curve of RGB index (up), and normalization (middle) and the optical color samples (bottom) for quantitative analysis of chloride. (F) Plot of intensity vs. chloride concentration (mM).

Also there are some issues of TPTZ solubility in water based solution. TPTZ is insoluble in water, and stock solution is usually prepared added into methanol. Though pure TPTZ has insoluble in water, once it has chelation ligand, it seemed allows the solubility of ligand substance. But the chelation complex may show such a dipole effect, then, the complex has solubility and insolubility in the water in same time. Then surfactant should be effective to stabilize the difference of TPTZ solubility. Also the stabilization of TPTZ using surfactant induces the stabilization of color development. FIG. 36a shows the effect of tween 80 concentration on the stability of color development. Various concentration of tween 80 was tested. When the assay with raw sweat and designed ratio of assay solution was conducted without the surfactant, the color development was not maintained, and the color index of assay paper was gradually decreased as time course. But when the tween 80 was used with the same condition of chloride detection, the developed color showed fairly maintained at over 0.8% tween 80. And When 1% of tween 80 was used, the color was maintained by 24 h (there is by 3 h in FIG. 36a).

Color index of RGB value is changeable as environment of the light source for image capturing. FIG. 36c show the difference of RGV value when the same chloride calibration color is exposed to the different light color of white and yellow. The difference of the color index needs to be calibrated as the interference of various light sources. Then, CIE color calibration method was employed, which can correct the image from various light sources using white value standard. CIE L*a*b* color space is a three dimensional real number space that can incorporate both RGB and CMYK systems. Then, the complicating difference of color index could be described as converting into single index using Eq. XI. FIG. 36d is the comparison of color index conversion from the color image from white and yellow light source. The difference of color information under white and yellow light was converted as defined index, and it showed almost same values for the various levels of color development. FIG. 36e is the calibration curve for chloride assay in the raw sweat.

Mechanical strategies for accurate and stable color development: Color development which can be converted into as RGB index as the concentration of desired biomarker is based on the stoichiometry of chemical and enzymatic reactions. Then, the different quantities and ratios of the reactants can be shown as the particular color expression as the results of the reactions, and the control of reactants ratio, and quantity is the key point for the accurate color development. Well controlled assay solution containing the reactants was dropped on the filter paper, and accurate sweat amount must be sampled to be reacted with the reactants permeated in the filter paper. But the color development might be diluted and would show inexact information if the assay paper is on the continuous flow because the reactant in the assay paper might be washed out by the sweat flow. Then, the continuous flow should be stopped when the reservoir has filled up with sweat sample. Also the sampled sweat should be separated from main flow in same time to avoid mixing of sweat information between former and later sweat flows. Each reservoir has two pathway of inlet for sweat coming in from main flow of microfluidic device and outlet as air vent. And both pathway should be closed by selective valve to secure allocate amount of sweat sample. To realize the selective valve which can pass the air in channel but stop the flow, the microfluidic channel should be collapsed physically such as pneumatic valve. In the pneumatic valve operation, there are flexible thin layer between flow channel and particular air room at the valve point, and the channel side would be collapsed when the air pressure is increased as blowing air in the air room. The key mechanism of pneumatic valve is expansion of air room, and the selective SAP valve borrows the concept of some space expansion which can induce the physical collapse to close the valve logically.

SAP materials have the character of swelling up in gelation process when it meets the water based solution which is equal with the effect of space expansion. Furthermore, SAP is a powder in normal condition, and it can be used as vent though it filled a part of channel. Then, introduction of SAP can achieve not only the effect of a selective valve to block the sweat flow, but also the effect of pneumatic valve to close inlet point. FIG. 37a shows the design of selective SAP valve and FIG. 37b is that the selective SAP valve is activated. The valve is designed such a pneumatic valve which have collapse area and expanding area. And the expanding area is filled with SAP. It is beneficial to be bi-layer structure, and SAP layer is responsible for the Once the sweat fills the reservoirs up, both inlet from main stream channel and outlet for ventilation of air would be closed as the effect of SAP swelling. The reservoirs for one time point have double layer structure to realize the SAP valve. The sweat flow would come in from upper layer channel, and if the reservoir is filled up or the assay paper is wet by the pressure of incoming flow, the SAP would be activated to be swollen by absorption of sweat flow. The activation of SAP valve would finally induce the closing of ventilation channel, and the inlet channel also would be collapsed to be closed (FIG. 37b). Two actions of closing ventilation and collapse of inlet would not be occurred in same time, but as the SAP is gelated, it would be swollen and the collapse would take place in short time.

Sweat sampling in time sequence: As the continuous change of sweat composition over time, chrono-sampling concept should be integrated. FIG. 38a is the concept of chrono-sampling that if there is branched micro channel, and flow would select its preferred property such as hydrophobic or hydrophilic characteristics of channel surface. In case of sweat, it is biofluid based on water, and it would select relatively hydrophilic channel when the flow meets the branched channel in which one is treated as hydrophilic, and the other one is hydrophobic. Once the flow select hydrophilic channel at the point of branch, it never go to the hydrophobic channel (FIG. 38b). But the end of hydrophilic channel is blocked, the inside pressure of channel gets increased, and the pressure of flow would burst out though the hydrophobic channel at last. The selection of flow direction could be expressed as resistance, and at first, flow selected channel of less resistance, and as the resistance is increased for the blocking, the flow pressure overcomes the hydrophobic channel resistance (FIG. 38c). This simple concept should be utilized and employed to realize the flow direction selective valve, named hydrophobic valve in this study. The backbone structure of skin-compatible microfluidic device is PDMS, and OH group which acts as hydrophilic functional group is developed when it is exposed to the oxygen plasma. A procedure of PDMS surface modification is available. The original character of PDMS is hydrophobic, and the regions for hydrophobic valve should be masked conformally using PDMS and anti-adhesion agent. After expose to the plasma and relief of the masking, the masking region would be remained as the original hydrophobic region, and other part would be modified as hydrophilic. FIG. 38d shows the illustration of hydrophobic valve operation steps in time sequence. Each time point of the microfluidic device has same flow channel shape, and the operation steps would be repeated as the time points are filled up. When the flow comes to the first time point (T1), hydrophobic valve would stop the flow and the sweat flow would be divided to three branched channel and go through the SAP valve points. If the reservoirs are filled up with the sweat sample, and selective SAP valve is activated, the total resistance of T1 for the sweat flow would be increased and the sweat pumping pressure would overcome the resistance of hydrophobic valve. Then, the main flow will jump to next time point. As the effect of hydrophobic valve and selective SAP valve, finally the reservoirs at all points (T1-T5) would be filled up as the chrono-sampling manner (FIG. 38e). FIG. 38f is the results of fabricated microfluidic device which have the concepts of hydrophobic valve and selective SAP valve. Blue color dyed artificial sweat was pumped into the device. The pressure of artificial sweat pumping was ~300 Pa which is derived from potential energy of 3 cm heights and the results showed the chrono-sampling manner of sweat flow as we designed.

FIG. 38g is the effect of pumping pressure which drives the microfluidic device. The device is designed as passive valve system, and the filling up time for five time points depend on the pumping pressure at inlet of microfluidic channel. The pumping pressure from sweat gland is related with the sweat excretion rate, and the correlation with the pressure and sweat excretion rate would be proportional (ref.). Then, the pressure is relatively high, the flow rate would be rapid, and filling up time would be shortened. On the other hand, at the low pressure, the filling up time would be extended. Also the device may be modified to be extended by increasing channel size between time points as buffer area which is as the need of sweat research. Also limited range of the pumping pressure could be controlled by changing the inlet size of the microfluidic device on the bottom cover layer. The FIG. 38h is the effect of inlet size on the sweat capturing time. The inlet size test was performed on the real skin. Subjects experienced the thermal condition of over 40° C. temperature of thermal condition.

Preparation of chemical and enzymatic assay agent, and device fabrication: Polysodiumacrylate was determined as SAP material and synthesized as the method of Kabiri et al. (2003). Glacial acrylic acid monomer (Sigma Aldrich) was neutralized with 55% KOH, and 2 mL Ammonium sulfate (37.5 g/L) and 4 g sodium bicarbonate were added into the acrylic acid solution. N, N'-methylenebisacrylamide, fast swelling agent (Sigma Aldrich) of 2 mL Sodium metabisulfite (31.5 g/L), cross linker of 2 mL were added, and viscosity was increased for the gelation. After that, the gel was spread over the oven tray, and dried at 70° C. for 24 h. Dried material was ground and meshed with No. 000 sieve (000 μm mesh size).

Chloride assay agent was prepared based on the method of 0000 et al. TPTZ was resolved in methanol to be 0000 M concentration. $HgSO_4$ and $FeSO_4$ solution was prepared in 10 mM concentration. [More Chloride assay method]

Filter paper (Whatman No. 1) was used as assay agent matrix after punching in 2.5 mm diameter. Exact amounts of 2.6 μL solution for chloride assay and 2 μL for lactate assay were dropped on the filter paper of 2.5 mm diameter and dried at the ambient room temperature for 1 h. In the case of l-lactate, additional enzyme cocktail of HRP (20 mg/mL) and LOx (60 mg/mL) are dropped in 1:2 v/v ratio. Also pH assay paper was purchased, and punched to be 2.5 mm diameter to insert the reservoir in microfluidic channel.

Fabrication of skin-compatible microfluidic device: To generate soft and flexible backbone for skin-compatible microfluidic device, soft lithography of replica molding process was conducted which make mold of particular channel shape of polydimethylsiloxane (PDMS; Sylgard 184, Dow Corning; mixed at a 23:1 ratio of base to curing agent by weight) from mold cast of silicon wafer. For that, photolithography was performed. Cleaned silicon wafer was coated with KMPR 1010 (MicroChem, Westborough, Mass.) which is negative photoresist, and the coated wafer was exposed to the UV with channel designed mask for 30 sec. Developed wafer was etched using deep reactive-ion etching (STS Pegasus ICP-DRIE, SPTS Technologies Ltd, UK) to be 300 μm depth microfluidic channel. After etching, the mold cast was coated with polymethylmethacrylate (PMMA) at 3000 rpm spin coater for 30 sec, and curing at 180 for min was followed. The conditions of casting on spin coater were that 250 rpm for channel layer, and 400 rpm for SAP layer. After 30 sec spin coating at each condition, curing was followed at 70° C. for 4 h. Masking of hydrophobic valve spot for each time point on channel layer was conducted using PDMS after anti-adhesion treatment. Prepared SAP material was loaded at SAP valve point on the SAP layer, and SAP layer and bottom cover was bonded after oxygen plasma treatment. Channel layer was also treated with oxygen plasma, and masking material was removed. Bonding of channel layer with SAP layer assembly was followed after loading of colorimetric dye and color reference. Adhesive layer was assembled on bottom cover layer, and the assembly was punched as 30 mm diameter.

Data process, image process and instrumental analysis: After subject test and pumping test, the photo of device was taken, and the black and white balance for the image was performed following the RGV values of colorimetric detection for all biomarkers were obtained using Adobe Photoshop program. The values were then converted to CIE L*a*b* values, and color difference was calculated using following equation $$\Delta E_{ab}^* = \sqrt{(L_n^* - L_0^*)^2 + (a_n^* - a_0^*)^2 + (b_n^* - b_0^*)^2} \quad \text{(XI)}$$

Where L* is lightness, a* is green to red scale from negative to positive values, and b* is blue to yellow. L*n, a*n, and b*n denotes the developed assay's values at level n, and L*0, a*0, and b*0 are the values for a white reference paper.

Human study: On body test for human study for was performed with Air Force Research Laboratory (Write-Patterson Air Force Base, Dayton, Ohio). The subject experienced the environment of marching condition as wearing full battle gear including a helmet, Kevlar vest, 50 lb. pack, and M4 rifle on uniform. The ruck march was conducted on a treadmill protocol with two inclines and speeds of easy and moderate. Before downing the gear, Wescors, sweat sampler and skin-compatible microfluidic device were placed on the right forearm, and they are covered with a compression arm sleeve. The march was maintained until the subject was exhausted with dehydration, and it was approximately 1.5-2 h march.

Figure 2:
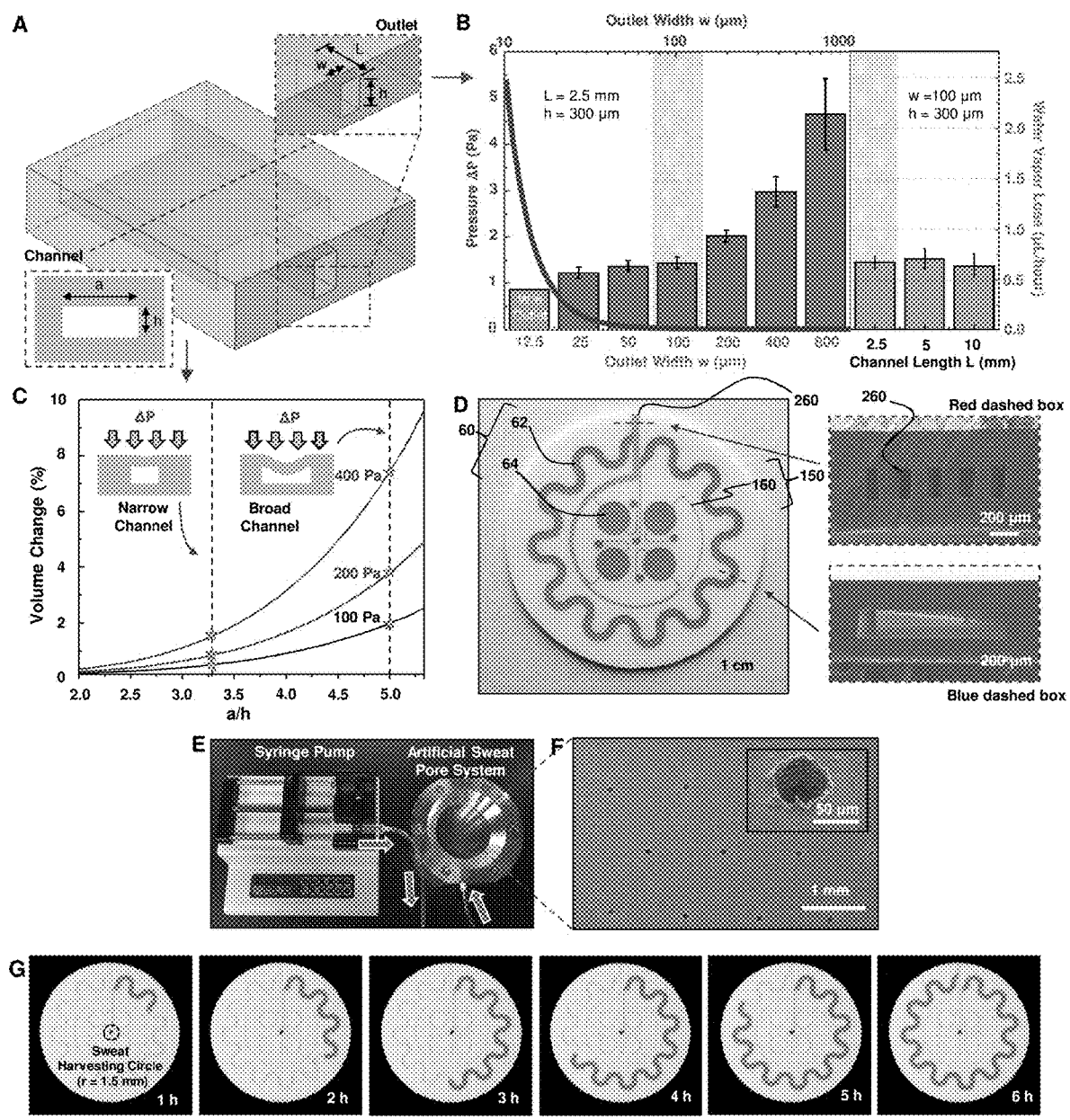
FIG. 2. Analysis of key design features and demonstration of epidermal microfluidic patches. (A) Sketch of the channel geometry for numerical calculation. The blue and red dashed boxes highlight the dimensions of the serpentine and outlet channels, respectively. (B) Experimentally determined water vapor loss from a microfluidic channel as a function of width (w) and length (L) of the outlet channel with a fixed height of 300 μm. Inner pressure variation as a function of the outlet channel width was also determined from the model (red line). The orange shading highlights the optimal channel geometry. Data are presented as the average value, and error bars represent standard deviation (n=3). (C) Model prediction of the change in volume of the serpentine channel as a function of aspect ratio (ratio of width 'a' to height 'h' of the serpentine channel in (A), blue dashed box) under various pressures (ΔP=100, 200 and 400 Pa). ΔP represents pressure difference between the inside and outside of the serpentine channel. Dotted vertical lines show two representative aspect ratios (10:3 and 5:1). (D) Picture of a fabricated epidermal microfluidic structure corresponding to the theoretical results and cross-sectional scanning electron microscope (SEM) images of the outlet (red dashed box) and serpentine (blue dashed box) channels. (E) Experimental set-up of artificial sweat pore system. (F) SEM images of the polyimide (PI) membrane mimicking human sweat glands. (G) Demonstration of hydrodynamic fluid flow through the microfluidic device using the artificial sweat pore system at the rate of 5.5 μL/h.

Exemplary devices: Referring to FIGS. 1 (panels A-D), 2 (panel D), and 3 (panel A), device 10 may be affixed to a surface or epidermal layer 45 of skin 40 to handle a biofluid, indicated by arrow 20 representing biofluid released from the skin, including sweat. Biofluid 20 may include one or more analytes and/or one or more biomarkers, such as lactate, pH, or chloride. Device 10 may include a functional substrate 30, which may be formed of a polymer, including PDMS, and may support a microfluidic network 150, biofluid collection structures 60, and one or more sensors 50. FIG. 2 panel D shows microfluidic network 150, supported by functional substrate 30, with microchannels 160 in fluid communication with biofluid collection structures 60, including at least one microfluidic channel 62 and a reservoir, illustrated as four reservoirs or chambers 64. Biofluid collection structures 60 may form at least a part of microfluidic network 150. Biofluid collection structures 60 and sensor(s) 50 may be positioned on a support surface 35 of functional substrate 30. One or more inlets 130 may be used to convey, transport or exchange biofluid 20 to sensor 50 released from skin surface 45, with inlets aligned in each of the relevant layers. An adhesive layer 140, having openings or harvesting areas 145 positioned to fluidically align or correspond with inlet(s) 130. Microfluidic network 150 may further include outlets 260, such openings and/or membranes. Device 10 may further include a cover or capping layer 190, which may be formed of a polymer, including PDMS.

FIG. 1 panel A further illustrates control and/or communication means for interfacing or interacting with, including broadly speaking, actuating, device 10, including as desired, for example, an external device such as a smartphone or tablet computer. Interfacing unit may include a coil 340, an actuator 292 (for either controlling electronic circuitry and/or a physical parameter exerted on a skin surface, also described herein as an NFC chip), a transmitter, a receiver, and/or a transceiver. Interfacing unit may provide NFC capability, such as by including in NFC electronics, such as an NFC chip and a near-field communication coil 340.

Figure 3:
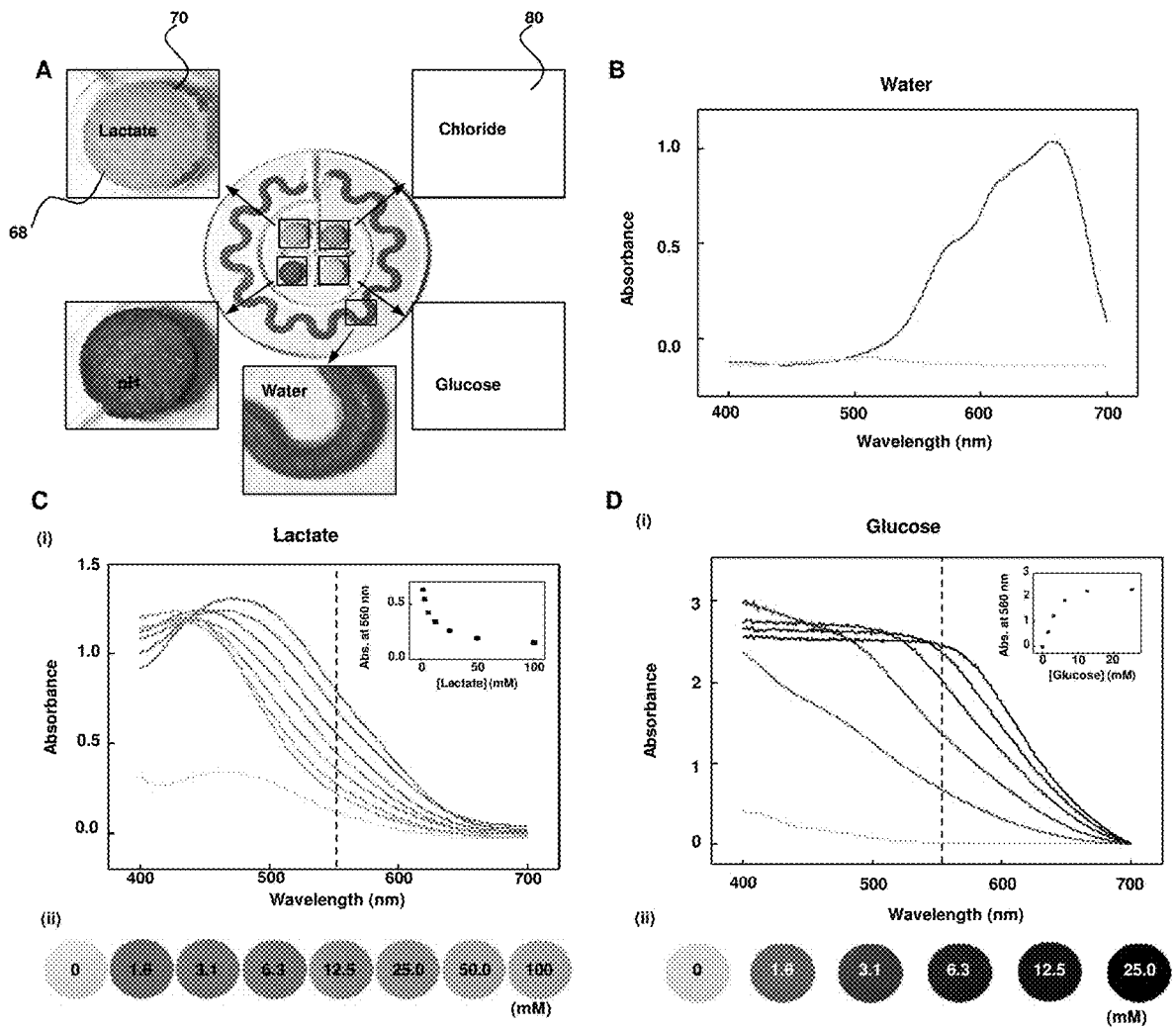
FIG. 3. Quantitative colorimetric analysis of markers in sweat. (A) Colorimetric detection reservoirs that enable determination of (B) total water (sweat) loss and concentrations of (C) lactate, (D) glucose, (E) creatinine, (F) pH, and (G) chloride ions in sweat. (B-G) Corresponding quantitative analysis conducted by (i) UV-vis spectroscopy and (ii) optical images as a function of analyte concentrations. The presented color for (i) each spectrum corresponds to (ii) the color exhibited at the detection reservoir in the device. The insets in the spectra provide calibration curves for each of the analytes. The inset in (E) shows the response over a reduced range of concentrations.
Figure 3:
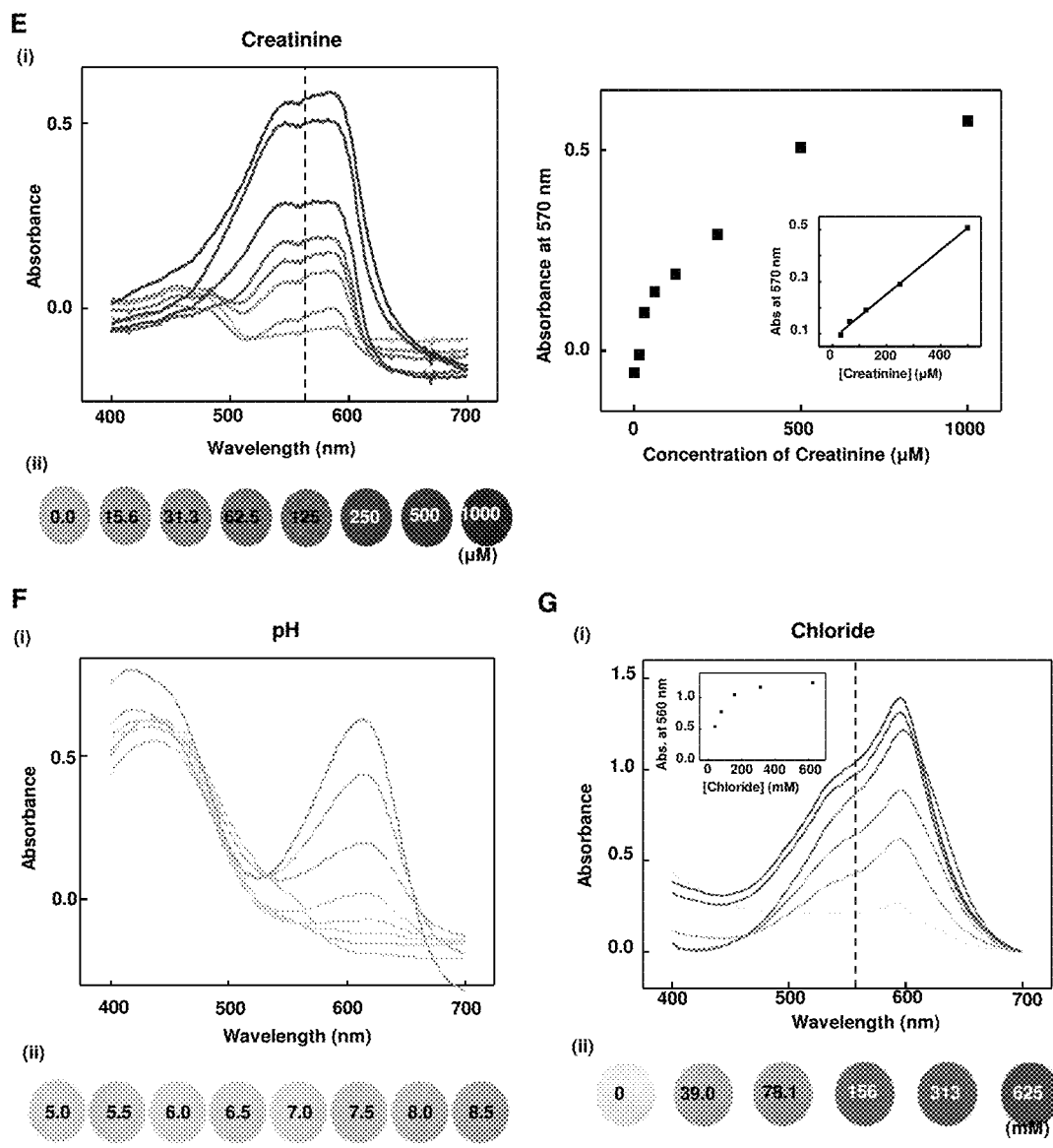

Sensor 50 may include a plurality of sensors, such as a first sensor 70 (FIG. 3, panel A, top left) and second sensor 80 (FIG. 3, panel A, top right). Sensors 70 and 80 may be used for determining concentration of one or more different analyte, or analyte concentration over different concentration ranges. Different sensors may be used to measure different biofluid properties. Sensors 50 may correspond to one or more colorimetric sensors 280. Colorimetric sensors 280 may include one or more indicator reagents 284, including color-responsive reagents 282, such as a colorimetric dye. Color-responsive reagent(s) 282 may be provided in a biofluid collection structure 60, such as microfluidic channel 62 or reservoir 64. A hydrogel 68 may be provided within a biofluid collection structure 60 to immobilize color-responsive reagent 282.

Figure 25:
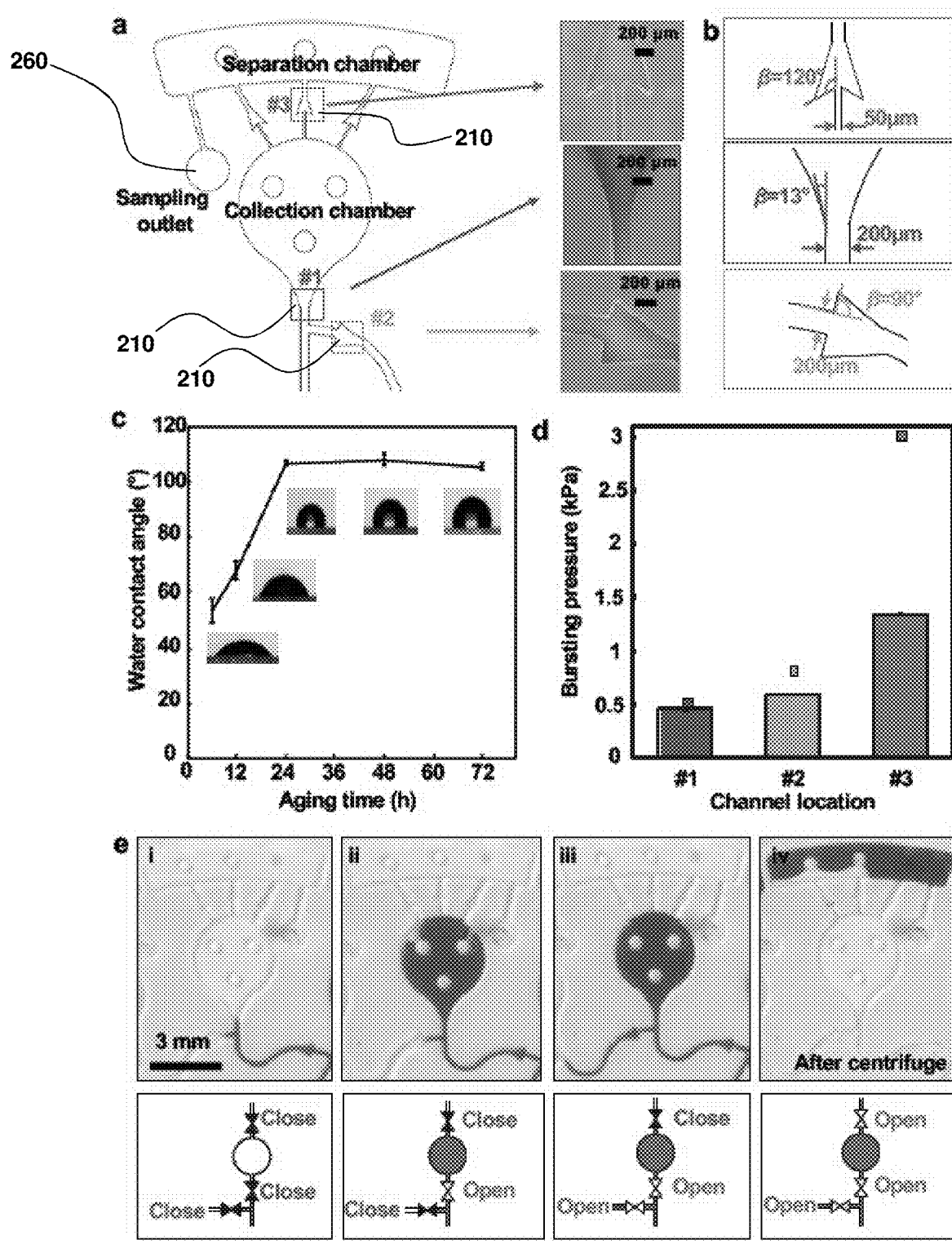
FIG. 25. (a) Detailed schematic illustration of a unit cell of a device, showing a collection chamber, evaluation chamber, sampling outlet and three capillary bursting valves (CBV) and SEM images of CBVs. (b) Sketch of capillary bursting valves with channel width and diverging angle indicated. (c) Measurements of the water contact angle of a PDMS surface as a function of time after treatment with an oxygen plasma. (d) Experimental results (bars) and theoretical values (square box) of capillary bursting pressures of CBV #1, #2 and #3 of a typical device. (e) Optical images and schematic illustrations of the operation of capillary bursting valves for chrono-sampling. (i) before entering the collection chamber ii) filling the collection chamber iii) flowing to next chamber iv) after centrifugation.
Figure 37:
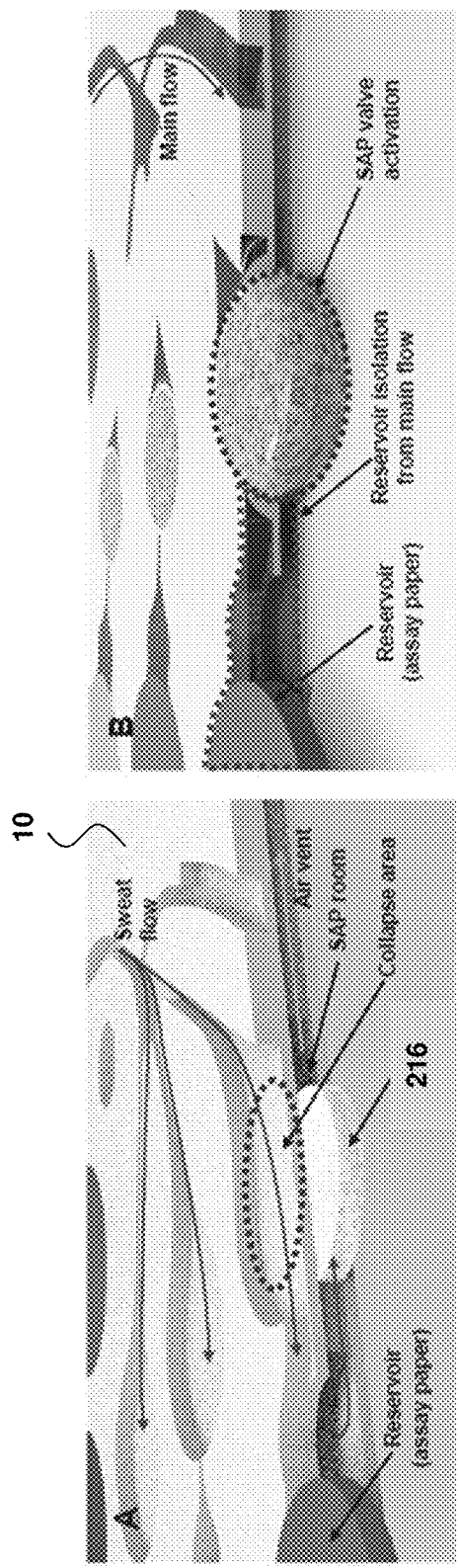
FIG. 37. Mechanical strategies to support accurate colorimetric assay. (A) The design of selective SAP valve, red arrows are the sweat flow. (B) The effect of selective SAP valve, red arrow is the sweat flow.
Figure 38:
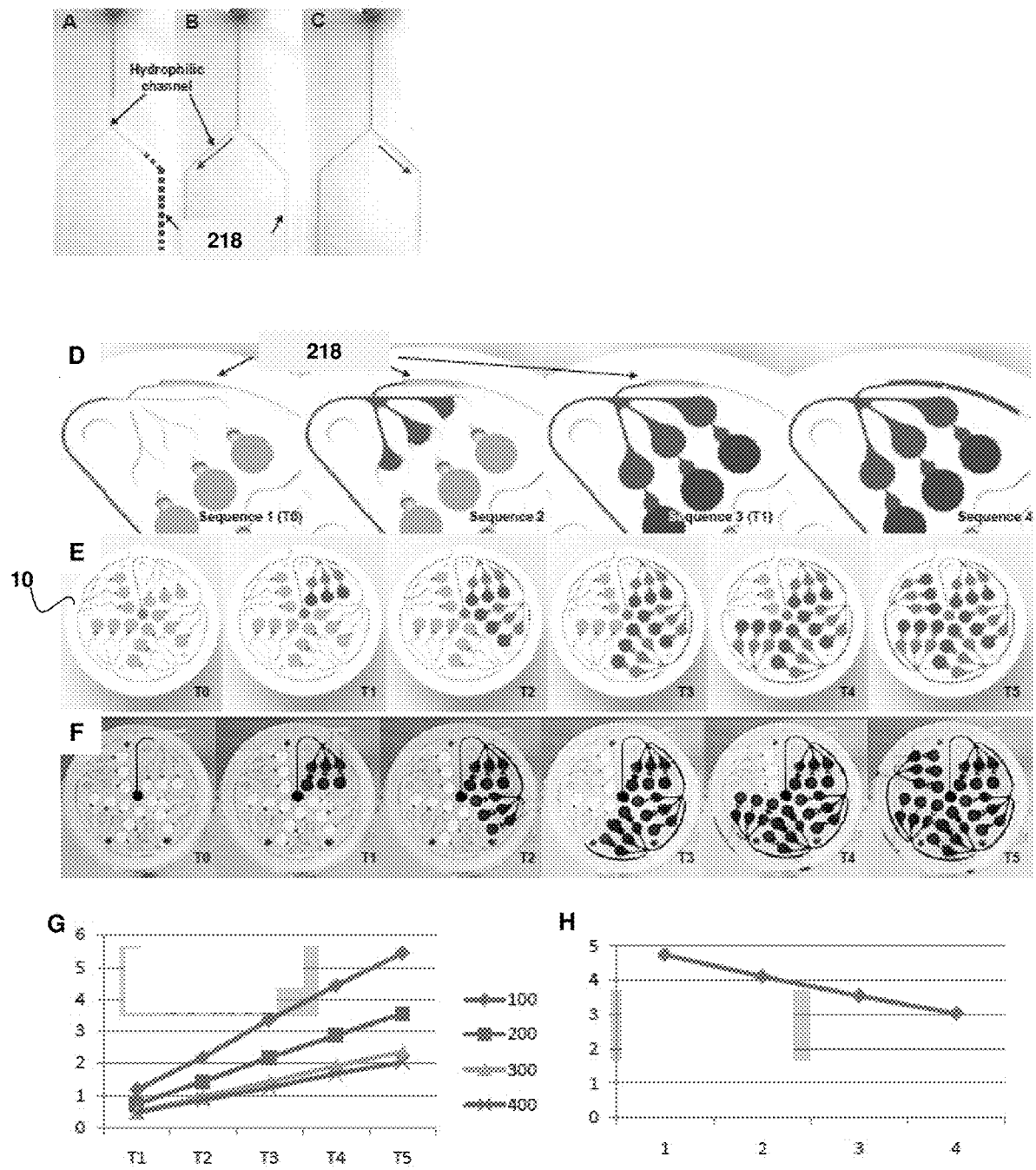
FIG. 38. Chrono-sampling of sweat. (A) Schematic experiment design for the direction selecting valve in microfluidics. (B) The effect of hydrophobic treatment for designated flow. (C) Chrono-sampling manner of the sweat flow in the microfluidics. (D) The operation steps in the time sequence. (E) Chrono-sampling of designated sweat flow using selective SAP valve and hydrophobic valve. (F) Optical image of the chrono-sampling in time course. (G) Effect of pumping pressure on the sampling time. (H) Effect of inlet size on the sampling time.
Figure 39:
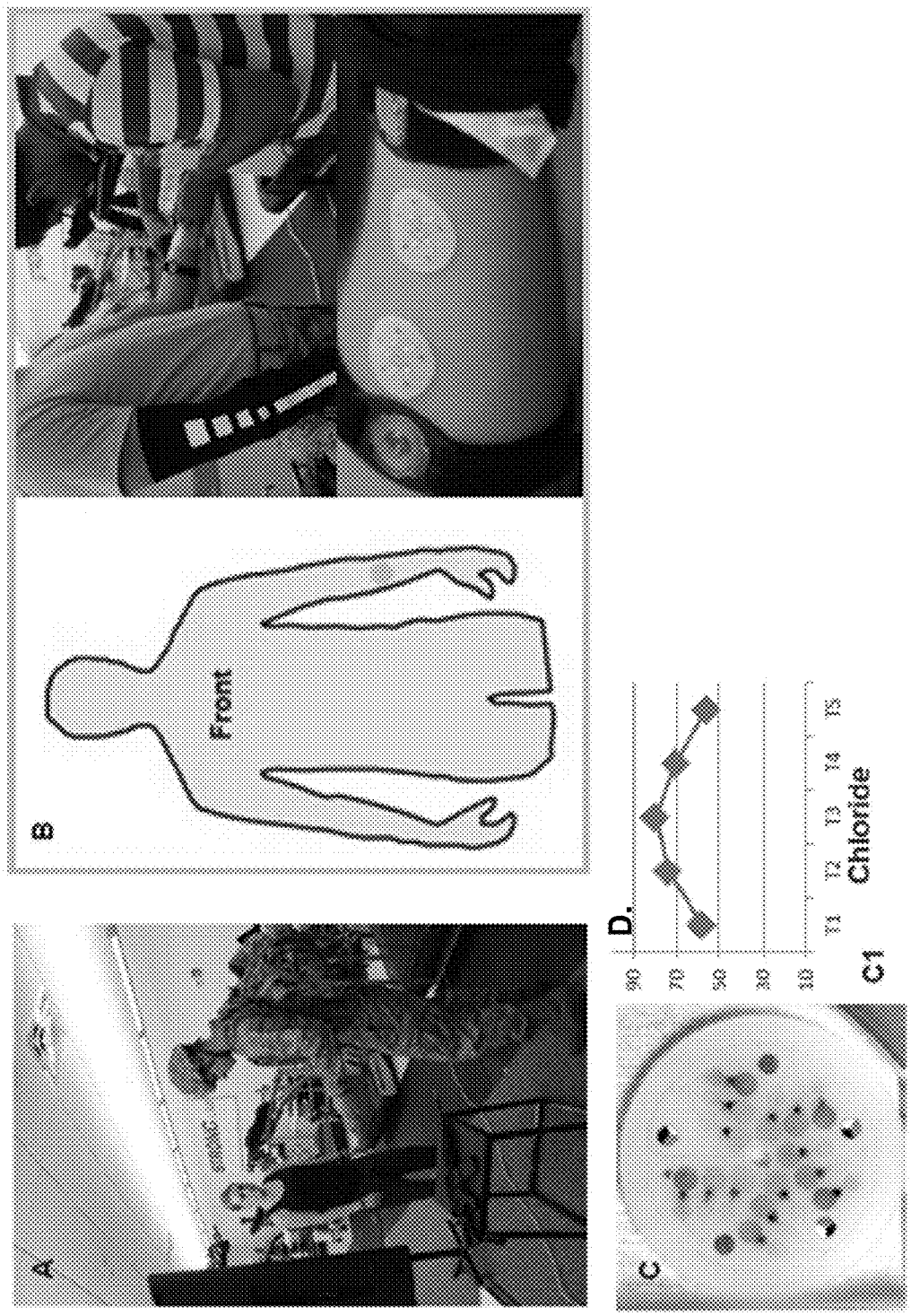
FIG. 39. Practical human study for detection of biomarkers in sweat in situ. (A) Picture of controlled room. (B) Illustration and pictures for sweat patch location on body. (C) The results of sweat assay in situ: The change of I-lactate (C1) (D) The result for subject 1.

FIGS. 24 and 25 illustrate a microfluidic network 150 having microchannels 160, reservoirs 200, and valves 210. Each of valves 210 is a passive valve or an active valve, and may be a capillary burst valve. FIG. 25 illustrates examples of various valves 210. The valves may include direction selective valves. FIG. 37, panels A and B, illustrates a valve that is a super absorbent polymer (SAP) valve. FIG. 38, panels A, B, and D, illustrates a valve that is a hydrophobic valve 218.

Figure 40:
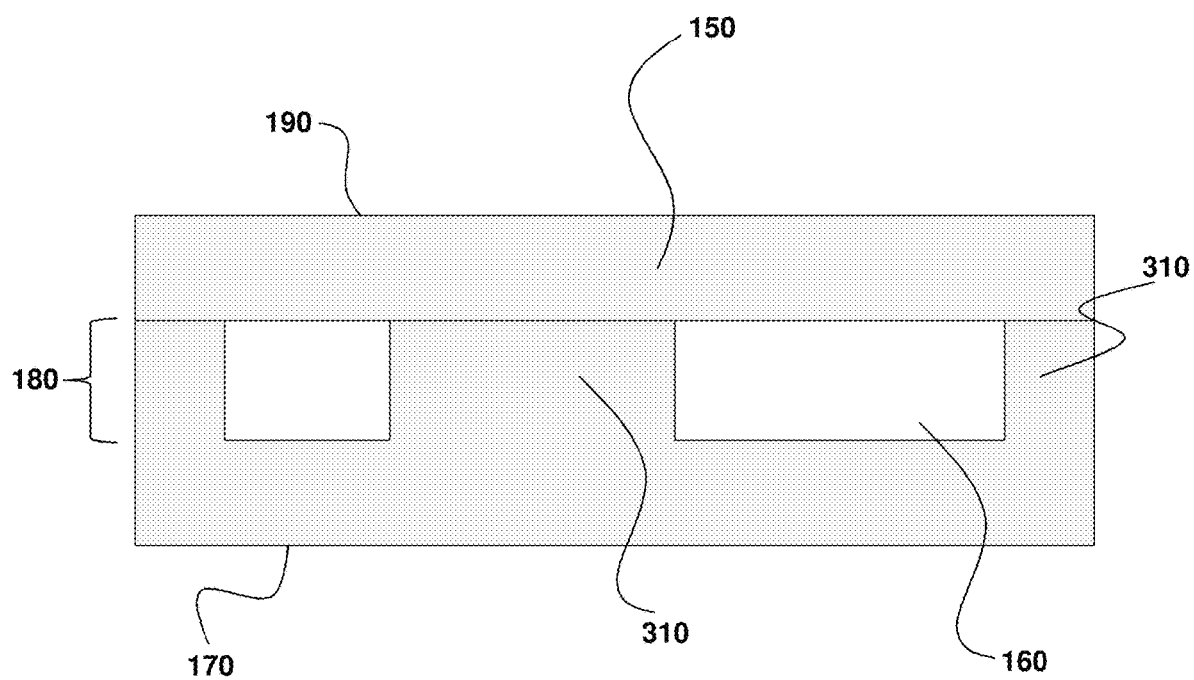
FIG. 40. An illustration of a microfluidic network having a first layer embossed on a substrate surface to provide relief geometry to define microchannels and a second layer that is a top capping layer.

FIG. 40 illustrates a microfluidic network 150 including a first layer 170 embossed with relief geometry 180, comprising relief features 310, to define microchannels 160. A second top capping layer 190 may be used to enclose the microchannels 160.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

The following references relate generally to fabrication methods, structures and systems for making electronic devices, and are hereby incorporated by reference to the extent not inconsistent with the disclosure in this application.

| Attorney Docket No. | Application No. | Filing Date | Publication No. | Publication Date | Patent No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Jul. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | | |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/585,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | | |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 216-06A US | 12/522,582 | Jul. 9, 2009 | — | — | | |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | — | — |
| 60-09 US | 12/778,588 | May 12, 2010 | 2010/0317132 | Dec. 16, 2010 | — | — |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 19-10 US | 12/916,934 | Nov. 1, 2010 | 2012/0105528 | May 3, 2012 | 8,562,095 | Oct. 22, 2013 |
| 3-10 US | 12/947,120 | Nov. 16, 2010 | 2011/0170225 | Jul. 14, 2011 | | — |
| 118-08 US | 12/996,924 | Dec. 8, 2010 | 2011/0147715 | Jun. 23, 2011 | 8,946,683 | Feb. 3, 2015 |
| 126-09 US | 12/968,637 | Dec. 15, 2010 | 2012/0157804 | Jun. 21, 2012 | | |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | | |
| 137-05A US | 13/095,502 | Apr. 27, 2011 | — | — | | |
| 216-06B US | 13/100,774 | May 4, 2011 | 2011/0266561 | Nov. 3, 2011 | 8,722,458 | May 13, 2014 |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277813 | Nov. 17, 2011 | 8,679,888 | Mar. 25, 2014 |
| 151-06B US | 13/228,041 | Sep. 8, 2011 | 2011/0316120 | Dec. 29, 2011 | | |
| 43-06B US | 13/270,954 | Oct. 11, 2011 | 2012/0083099 | Apr. 5, 2012 | 8,394,706 | Mar.12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100618 | Apr. 25, 2013 | 8,754,396 | Jun. 17, 2014 |
| 134-06B US | 13/441,598 | Apr. 6, 2012 | 2012/0327608 | Dec. 27, 2012 | 8,729,524 | May 20, 2014 |
| 28-11 US | 13/472,165 | May 15, 2012 | 2012/0320581 | Dec. 20, 2012 | | |
| 7-11 US | 13/486,726 | Jun. 1, 2012 | 2013/0072775 | Mar. 21, 2013 | 8,934,965 | Jan. 13, 2015 |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | | |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 125-12 US | 13/835,284 | Mar. 15, 2013 | 2014/0220422 | Aug. 7, 2014 | — | — |
| 30-13 US | 13/853,770 | Mar. 29, 2013 | 2013/0333094 | Dec. 19, 2013 | | |
| 213-07A US | 13/974,963 | Aug. 23, 2013 | 2014/0140020 | May 22, 2014 | 8,905,772 | Dec. 9, 2014 |
| 19-10A US | 14/033,765 | Sep. 23, 2013 | 2014/0092158 | Apr. 3, 2014 | — | — |
| 15-10A US | 14/140,299 | Dec. 24, 2013 | 2014/0163390 | Jun. 12, 2014 | | |
| 38-04A4 US | 14/155,010 | Jan. 14, 2014 | 2014/0191236 | Jul. 10, 2014 | — | — |
| 136-08A US | 14/173,525 | Feb. 5, 2014 | 2014/0216524 | Aug. 7, 2014 | | |
| 216-06C US | 14/209,481 | Mar. 13, 2014 | 2014/0373898 | Dec. 25, 2014 | — | — |
| 134-06C US | 14/220,910 | Mar. 20, 2014 | 2014/0374872 | Dec. 25, 2014 | | |
| 38-04F US | 14/220,923 | Mar. 20, 2014 | 2015/0001462 | Jan. 1, 2015 | — | — |
| 151-06C US | 14/246,962 | Apr. 7, 2014 | 2014/0361409 | Dec. 11, 2014 | | |
| 62-13 US | 14/250,671 | Apr. 11, 2014 | 2014/0305900 | Oct. 16, 2014 | — | — |

-continued

| Attorney Docket No. | Application No. | Filing Date | Publication No. | Publication Date | Patent No. | Issue Date |
|---|---|---|---|---|---|---|
| 56-13 US | 14/251,259 | Apr. 11, 2014 | 2014/0323968 | Oct. 30, 2014 | — | — |
| 60-09A US | 12/778,588 | Sep. 5, 2014 | 2015/0132873 | May 14, 2015 | — | — |
| 84-13 US | 14/504,736 | Oct. 2, 2014 | 2015/0141767 | May 21, 2015 | — | — |
| 213-07B US | 14/521,319 | Oct. 22, 2014 | — | — | — | — |
| 7-11A US | 14/532,687 | Nov. 4, 2014 | 2015/0080695 | Mar. 19, 2015 | — | — |
| 2-14 US | 14/599,290 | Jan. 16, 2015 | — | — | — | — |
| 71-07A US | 12/669,287 | Apr. 14, 2015 | — | — | — | — |
| 213-07C US | 12/398,811 | May 7, 2015 | — | — | — | — |
| 15-13 WO | PCT/US2014/015825 | Feb. 19, 2014 | WO2014/126927 | Aug. 21, 2014 | — | — |
| 128-13 WO | PCT/US2014/014932 | Feb. 5, 2014 | WO 2014/124044 | Aug. 14, 2014 | — | — |
| 8-14 WO | PCT/US2014/014944 | Feb. 18, 2014 | WO 2014/124049 | Aug. 14, 2014 | — | — |
| 35-13 WO | PCT/US2014/021371 | Mar. 6, 2014 | WO 2014/138465 | Sep. 12, 2014 | — | — |
| 54-13 WO | PCT/US2014/032848 | Apr. 3, 2014 | WO 2014/165686 | Oct. 9, 2014 | — | — |

Every formulation or combination of components described or exemplified herein can be used to practice the invention, unless otherwise stated.

When a group of substituents is disclosed herein, it is understood that all individual members of that group and all subgroups, including any device components, combinations, materials and/or compositions of the group members, are disclosed separately. When a Markush group or other grouping is used herein, all individual members of the group and all combinations and subcombinations possible of the group are intended to be individually included in the disclosure Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

REFERENCES FROM EXAMPLE 1

1. D. H. Kim, N. Lu, R. Ma, Y.-S. Kim, R.-H. Kim, S. Wang, J. Wu, S. M. Won, H. Tao, A. Islam, Epidermal electronics. Science 333, 838-843 (2011).
2. J. A. Rogers, Electronics for the human body. JAMA 313, 561-562 (2015).

3. M. Kaltenbrunner, T. Sekitani, J. Reeder, T. Yokota, K. Kuribara, T. Tokuhara, M. Drack, R. Schwödiauer, I. Graz, S. Bauer-Gogonea, An ultra-lightweight design for imperceptible plastic electronics. Nature 499, 458-463 (2013).
4. D. J. Lipomi, M. Vosgueritchian, B. C. Tee, S. L. Hellstrom, J. A. Lee, C. H. Fox, Z. Bao, Skin-like pressure and strain sensors based on transparent elastic films of carbon nanotubes. Nature Nanotech. 6, 788-792 (2011).
5. K. Takei, T. Takahashi, J. C. Ho, H. Ko, A. G. Gillies, P. W. Leu, R. S. Fearing, A. Javey, Nanowire active-matrix circuitry for low-voltage macroscale artificial skin. Nature Mater. 9, 821-826 (2010).
6. D. Kang, P. V. Pikhitsa, Y. W. Choi, C. Lee, S. S. Shin, L. Piao, B. Park, K.-Y. Suh, T.-i. Kim, M. Choi, Ultrasensitive mechanical crack-based sensor inspired by the spider sensory system. Nature 516, 222-226 (2014).
7. C. Dagdeviren, Y. Shi, P. Joe, R. Ghaffari, G. Balooch, K. Usgaonkar, O. Gur, P. L. Tran, J. R. Crosby, M. Meyer, Conformal piezoelectric systems for clinical and experimental characterization of soft tissue biomechanics. Nature Mater. 14, 728-736 (2015).
8. R. C. Webb, A. P. Bonifas, A. Behnaz, Y. Zhang, K. J. Yu, H. Cheng, M. Shi, Z. Bian, Z. Liu, Y.-S. Kim, Ultrathin conformal devices for precise and continuous thermal characterization of human skin. Nature Mater. 12, 938-944 (2013).
9. J. Viventi, D.-H. Kim, L. Vigeland, E. S. Frechette, J. A. Blanco, Y.-S. Kim, A. E. Avrin, V. R. Tiruvadi, S.-W. Hwang, A. C. Vanleer, Flexible, foldable, actively multiplexed, high-density electrode array for mapping brain activity in vivo. Nat. Neurosci. 14, 1599-1605 (2011).
10. J.-W. Jeong, W.-H. Yeo, A. Akhtar, J. J. S. Norton, Y.-J. Kwack, S. Li, S.-Y. Jung, Y. Su, W. Lee, J. Xia, H. Cheng, Y. Huang, W.-S. Choi, T. Bretl, J. A. Rogers, Materials and optimized designs for human-machine interfaces via epidermal electronics. Advanced Materials 25, 6839-6846 (2013).
11. G. Matzeu, L. Florea, D. Diamond, Advances in wearable chemical sensor design for monitoring biological fluids. Sens. Actuators B Chem. 211, 403-418 (2015).
12. S. Corrie, J. Coffey, J. Islam, K. Markey, M. Kendall, Blood, sweat, and tears: developing clinically relevant protein biosensors for integrated body fluid analysis. Analyst 140, 4350-4364 (2015).
13. Z. Sonner, E. Wilder, J. Heikenfeld, G. Kasting, F. Beyette, D. Swaile, F. Sherman, J. Joyce, J. Hagen, N. Kelley-Loughnane, R. Naik, The microfluidics of the eccrine sweat gland, including biomarker partitioning, transport, and biosensing implications. Biomicrofluidics 9, 031301 (2015).
14. W. Gao, S. Emaminejad, H. Y. Y. Nyein, S. Challa, K. Chen, A. Peck, H. M. Fahad, H. Ota, H. Shiraki, D. Kiriya, D.-H. Lien, G. A. Brooks, R. W. Davis, A. Javey, Fully integrated wearable sensor arrays for multiplexed in situ perspiration analysis. Nature 529, 509-514 (2016).
15. J. Heikenfeld, Non-invasive Analyte Access and Sensing through Eccrine Sweat: Challenges and Outlook circa 2016. Electroanalysis 28, 1242-1249 (2016).
16. P. Salvo, F. Di Francesco, D. Costanzo, C. Ferrari, M. G. Trivella, D. De Rossi, A wearable sensor for measuring sweat rate. IEEE Sensors J. 10, 1557-1558 (2010).
17. S. Jadoon, S. Karim, M. R. Akram, A. Kalsoom Khan, M. A. Zia, A. R. Siddiqi, G. Murtaza, Recent developments in sweat analysis and its applications. (2015), vol. 2015, pp. 7.
18. S. M. Shirreffs, R. J. Maughan, Whole body sweat collection in humans: an improved method with preliminary data on electrolyte content. J. Appl. Physiol. 82, 336-341 (1997).
19. V. A. LeGrys, R. Applequist, P. Farrell, R. Hickstein, S. F. Lo, R. Passarell, D. W. Rheinheimer, B. J. Rosenstein, J. E. Vaks, Sweat testing: Sample collection and quantitative Analysis, approved guideline [Document C34-A3]. (National Committee for Clinical Laboratory Standards, Wayne, Pa., 2000).
20. S. Coyle, K. T. Lau, N. Moyna, D. O'Gorman, D. Diamond, F. Di Francesco, D. Costanzo, P. Salvo, M. G. Trivella, D. E. De Rossi, N. Taccini, R. Paradiso, J. A. Porchet, A. Ridolfi, J. Luprano, C. Chuzel, T. Lanier, F. Revol-Cavalier, S. Schoumacker, V. Mourier, I. Chartier, R. Convert, H. De-Moncuit, C. Bini, BIOTEX—biosensing textiles for personalised healthcare management. IEEE Trans. Inf. Technol. Biomed. 14, 364-370 (2010).
21. W. Jia, A. J. Bandodkar, G. Valdes-Ramirez, J. R. Windmiller, Z. Yang, J. Ramírez, G. Chan, J. Wang, Electrochemical tattoo biosensors for real-time noninvasive lactate monitoring in human perspiration. Analytical Chemistry 85, 6553-6560 (2013).
22. T. Guinovart, A. J. Bandodkar, J. R. Windmiller, F. J. Andrade, J. Wang, A potentiometric tattoo sensor for monitoring ammonium in sweat. Analyst 138, 7031-7038 (2013).
23. A. J. Bandodkar, D. Molinnus, O. Mirza, T. Guinovart, J. R. Windmiller, G. Valdes-Ramirez, F. J. Andrade, M. J. Schoning, J. Wang, Epidermal tattoo potentiometric sodium sensors with wireless signal transduction for continuous non-invasive sweat monitoring. Biosens. Bioelectron. 54, 603-609 (2014).
24. V. F. Curto, C. Fay, S. Coyle, R. Byrne, C. O'Toole, C. Barry, S. Hughes, N. Moyna, D. Diamond, F. Benito-Lopez, Real-time sweat pH monitoring based on a wearable chemical barcode micro-fluidic platform incorporating ionic liquids. Sensor. Atuat. B-Chem. 171-172, 1327-1334 (2012).
25. V. Oncescu, D. O'Dell, D. Erickson, Smartphone based health accessory for colorimetric detection of biomarkers in sweat and saliva. Lab. Chip. 13, 3232-3238 (2013).
26. L. Shen, J. A. Hagen, I. Papautsky, Point-of-care colorimetric detection with a smartphone. Lab on a Chip 12, 4240-4243 (2012).
27. D. Rose, M. Ratterman, D. Griffin, L. Hou, N. Kelley-Loughnane, R. Naik, J. Hagen, I. Papautsky, J. Heikenfeld, Adhesive RFID sensor patch for monitoring of sweat electrolytes. IEEE Trans. Biomed. Eng. 62, 1457-1465 (2014).
28. X. Huang, Y. Liu, K. Chen, W.-J. Shin, C.-J. Lu, G.-W. Kong, D. Patnaik, S.-H. Lee, J. F. Cortes, J. A. Rogers, Stretchable, wireless sensors and functional substrates for epidermal characterization of sweat. Small 10, 3083-3090 (2014).
29. L. Gao, Y. Zhang, V. Malyarchuk, L. Jia, K.-I. Jang, R. Chad Webb, H. Fu, Y. Shi, G. Zhou, L. Shi, D. Shah, X. Huang, B. Xu, C. Yu, Y. Huang, J. A. Rogers, Epidermal photonic devices for quantitative imaging of temperature and thermal transport characteristics of the skin. Nat Commun 5, (2014).
30. T.-i. Kim, J. G. McCall, Y. H. Jung, X. Huang, E. R. Siuda, Y. Li, J. Song, Y. M. Song, H. A. Pao, R.-H. Kim, Injectable, cellular-scale optoelectronics with applications for wireless optogenetics. Science 340, 211-216 (2013). 31. J.-W. Jeong, Jordan G. McCall, G. Shin, Y. Zhang, R. Al-Hasani, M. Kim, S. Li, Joo Y. Sim, K.-I.

Jang, Y. Shi, Daniel Y. Hong, Y. Liu, Gavin P. Schmitz, L. Xia, Z. He, P. Gamble, Wilson Z. Ray, Y. Huang, Michael R. Bruchas, John A. Rogers, Wireless optofluidic systems for programmable in vivo pharmacology and optogenetics. Cell 162, 662-674 (2015).
32. K. Sato, F. Sato, Individual variations in structure and function of human eccrine sweat gland. Am. J. Physiol. Regul. Integr. Comp. Physiol. 245, R203-R208 (1983).
33. J. Klode, L. Schöttler, I. Stoffels, A. Körber, D. Schadendorf, J. Dissemond, Investigation of adhesion of modern wound dressings: a comparative analysis of 56 different wound dressings. Journal of the European Academy of Dermatology and Venereology 25, 933-939 (2011).
34. K. Wilke, A. Martin, L. Terstegen, S. S. Biel, A short history of sweat gland biology. Int. J. Cosmet. Sci. 29, 169-179 (2007).
35. J. N. Lee, C. Park, G. M. Whitesides, Solvent compatibility of poly (dimethylsiloxane)-based microfluidic devices. Anal. Chem. 75, 6544-6554 (2003).
36. D.-H. Kim, R. Ghaffari, N. Lu, J. A. Rogers, Flexible and Stretchable Electronics for Biointegrated Devices. Annual Review of Biomedical Engineering 14, 113-128 (2012).
37. C. H. Lee, Y. Ma, K. I. Jang, A. Banks, T. Pan, X. Feng, J. S. Kim, D. Kang, M. S. Raj, B. L. McGrane, B. Morey, X. Wang, R. Ghaffari, Y. Huang, J. A. Rogers, Soft core/dhell packages for stretchable electronics. Adv. Funct. Mater. 25, 3698-3704 (2015).
38. X. Liang, S. Boppart, Biomechanical properties of in vivo human skin from dynamic optical coherence elastography. IEEE Trans. Biomed. Eng. 57, 953-959 (2010).
39. J. Kim, A. Banks, H. Y. Cheng, Z. Q. Xie, S. Xu, K. I. Jang, J. W. Lee, Z. J. Liu, P. Gutruf, X. Huang, P. H. Wei, F. Liu, K. Li, M. Dalal, R. Ghaffari, X. Feng, Y. G. Huang, S. Gupta, U. Paik, J. A. Rogers, Epidermal electronics with advanced capabilities in near-field communication. Small 11, 906-912 (2015).
40. Y. Y. Huang, W. Zhou, K. J. Hsia, E. Menard, J.-U. Park, J. A. Rogers, A. G. Alleyne, Stamp collapse in soft lithography. Langmuir 21, 8058-8068 (2005).
41. C. Pang, G. Y. Lee, T. I. Kim, S. M. Kim, H. N. Kim, S. H. Ahn, K. Y. Suh, A flexible and highly sensitive strain-gauge sensor using reversible interlocking of nanofibres. Nature Mater. 11, 795-801 (2012).
42. L. Hou, J. Hagen, X. Wang, I. Papautsky, R. Naik, N. Kelley-Loughnane, J. Heikenfeld, Artificial microfluidic skin for in vitro perspiration simulation and testing. Lab on a Chip 13, 1868-1875 (2013).
43. N. A. Taylor, C. A. Machado-Moreira, Regional variations in transepidermal water loss, eccrine sweat gland density, sweat secretion rates and electrolyte composition in resting and exercising humans. Extrem. Physiol. Med. 2, 1-30 (2013).
44. A. Polliack, R. Taylor, D. Bader, Sweat analysis following pressure ischaemia in a group of debilitated subjects. JRRD 34, 303-308 (1997).
45. S. Biagi, S. Ghimenti, A. Onor, E. Bramanti, Simultaneous determination of lactate and pyruvate in human sweat using reversed-phase high-performance liquid chromatography: a noninvasive approach. Biomed. Chromatogr. 26, 1408-1415 (2012).
46. I. Alvear-Ordenes, D. García-López, J. A. De Paz, J. González-Gallego, Sweat lactate, ammonia, and urea in rugby players. Int J Sports Med 26, 632-637 (2005).
47. L. S. Lamont, Sweat lactate secretion during exercise in relation to women's aerobic capacity. Journal of Applied Physiology 62, 194-198 (1987).
48. A. W. Martinez, S. T. Phillips, M. J. Butte, G. M. Whitesides, Patterned paper as a platform for inexpensive, low-volume, portable bioassays. Angew. Chem. Int. Edit. 46, 1318-1320 (2007).
49. A. W. Martinez, S. T. Phillips, E. Carrilho, S. W. Thomas, H. Sindi, G. M. Whitesides, Simple telemedicine for developing regions: camera phones and paper-based microfluidic devices for real-time, off-site diagnosis. Anal. Chem. 80, 3699-3707 (2008).
50. T. C. Boysen, S. Yanagawa, F. Sato, K. Sato, A modified anaerobic method of sweat collection. Journal of Applied Physiology 56, 1302-1307 (1984).
51. H. Crocker, M. Shephard, G. White, Evaluation of an enzymatic method for determining creatinine in plasma. Journal of clinical pathology 41, 576-581 (1988).
52. H. Wei, E. Wang, Fe3O4 Magnetic Nanoparticles as Peroxidase Mimetics and Their Applications in H2O2 and Glucose Detection. Analytical Chemistry 80, 2250-2254 (2008).
53. Y. Song, K. Qu, C. Zhao, J. Ren, X. Qu, Graphene oxide: intrinsic peroxidase catalytic activity and its application to glucose detection. Advanced Materials 22, 2206-2210 (2010).
54. C. J. Smith, G. Havenith, Body mapping of sweating patterns in male athletes in mild exercise-induced hyperthermia. Eur. J. Appl. Physiol. 111, 1391-1404 (2011).
55. P. B. Licht, H. K. Pilegaard, Severity of compensatory sweating after thoracoscopic sympathectomy. Ann. Thorac. Surg. 78, 427-431 (2004).
56. Y. Fainman, L. Lee, D. Psaltis, C. Yang, Optofluidics: Fundamentals, Devices, and Applications Ch. 2. (McGraw-Hill Education, New York, N.Y., 2009).
57. E. Ventsel, T. Krauthammer, Thin plates and shells: theory: analysis, and applications ch. 3. (CRC press, Boca Raton, Fla., 2001).
58. F. M. White, Fluid Mechanics. Edition 7 ch. 6. (McGraw-Hill Higher Education, New York, N W, 2010).

REFERENCES FROM EXAMPLE 2

1. Mena-Bravo, A.; Luque de Castro, M. D., J Pharm Biomed Anal 2014, 90, 139-47. DOI 10.1016/j.jpba.2013.10.048.
2. Dill, D. B.; Costill, D. L., J Appl Physiol 1974, 37 (2), 247-8.
3. Gibson, L. E.; Cooke, R. E., Pediatrics 1959, 23 (3), 545-9.
4. di Sant'Agnese, P. A.; Darling, R. C.; Perera, G. A.; Shea, E., The American Journal of Medicine 1953, 15 (6), 777-784. DOI 10.1016/0002-9343(53)90169-7.
5. Boysen, T. C.; Yanagawa, S.; Sato, F.; Sato, K., J Appl Physiol Respir Environ Exerc Physiol 1984, 56 (5), 1302-7. DOI papers3://publication/uuid/A4A72F12-DA98-4795-85E7-97970D5646A1.
6. Fukumoto, T.; Tanaka, T.; Fujioka, H.; Yoshihara, S.; Ochi, T.; Kuroiwa, A., Clin Cardiol 1988, 11 (10), 707-9. DOI papers3://publication/uuid/0085597F-FD26-4EEE-8996-2E97F7E3404D.
7. Shamsuddin, A. K.; Yanagimoto, S.; Kuwahara, T.; Zhang, Y.; Nomura, C.; Kondo, N., Eur J Appl Physiol 2005, 94 (3), 292-7. DOI 10.1007/s00421-005-1314-7.
8. Kidwell, D. A.; Smith, F. P., Forensic Sci Int 2001, 116 (2-3), 89-106. DOI Doi 10.1016/S0379-0738(00)00353-4.
9. Hammond, K. B.; Turcios, N. L.; Gibson, L. E., J Pediatr 1994, 124 (2), 255-60. DOI Doi 10.1016/S0022-3476(94)70314-0.

10. Bandodkar, A. J.; Hung, V. W.; Jia, W.; Valdes-Ramirez, G.; Windmiller, J. R.; Martinez, A. G.; Ramirez, J.; Chan, G.; Kerman, K.; Wang, J., Analyst 2013, 138 (1), 123-8. DOI 10.1039/c2an36422k.
11. Guinovart, T.; Bandodkar, A. J.; Windmiller, J. R.; Andrade, F. J.; Wang, J., Analyst 2013, 138 (22), 7031-8. DOI 10.1039/c3an01672b.
12. Bandodkar, A. J.; Molinnus, D.; Mirza, O.; Guinovart, T.; Windmiller, J. R.; Valdes-Ramirez, G.; Andrade, F. J.; Schoning, M. J.; Wang, J., Biosens Bioelectron 2014, 54 (C), 603-9. DOI 10.1016/j.bios.2013.11.039.
13. Kim, J.; de Araujo, W. R.; Samek, I. A.; Bandodkar, A. J.; Jia, W. Z.; Brunetti, B.; Paixao, T. R. L. C.; Wang, J., Electrochemistry Communications 2015, 51 (C), 41-45. DOI 10.1016/j.elecom.2014.11.024.
14. Gao, W.; Emaminejad, S.; Nyein, H. Y.; Challa, S.; Chen, K.; Peck, A.; Fahad, H. M.; Ota, H.; Shiraki, H.; Kiriya, D.; Lien, D. H.; Brooks, G. A.; Davis, R. W.; Javey, A., Nature 2016, 529 (7587), 509-14. DOI 10.1038/nature16521.
15. Imani, S.; Bandodkar, A. J.; Mohan, A. M.; Kumar, R.; Yu, S.; Wang, J.; Mercier, P. P., Nat Commun 2016, 7, 11650. DOI 10.1038/ncomms11650.
16. Nyein, H. Y.; Gao, W.; Shahpar, Z.; Emaminejad, S.; Challa, S.; Chen, K.; Fahad, H. M.; Tai, L. C.; Ota, H.; Davis, R. W.; Javey, A., Acs Nano 2016, 10 (7), 7216-24. DOI 10.1021/acsnano.6b04005.
17. Huang, X.; Liu, Y.; Chen, K.; Shin, W. J.; Lu, C. J.; Kong, G. W.; Patnaik, D.; Lee, S. H.; Cortes, J. F.; Rogers, J. A., Small 2014, 10 (15), 3083-90. DOI 10.1002/smll.201400483.
18. Schulz, I. J., J Clin Invest 1969, 48 (8), 1470-7. DOI 10.1172/JCI106113.
19. Sonner, Z.; Wilder, E.; Heikenfeld, J.; Kasting, G.; Beyette, F.; Swaile, D.; Sherman, F.; Joyce, J.; Hagen, J.; Kelley-Loughnane, N.; Naik, R., Biomicrofluidics 2015, 9 (3), 031301. DOI 10.1063/1.4921039.
20. Ullmann, A.; Fono, I., J Microelectromech S 2002, 11 (6), 655-664. DOI 10.1109/Jmems.2002.805048.
21. Chen, C. H.; Santiago, J. G., J Microelectromech S 2002, 11 (6), 672-683. DOI 10.1109/Jmems.2002.805055.
22. Zhao, B.; Moore, J. S.; Beebe, D. J., Anal Chem 2002, 74 (16), 4259-68. DOI 10.1021/ac020269w.
23. Chen, J. M.; Huang, P. C.; Lin, M. G., Microfluid Nanofluid 2008, 4 (5), 427-437. DOI 10.1007/s10404-007-0196-x.
24. Kong, L. X.; Perebikovsky, A.; Moebius, J.; Kulinsky, L.; Madou, M., J Lab Autom 2016, 21 (3), 323-55. DOI 10.1177/2211068215588456.
25. Madou, M.; Zoval, J.; Jia, G.; Kido, H.; Kim, J.; Kim, N., Annu Rev Biomed Eng 2006, 8, 601-28. DOI 10.1146/annurev.bioeng.8.061505.095758.
26. Glass, N. R.; Shilton, R. J.; Chan, P. P.; Friend, J. R.; Yeo, L. Y., Small 2012, 8 (12), 1881-8. DOI 10.1002/smll.201102282.
27. Choi, J.; Jung, Y. G.; Kim, J.; Kim, S.; Jung, Y.; Na, H.; Kwon, S., Lab Chip 2013, 13 (2), 280-7. DOI 10.1039/c2lc41055a.
28. Brassard, D.; Clime, L.; Li, K.; Geissler, M.; Miville-Godin, C.; Roy, E.; Veres, T., Lab Chip 2011, 11 (23), 4099-107. DOI 10.1039/c1lc20714h.
29. Lee, J. N.; Park, C.; Whitesides, G. M., Anal Chem 2003, 75 (23), 6544-6554. DOI 10.1021/ac0346712.
30. Halldorsson, S.; Lucumi, E.; Gomez-Sjoberg, R.; Fleming, R. M. T., Biosens Bioelectron 2015, 63, 218-231. DOI 10.1016/j.bios.2014.07.029.
31. Bietsch, A.; Michel, B., J Appl Phys 2000, 88 (7), 4310-4318. DOI Doi 10.1063/1.1289816.
32. Khang, D. Y.; Jiang, H. Q.; Huang, Y.; Rogers, J. A., Science 2006, 311 (5758), 208-212. DOI 10.1126/science.1121401.
33. Lotters, J. C.; Olthuis, W.; Veltink, P. H.; Bergveld, P., J Micromech Microeng 1997, 7 (3), 145-147. DOI Doi 10.1088/0960-1317/7/3/017.
34. Cho, H.; Kim, H. Y.; Kang, J. Y.; Kim, T. S., J Colloid Interface Sci 2007, 306 (2), 379-85. DOI 10.1016/j.jcis.2006.10.077.
35. Huang, C. P.; Lu, J.; Seon, H.; Lee, A. P.; Flanagan, L. A.; Kim, H. Y.; Putnam, A. J.; Jeon, N. L., Lab Chip 2009, 9 (12), 1740-8. DOI 10.1039/b818401a.
36. Eddington, D. T.; Puccinelli, J. P.; Beebe, D. J., Sensor Actuat B-Chem 2006, 114 (1), 170-172. DOI 10.1016/j.snb.2005.04.037.
37. Bhagat, A. A. S.; Peterson, E. T. K.; Papautsky, I., J Micromech Microeng 2007, 17 (5), 1017-1024. DOI 10.1088/0960-1317/17/5/023.
38. Xia, H. M.; Wan, S. Y. M.; Shu, C.; Chew, Y. T., Lab Chip 2005, 5 (7), 748-755. DOI 10.1039/b502031j.
39. Taylor, N. A.; Machado-Moreira, C. A., Extrem Physiol Med 2013, 2 (1), 4. DOI 10.1186/2046-7648-2-4.
40. Sato, K.; Sato, F., Am J Physiol 1983, 245 (2), R203-R208.
41. Licht, P. B.; Pilegaard, H. K., Ann Thorac Surg 2004, 78 (2), 427-431. DOI 10.1016/j.athoracsur.2004.02.087.
42. Costa, F.; Calloway, D. H.; Margen, S., Am J Clin Nutr 1969, 22 (1), 52-&.
43. Mickelsen, O.; Keys, A., J Biol Chem 1943, 149 (2), 479-490.

We claim:

1. A device for handling a biofluid comprising:
a soft and flexible functional substrate for adhering and conforming to a surface of the skin, said functional substrate comprising a microfluidic network channel having a plurality of microchannels, reservoirs and passive burst valves configured for time-dependent collection of said biofluid; and
a plurality of sensors supported by said functional substrate and configured for multiparametric analysis of said biofluid;
wherein said functional substrate provides for microfluidic transport of at least a portion of said biofluid to said sensors; and
wherein said plurality of sensors include at least a first sensor configured for determining a first concentration of an analyte over a first concentration range and a second sensor configured for determining a second concentration of said analyte or a different analyte over a second concentration range different from said first concentration range to provide multiparametric and chrono-sampling of said biofluid.

2. The device of claim 1,
wherein each reservoir receives biofluid corresponding to a different time interval.

3. A device for handling a biofluid comprising:
a soft and flexible functional substrate for adhering and conforming to a surface of the skin; and
a plurality of sensors or biofluid collection structures supported by said functional substrate;
wherein said functional substrate comprises a microfluidic network channel having a plurality of microchannels, reservoirs and passive burst valves configured for time-dependent collection of said biofluid and to provide for microfluidic transport of said biofluid including transport of a first portion of said biofluid to said one or more sensors or biofluid collection structures and transport of a second portion of said biofluid away from said device;

wherein said plurality of sensors or biofluid collection structures include at least a first sensor configured for determining a first concentration of an analyte over a first concentration range and a second sensor configured for determining a second concentration of said analyte or a different analyte over a second concentration range different from said first concentration range to provide multiparametric and temporal profiling as a function of time.

4. The device of claim 1, wherein said sensors provide for characterization of at least one temporal property of said biofluid and said temporal property of said biofluid is characterized over a time domain selected from the range of 10 μs to 24 hrs.

5. The device of claim 1, wherein said sensors provide for characterization of at least one temporal property of said biofluid and said temporal property of said biofluid is a biofluid release rate as a function of time or a biofluid release volume as a function of time.

6. The device of claim 5, wherein said temporal property of said biofluid is a sweat rate as a function of time or a total sweat volume loss as a function of time.

7. The device of claim 1, wherein said temporal property of said biofluid is a time dependent concentration or amount of one or more analytes in said biofluid.

8. The device of claim 7, wherein said sensors provide for characterization of at least one temporal property of said biofluid and said temporal property of said biofluid is a time dependent concentration of one or more biomarkers in said biofluid.

9. The device of claim 8, wherein said temporal property is a multi-parametric property including the concentrations or amounts of at least two biomarkers as a function of time.

10. The device of claim 8, wherein said one or more biomarkers is one or more electrolytes, metabolites or proteins.

11. The device of claim 3, wherein said sensors or biofluid collection structures are positioned on a support surface of said functional substrate.

12. The device of claim 3, wherein said sensors or biofluid collection structures are integrated with said functional substrate.

13. The device of claim 1, wherein said functional substrate is mechanically or thermally matched to said skin.

14. The device of claim 1, wherein said functional substrate is capable of adhering to said surface of said skin, with an adhesion force selected from the range of 1 N to 20 N.

15. The device of claim 1, wherein said functional substrate has one or more inlets capable of exchanging fluid with said surface of said skin.

16. The device of claim 15, wherein said functional substrate forms a watertight seal with said skin around said one or more inlets.

17. The device of claim 1, wherein said functional substrate comprises a porous material, a micro-machined material, a woven material, a mesh material or a fibrous material.

18. The device of claim 1, wherein said functional substrate comprises an adhesive layer having a plurality of openings.

19. The device of claim 1, wherein said plurality of microchannels spatially route at least a selected portion of said biofluid.

20. The device of claim 19, wherein said microfluidic network channel comprises an elastomeric material.

21. The device of claim 19, wherein said microfluidic network comprises a first layer embossed with a relief geometry corresponding to said microchannels and a second top capping layer.

22. The device of claim 19, wherein said transport of biofluid is generated via capillary action, natural pressure of said biofluid or a combination of these.

23. The device of claim 1, wherein said microchannels, reservoirs or both are closed to the ambient atmosphere.

24. The device of claim 1, wherein said microchannels, reservoirs or both are connected via one or more passive burst valves for time dependent collection, analysis or storage of said biofluid.

25. The device of claim 24, wherein at least a portion of said passive burst valves are selective super absorbent polymer (SAP) valves, hydrophobic valves, capillary bursting valves or a combination thereof.

26. The device of claim 23, wherein said passive burst valve closes after said reservoir or microchannel is filled with biofluid, thereby preventing loss or release of collected biofluid from a filled reservoir or microchannel.

27. The device of claim 23, wherein different microchannels of said network are in fluid communication with different reservoirs.

28. The device of claim 24, wherein at least a portion of said microchannels of said network are directionally selective.

29. The device of claim 19, wherein said microfluidic network channel further comprises one or more outlets in fluid communication with said microchannels for reducing backpressure in said microfluidic network.

30. The device of claim 29, wherein said one or more outlets comprise openings, membranes or a combination thereof.

31. The device of claim 19, wherein said functional substrate further comprise one or more openings providing for passage of an unsampled portion of said biofluid away from said device, wherein said unsampled portion of said biofluid is transported away vertically or laterally relative to the interface of said device and said skin.

32. The device of claim 1, wherein said functional substrate has a Young's modulus less than or equal to 100 MPa.

33. The device of claim 1, wherein said functional substrate has a thickness selected from a range of 500 μm to 2 mm.

34. The device of claim 1, wherein the functional substrate comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA) and polycarbonate.

35. The device of claim 1, wherein the functional substrate has a lateral foot print less than or equal to 1000 $mm^2$.

36. The device claim 1, wherein the functional substrate has a porosity greater than or equal to 0.01.

37. The device of claim 1, wherein said sensors comprise colorimetric sensors having one or more color-responsive reagents for quantification of a volume, flow rate, composition or any combination of these of said biofluid, wherein said one or more color-responsive reagents are indicator reagents that react with one or more biomarkers in said biofluid.

38. The device of claim 37, wherein said one or more color-responsive reagents are selected from the group consisting of CoCl$_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator and any combination of these.

39. The device of claim 37, wherein said one or more color-responsive reagents are provided in:
   a biofluid collection structure of said microfluidic network channel;
   said reservoir; or
   said microchannels.

40. The device of claim 39, wherein said biofluid collection structure, reservoir, or microfluidic channel of said microfluidic network channel is at least partially optically transparent in the visible or infrared region of the electromagnetic spectrum.

41. The device of claim 39, wherein said biofluid collection structure having said color-responsive reagents is characterized by a volume selected over the range of 1000 μm$^3$-1000 mm$^3$.

42. The device of claim 39, wherein said one or more color-responsive reagents are immobilized within said biofluid collection structure; within or on one or more walls of said biofluid collection structure; within a hydrogel provided within said biofluid collection structure.

43. The device of claim 39, wherein said color-responsive reagents are provided along the length of said biofluid collection structure comprising a microfluidic channel, wherein the volume of the biofluid in said microfluidic channel is sensed as the biofluid fills said microfluidic channel.

44. The device of claim 43, wherein a leading edge of said volume of biofluid in said microfluidic channel is sensed as a function of time.

45. The device of claim 44, wherein the lead edge of the volume of the biofluid in said microfluidic channel is sensed optically.

46. The device of claim 43, wherein said microfluidic channel is a serpentine microfluidic channel.

47. The device of claim 43, wherein said color-responsive reagent is provided in said biofluid collection structure, and wherein the concentration of the one or more biomarkers in said biofluid are sensed as said biofluid is provided to said biofluid collection structure.

48. The device of claim 47, wherein the concentrations of the one or more biomarkers in said biofluid are sensed optically.

49. The device of claim 1, wherein said microchannels are characterized by a length selected from a range of 1 mm to 50 cm or a cross sectional area selected from a range of 100 μm$^2$ to 10 mm$^2$.

50. The device of claim 1, wherein the device actively generates an NFC signal and the device is read-out actively.

51. The device of claim 1, wherein said biofluid is selected from the group consisting of sweat, tears, saliva, gingival crevicular fluid, interstitial fluid, blood and combinations thereof.

52. The device of claim 1 for determining the concentration in one or more biomarkers in said biofluid.

53. The device of claim 52, wherein the one or more biomarkers in said biofluid are electrolytes, metabolites, or proteins.

54. The device of claim 1, further comprising an actuator.

55. The device of claim 54, wherein said actuator generates electromagnetic radiation, acoustic energy, an electric field, a magnetic field, heat, a RF signal, a voltage, a chemical change or a biological change.

56. The device of claim 54, wherein said actuator comprises a heater, a reservoir containing a chemical agent capable of causing a chemical change or a biological change, a source of electromagnetic radiation, a source of an electric field, a source of RF energy or a source of acoustic energy.

57. The device of claim 1, further comprising a transmitter, receiver or transceiver.

58. The device of claim 1, further comprising at least one coil.

59. The device of claim 58, wherein said at least one coil is a near-field communication coil.

60. The device of claim 58, wherein said at least one coil is an inductive coil.

61. The device of claim 58, wherein said at least one coil comprises a serpentine trace.

62. The device of claim 1 having a Young's modulus and a thickness within a factor of 2 of a Young's modulus and a thickness of an epidermal layer of the skin of a subject underlying the device during use.

63. The device of claim 1 having average Young's modulus less than or equal to 500 kPa.

64. The device of claim 1, wherein the device has a net bending stiffness less than or equal to 1 nN m.

65. The device of claim 1 having a footprint selected from a range of 300 mm$^2$ to 2000 cm$^2$.

66. A method of analyzing a biofluid; said method comprising:
   providing a device for handling a biofluid; said device comprising:
      a soft and flexible functional substrate for adhering and conforming to a surface of the skin, said functional substrate comprising a microfluidic network channel having a plurality of microchannels, reservoirs and passive burst valves configured for time-dependent collection of said biofluid; and
      a plurality of sensors supported by said functional substrate and configured for multiparametric analysis of said biofluid;
      wherein said functional substrate provides for microfluidic transport of at least a portion of said biofluid to said sensors; and wherein said plurality of sensors include at least a first sensor configured for determining a first concentration of an analyte over a first concentration range and a second sensor configured for determining a second concentration of said analyte or a different analyte over a second concentration range different from said first concentration range to provide multiparametric and chrono-sampling of said biofluid;
   conformally contacting said functional substrate of said device with a surface of the skin of a subject; and
   temporally analyzing said biofluid from said surface of the skin of said subject.

67. The device of claim 1, wherein said biofluid is sweat released from glands, wherein a pressure induced by the glands drives flow through the microchannels and the passive burst valves burst at different pressures for passively guiding sweat through the microchannels and reservoirs in a well-defined, time-ordered fashion.

68. The device of claim 67, wherein the microchannels, burst valves and reservoirs are arranged to provide for sequential filling of the reservoirs.

* * * * *